United States Patent
Saito et al.

(10) Patent No.: US 10,529,934 B2
(45) Date of Patent: Jan. 7, 2020

(54) METAL COMPLEX AND LIGHT EMITTING DEVICE USING THE SAME

(71) Applicant: Sumitomo Chemical Company, Limited, Chuo-ku, Tokyo (JP)

(72) Inventors: Takakazu Saito, Tsukuba (JP); Yusuke Ishii, Tsukuba (JP); Kazuei Ohuchi, Tsukuba (JP); Nobuhiko Akino, Tsukuba (JP); Rui Ishikawa, Tsukuba (JP)

(73) Assignee: Sumitomo Chemical Company, Limited, Tokyo (JP)

(*) Notice: Subject to any disclaimer, the term of this patent is extended or adjusted under 35 U.S.C. 154(b) by 301 days.

(21) Appl. No.: 15/511,553

(22) PCT Filed: Sep. 9, 2015

(86) PCT No.: PCT/JP2015/075542
§ 371 (c)(1),
(2) Date: Mar. 15, 2017

(87) PCT Pub. No.: WO2016/043097
PCT Pub. Date: Mar. 24, 2016

(65) Prior Publication Data
US 2017/0256726 A1 Sep. 7, 2017

(30) Foreign Application Priority Data
Sep. 17, 2014 (JP) .................................. 2014-188579

(51) Int. Cl.
| | |
|---|---|
| *H01L 51/54* | (2006.01) |
| *C09K 11/06* | (2006.01) |
| *H01L 51/00* | (2006.01) |
| *C07F 15/00* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *C08G 2261/95* (2013.01); *C09K 2211/1029* (2013.01); *C09K 2211/1044* (2013.01); *C09K 2211/1059* (2013.01); *C09K 2211/1074* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 2005/0176953 A1* | 8/2005 | Tuan et al. ............ | C09K 11/06 540/107 |
| 2007/0231600 A1 | 10/2007 | Kamatani et al. | |
| 2010/0019669 A1 | 1/2010 | Akino et al. | |
| 2010/0127215 A1 | 5/2010 | Boemer et al. | |
| 2012/0205585 A1 | 8/2012 | Okamura et al. | |
| 2016/0329508 A1 | 11/2016 | Saito et al. | |

FOREIGN PATENT DOCUMENTS

| | | |
|---|---|---|
| CN | 101146814 A | 3/2008 |
| CN | 101679856 A | 3/2010 |
| CN | 103936791 A | 7/2014 |
| JP | 2007269734 A | 10/2007 |
| JP | 2008179617 A | 8/2008 |
| JP | 2011105701 A | 6/2011 |
| WO | 2006093466 A1 | 9/2006 |
| WO | 2008122603 A2 | 10/2008 |
| WO | 2014112657 A1 | 7/2014 |
| WO | 2015105014 A1 | 7/2015 |

OTHER PUBLICATIONS

Office Action dated Oct. 8, 2018 in TW Application No. 104130414.
(Continued)

*Primary Examiner* — Dawn L Garrett
(74) *Attorney, Agent, or Firm* — Panitch Schwarze Belisario & Nadel LLP

(57) ABSTRACT

Provided is a metal complex which is excellent in quantum yield and full width at half maximum of a light emission spectrum. The metal complex is represented by the following formula (1):

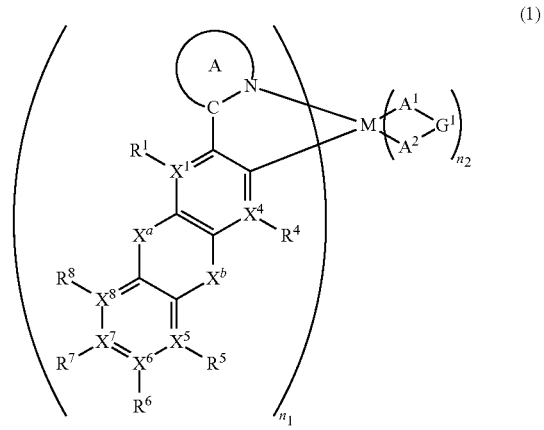

(1)

wherein M represents an iridium atom or the like, $n_1$ represents 1 to 3, $n_2$ represents 0 to 2, $X^1$ to $X^8$ represent a carbon atom or the like, $R^1$ to $R^8$ represent a hydrogen atom or the like, one of $X^a$ and $X^b$ is a single bond, and the other is a group represented by $-CR^{11}R^{12}-CR^{13}R^{14}-$, $R^{11}$ to $R^{14}$ represent an alkyl group or the like, ring A represents a heteroaromatic ring, and $A^1$-$G^1$-$A^2$ represents an anionic bidentate ligand.

14 Claims, 5 Drawing Sheets

(56) References Cited

OTHER PUBLICATIONS

Office Action dated Oct. 22, 2018 in CN Application No. 201580049646.1.
Bexon et al, "Luminescent Complexes of Iridium(III) with 6'-Phenyl-2,2'-Bipyridine and 4'-Aryl Derivatives: NC versus NN Coordination", Science Direct, vol. 8, No. 8, pp. 1326-1335 (2005).
Edkins et al., "Syntheses, Structures, and Comparison of the Photophysical Properties of Cyclometalated Iridium Complexes Containing the Isomeric 1- and 2-(2'-pyridyl)pyrene Ligands," Inorganic Chemistry, vol. 52, pp. 9842-9860 (2013).
Extended European Search Report dated Apr. 6, 2018 in EP Application No. 15841292.4.
Office Action dated May 28, 2019 in CN Application No. 201580049646.1.
English Translation of Office Action dated Oct. 29, 2019 in CN Application No. 201580049646.1.

* cited by examiner

[Fig. 1]
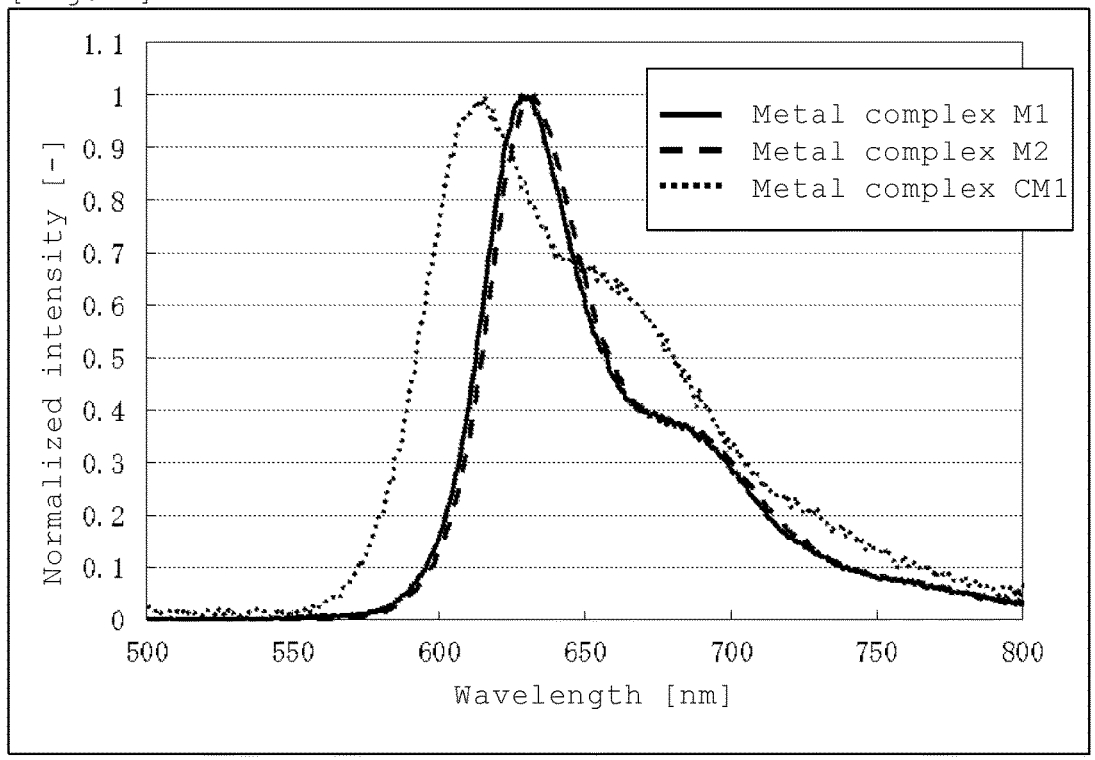

[Fig. 2]
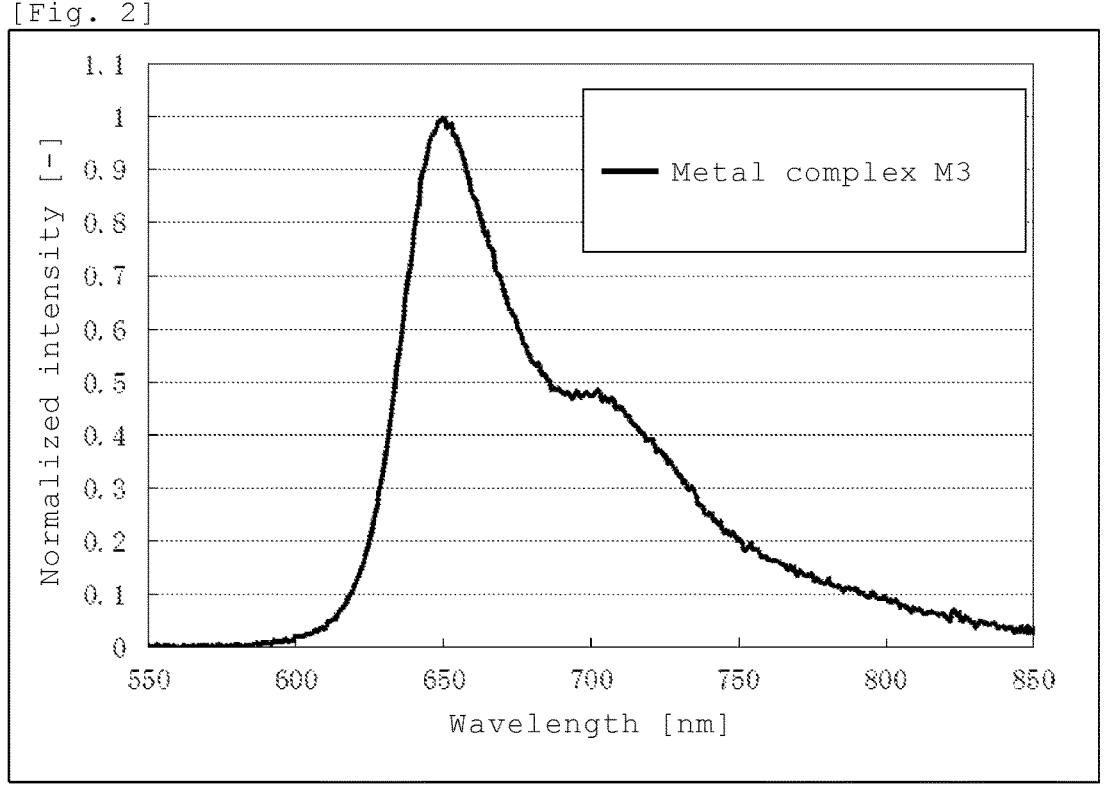

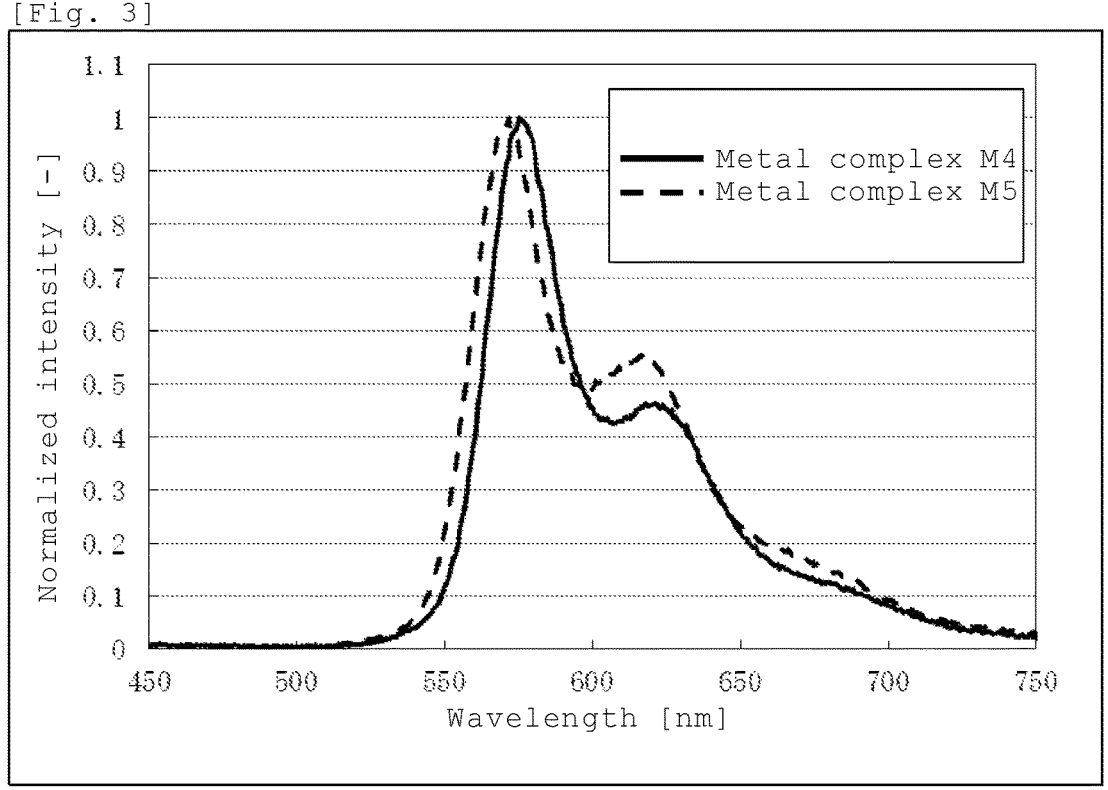
[Fig. 3]

[Fig. 4]
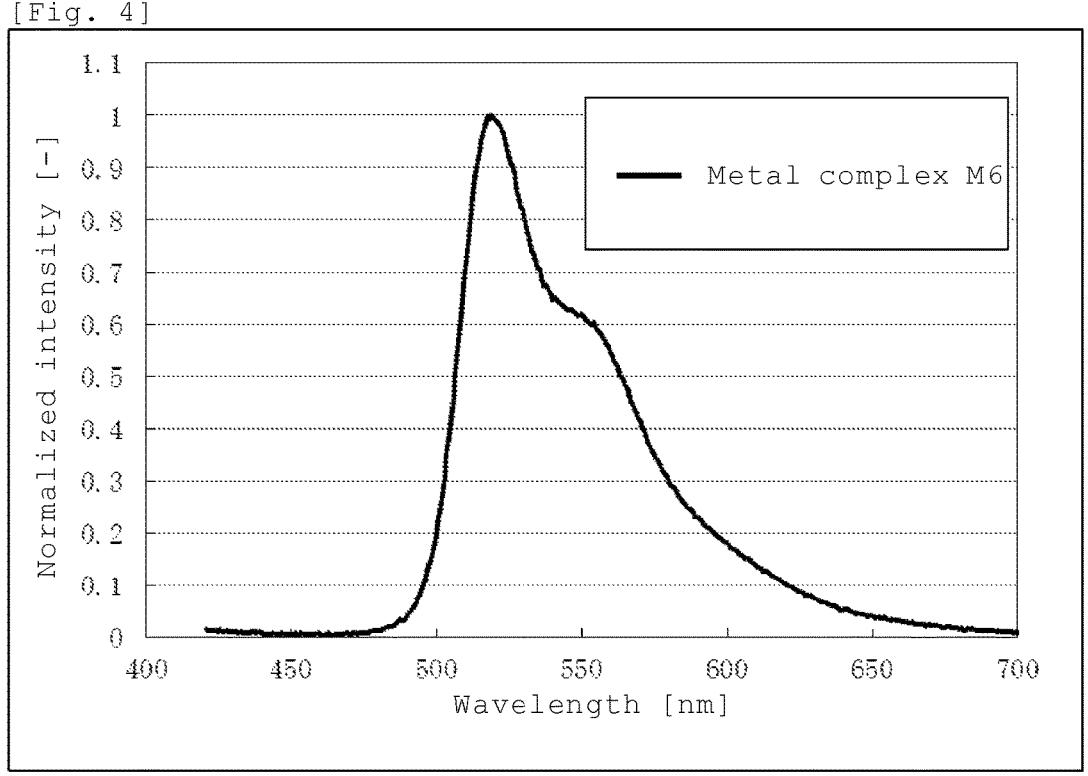

[Fig. 5]
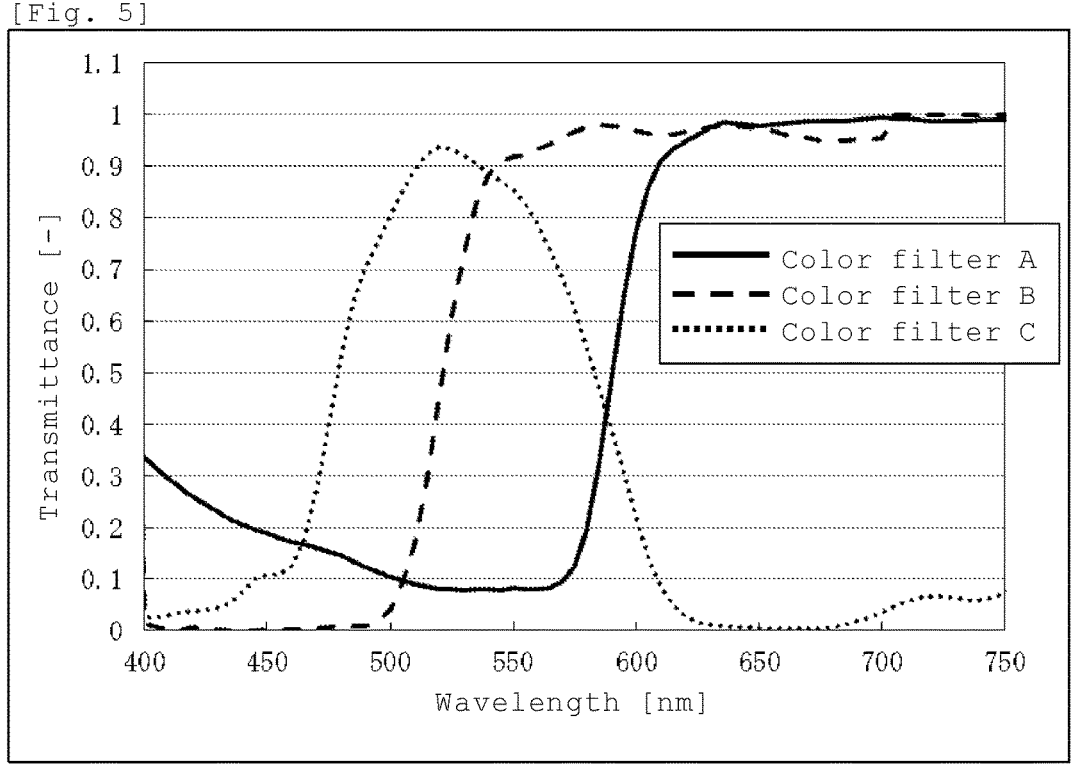

METAL COMPLEX AND LIGHT EMITTING DEVICE USING THE SAME

CROSS-REFERENCE TO RELATED APPLICATION

This application is a Section 371 of International Application No. PCT/JP2015/075542, filed Sep. 9, 2015, which was published in the Japanese language on Mar. 24, 2016, under International Publication No. WO 2016/043097 A1, and the disclosure of which is incorporated herein by reference.

TECHNICAL FIELD

The present invention relates to a metal complex and a light emitting device using the same.

BACKGROUND ART

Various phosphorescent compounds showing light emission from triplet excited state are variously investigated as a light emitting material used in a light emitting layer of a light emitting device. As the phosphorescent compound as described above, a lot of metal complexes in which the central metal is a transition metal belonging to the group 5 or group 6 of the periodic table are investigated. For example, Patent document 1 suggests a metal complex having as a ligand a phenylpyridine structure having a dendron (for example, a metal complex represented by the following formula).

PRIOR ART DOCUMENT

Patent Document

Patent document 1: JP-A No. 2011-105701

SUMMARY OF THE INVENTION

Problem to be Solved by the Invention

However, the quantum yield of the metal complex described in Patent document 1 described above (hereinafter, also referred to as "PLOY") was not sufficient. Further, the full width at half maximum of a light emission spectrum of the metal complex described in Patent document 1 described above was not fully narrow.

Then, the present invention has an object of providing a metal complex excellent in quantum yield and showing excellent full width at half maximum of a light emission spectrum. Further, the present invention has an object of providing a composition containing the metal complex and a light emitting device produced by using the metal complex.

Means for Solving the Problem

The present invention provides the following [1] to [15].

[1] A metal complex represented by the following formula (1), (2) or (3):

[Chemical Formula 1]

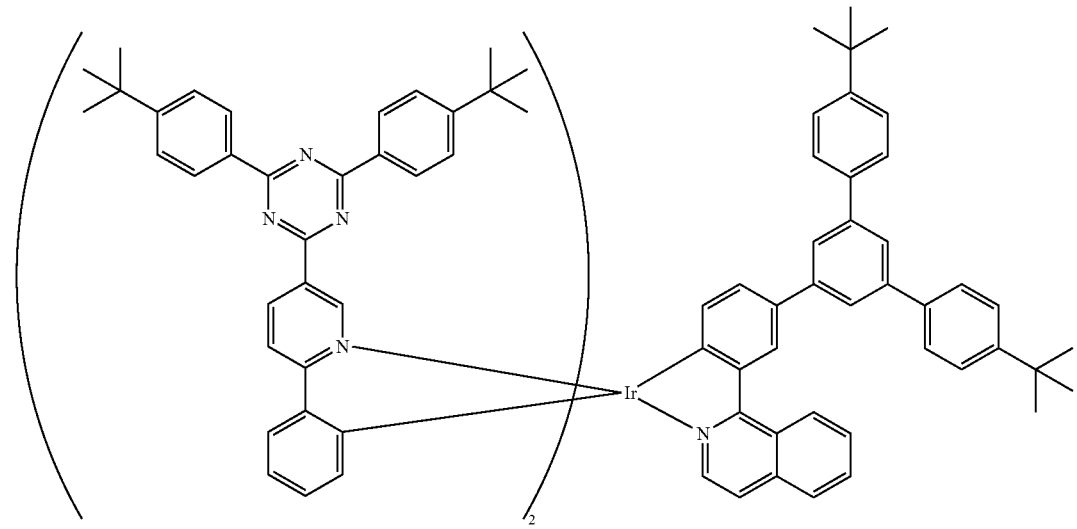

[Chemical Formula 2]

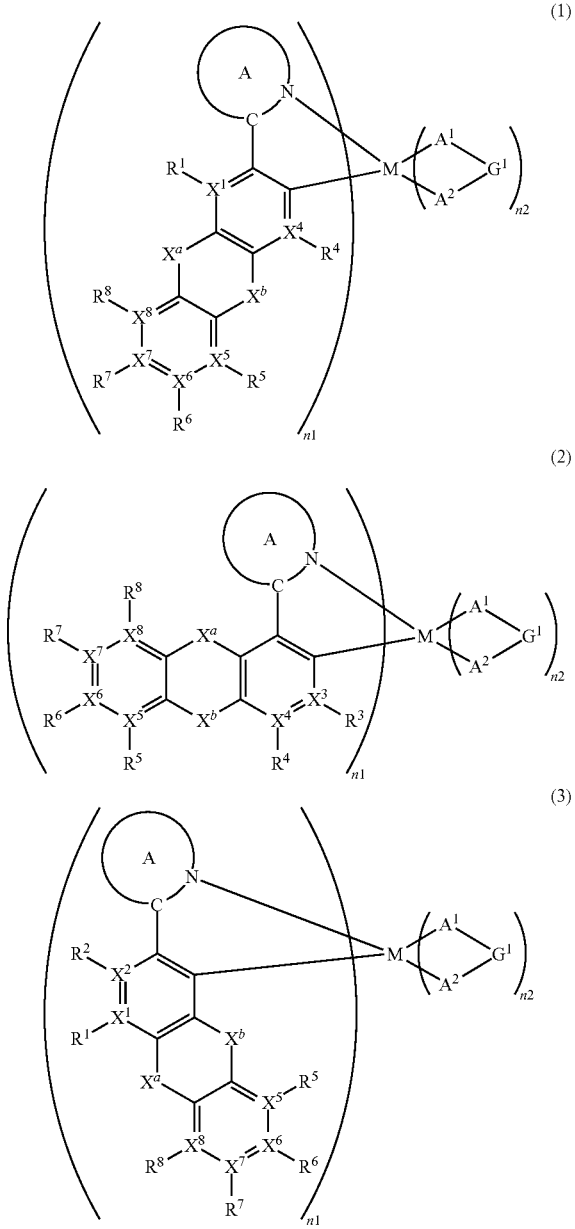

[wherein,

M represents an iridium atom or a platinum atom.

$n_1$ represents 1, 2 or 3 and $n_1$ represents 0, 1 or 2, provided that $n_1+n_2$ is 3 when M is an iridium atom and $n_1+n_2$ is 2 when M is a platinum atom.

$X^1$, $X^2$, $X^3$, $X^4$, $X^5$, $X^6$, $X^7$ and $X^8$ each independently represent a nitrogen atom or a carbon atom, provided that at least two selected from the group consisting of $X^5$, $X^6$, $X^7$ and $X^9$ are carbon atoms. When there are a plurality of $X^1$, $X^2$, $X^3$, $X^4$, $X^5$, $X^6$, $X^7$ or $X^8$, they may be the same or different at each occurrence, provided that $R^1$ is not present when $X^1$ is a nitrogen atom, $R^2$ is not present when $X^2$ is a nitrogen atom, $R^3$ is not present when $X^3$ is a nitrogen atom, $R^4$ is not present when $X^4$ is a nitrogen atom, $R^5$ is not present when $X^5$ is a nitrogen atom, $R^6$ is not present when $X^6$ is a nitrogen atom, $R^7$ is not present when $X^7$ is a nitrogen atom, and $R^8$ is not present when $X^8$ is a nitrogen atom.

$R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent, provided that $R^1$ and $R^2$, $R^3$ and $R^4$, $R^5$ and $R^6$, $R^6$ and $R^7$, and $R^7$ and $R^8$ each may be combined together to form a ring together with the atoms to which they are attached. When there are a plurality of $R^1$, $R^2$, $R^3$, $R^4$, $R^5$, $R^6$, $R^7$ or $R^8$, they may be the same or different at each occurrence.

$X^a$ and $X^b$ each represent a single bond or a group represented by —$CR^{11}R^{12}$—$CR^{13}R^{14}$—, provided that one of $X^a$ and $X^b$ is a single bond, and the other is a group represented by —$CR^{11}R^{12}$—$CR^{13}R^{14}$—, wherein $R^{11}$, $R^{12}$, $R^{13}$ and $R^{14}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent, provided that $R^{11}$ and $R^{12}$, $R^{13}$ and $R^{14}$, $R^{11}$ and $R^{13}$, and $R^{12}$ and $R^{14}$ each may be combined together to form a ring together with the atoms to which they are attached. When there are a plurality of $R^{11}$, $R^{12}$, $R^{13}$ or $R^{14}$, they may be the same or different at each occurrence. At least one selected from the group consisting of $R^{11}$, $R^{12}$, $R^{13}$ and $R^{14}$ is an alkyl group, a cycloalkyl group, an alkoxy group, a cycloalkoxy group, an aryl group, an aryloxy group, a monovalent heterocyclic group or a halogen atom.

Ring A represents a heteroaromatic ring, the heteroaromatic ring optionally having a substituent, provided that when there are a plurality of ring A, they may be the same or different.

$A^1$-$G^1$-$A^2$ represents an anionic bidentate ligand, wherein $A^1$ and $A^2$ each independently represent a carbon atom, an oxygen atom or a nitrogen atom, the foregoing atoms each optionally being an atom constituting a ring. $G^1$ represents a single bond or an atomic group constituting the bidentate ligand together with $A^1$ and $A^2$. When there are a plurality of $A^1$-$G^1$-$A^2$, they may be the same or different.]

[2] The metal complex according to [1], represented by the following formula (1-1), (1-2) or (2-1):

[Chemical Formula 3]

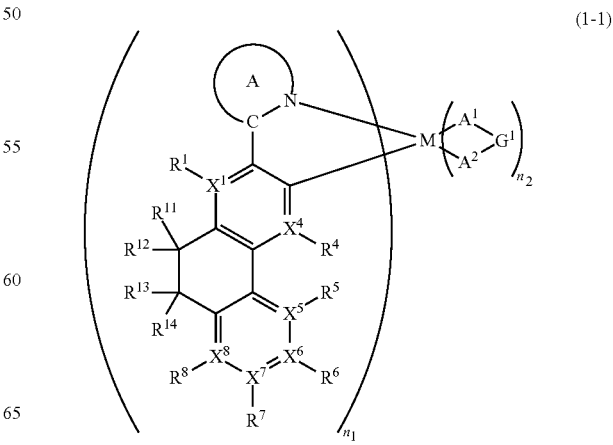

-continued (1-2)

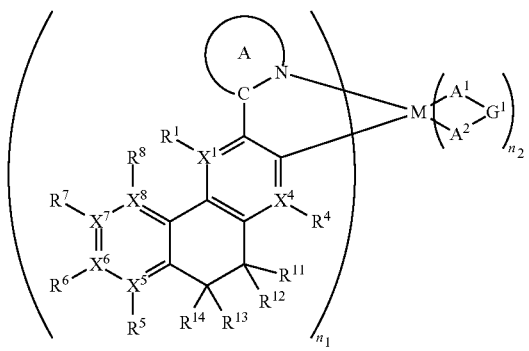

(2-1)

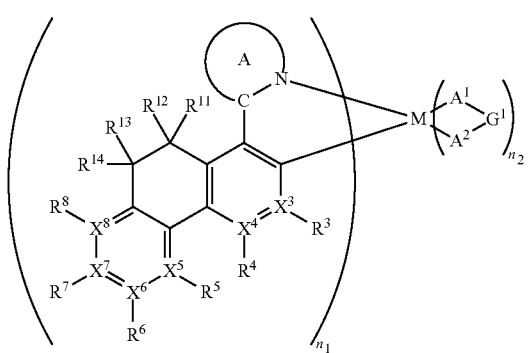

[wherein, M, $n_1$, $n_2$, $X^1$, $X^3$, $X^4$, $X^5$, $X^6$, $X^7$, $X^8$, $R^1$, $R^3$, $R^4$, $R^5$, $R^6$, $R^7$, $R^8$, $R^{11}$, $R^{12}$, $R^{13}$, $R^{14}$, ring A and $A^1$-$G^1$-$A^2$ are as defined above.]

[3] The metal complex according to [1] or [2], wherein $R^{11}$, $R^{12}$, $R^{13}$ and $R^{14}$ are each an alkyl group optionally having a substituent.

[4] The metal complex according to [3], wherein $R^{11}$ and $R^{13}$ are combined to form a zing together with the atoms to which they are attached, and $R^{12}$ and $R^{14}$ are combined to form a ring together with the atoms to which they are attached.

[5] The metal complex according to [4], represented by the following formula (1-3), (1-4) or (2-3):

[Chemical Formula 4]

(1-3)

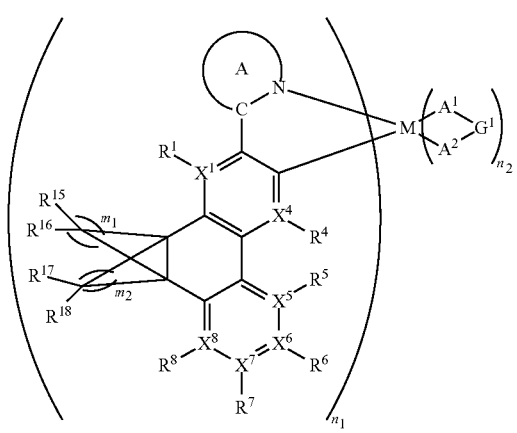

-continued (1-4)

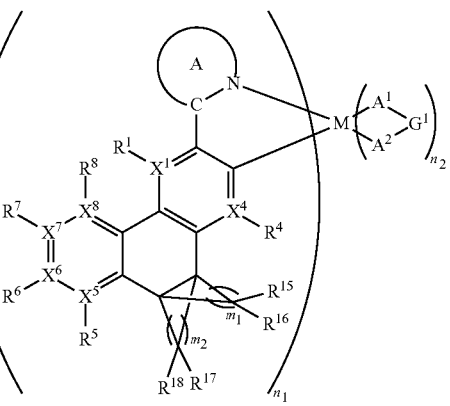

(2-3)

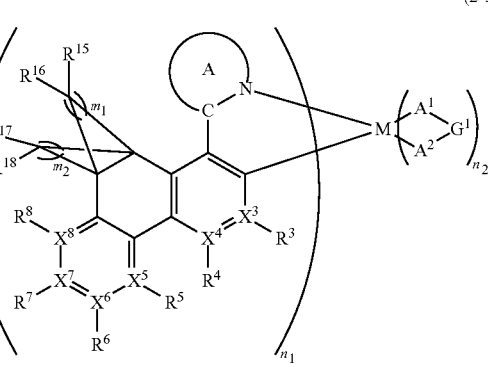

[wherein,

M, $n_1$, $n_2$, $X^1$, $X^3$, $X^4$, $X^5$, $X^6$, $X^7$, $X^8$, $R^1$, $R^3$, $R^4$, $R^5$, $R^6$, $R^7$, $R^8$, ring A and $A^1$-$G^1$-$A^2$ are as defined above.

$m_1$ and $m_2$ each independently represent an integer of 1 to 5. When there are a plurality of $m_1$ or $m_2$, they may be the same or different at each occurrence.

$R^{15}$, $R^{16}$, $R^{17}$ and $R^{18}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent. When there are a plurality of $R^{15}$, $R^{16}$, $R^{17}$ or $R^{18}$, they may be the same or different at each occurrence.]

[6] The metal complex according to [5], wherein ms and $m_2$ are each 3 or 4.

[7] The metal complex according to any one of [1] to [6], wherein $X^1$, $X^2$, $X^3$, $X^4$, $X^5$, $X^6$, $X^7$ and $X^8$ are each a carbon atom.

[8] The metal complex according to any one of [1] to [7], wherein ring A is a pyridine ring optionally having a substituent, a pyrimidine ring optionally having a substituent, a quinoline ring optionally having a substituent, an isoquinoline ring optionally having a substituent, an imidazole ring optionally having a substituent or a triazole ring optionally having a substituent.

The metal complex according to any one of [1] to [8], satisfying at least one of the following requirements (A), (B) and (C):

(A) ring A has an alkyl group, a cycloalkyl group, an aryl group or a monovalent heterocyclic group, as a substituent, (B) $R^1$, $R^2$, $R^3$, $R^4$, $R^5$ and $R^8$ are each a hydrogen atom, an alkyl group, a cycloalkyl group, an aryl group or a monovalent heterocyclic group, (C) $R^6$ and $R^7$ are each a hydrogen atom, an alkyl group, a cycloalkyl group, an aryl group, a monovalent heterocyclic group or a halogen atom.

[10] The metal complex according to any one of [1] to [8], wherein ring A has a group represented by the following formula (D-A) or (D-B) as a substituent:

[Chemical Formula 5]

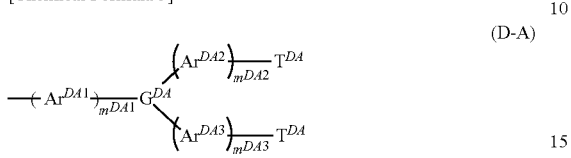

(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, the foregoing groups each optionally having a substituent.

$Ar^{DA1}$, $Ar^{DA2}$ and $Ar^{DA3}$ each independently represent an arylene group or a divalent heterocyclic group, the foregoing groups each optionally having a substituent. When there are a plurality of $Ar^{DA1}$, $Ar^{DA2}$ or $Ar^{DA3}$, they may be the same or different at each occurrence.

$T^{DA}$ represents an aryl group or a monovalent heterocyclic group, the foregoing groups each optionally having a substituent. The plurality of $T^{DA}$ may be the same or different.]

[Chemical Formula 6]

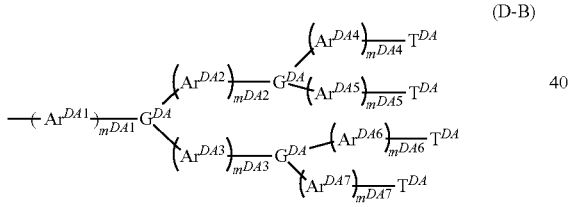

(D-B)

[wherein, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, the foregoing groups each optionally having a substituent. The plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, the foregoing groups each optionally having a substituent. When there are a plurality of $Ar^{DA1}$, $Ar^{DA2}$, $Ar^{DA3}$, $Ar^{DA4}$, $Ar^{DA5}$, $Ar^{DA6}$ or $Ar^{DA7}$, they may be the same or different at each occurrence.

$T^{DA}$ represents an aryl group or a monovalent heterocyclic group, the foregoing groups each optionally having a substituent. The plurality of TDA may be the same or different.].

[11] The metal complex according to [10], wherein the group represented by the formula (D-A) is a group represented by the following formula (D-A1), (D-A2) or (D-A3):

[Chemical Formula 7]

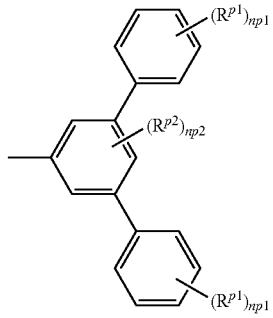

(D-A1)

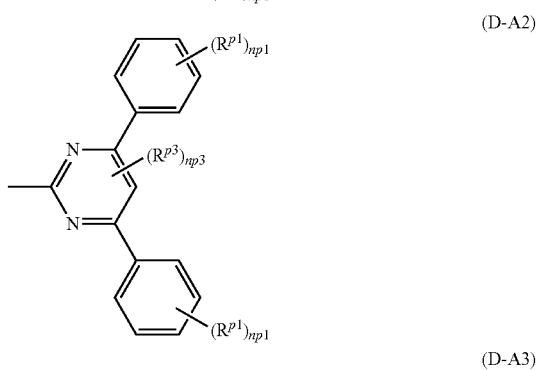

(D-A2)

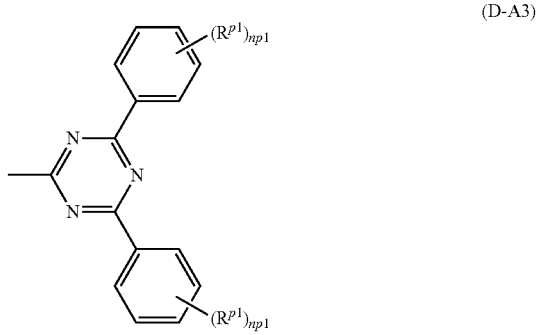

(D-A3)

[wherein, $R^{p1}$, $R^{p2}$ and $R^{p3}$ each independently represent an alkyl group, a cycloalkyl group, an alkoxy group, a cycloalkoxy group or a halogen atom. When there are a plurality of $R^{p1}$ or $R^{p2}$, they may be the same or different at each occurrence.

np1 represents an integer of 0 to 5, np2 represents an integer of 0 to 3, and np3 represents 0 or 1. The plurality of np1 may be the same or different.]

[12] The metal complex according to any one of [1] to [11], wherein M is an iridium atom, $n_1$ is 3, and $n_2$ is 0.

[13] A composition comprising:

the metal complex according to any one of [1) to (12], and a polymer compound comprising a constitutional unit represented by the following formula (Y):

[Chemical Formula 8]

$$\dashv Ar^{Y1} \dashv$$ (Y)

[wherein, $Ar^{Y1}$ represents an arylene group, a divalent heterocyclic group, or a divalent group in which at least one arylene group and at least one divalent heterocyclic group are bonded directly to each other, the foregoing groups each optionally having a substituent.].

[14] A composition comprising:
the metal complex according to any one of [1] to [13], and at least one material selected from the group consisting of a hole transporting material, a hole injection material, an electron transporting material, an electron injection material, a light emitting material, an antioxidant and a solvent.

[15] A light emitting device produced by using the metal complex according to any one of [1] to [13].

Effect of the Invention

The present invention can provide a metal complex showing excellent quantum yield and excellent in the full width at half maximum of an emission spectrum. Further, according to the present invention can provide a composition containing the metal complex and a light emitting device produced by using the metal complex. Because the metal complex of the present invention is excellent in quantum yield, a light emitting device produced by using the metal complex shall be excellent in external quantum efficiency. Additionally, because the metal complex of the present invention is excellent in the full width at half maximum of an emission spectrum, when a light emitting device produced by using the metal complex is used together with a color filter and when the microcavity of a light emitting device produced by using the metal complex is controlled, its external quantum efficiency shall be further excellent.

BRIEF EXPLANATION OF DRAWINGS

FIG. 1 is shows the emission spectra of a metal complex M1, a metal complex M2 and a metal complex CM1.

FIG. 2 shows the emission spectrum of a metal complex M3.

FIG. 3 shows the emission spectra of a metal complex M4 and a metal complex M5.

FIG. 4 shows the emission spectrum of a metal complex M6.

FIG. 5 is shows the transmission spectrum of color filters A, B and C used in examples.

MODES FOR CARRYING OUT THE INVENTION

Suitable embodiments of the present invention will be illustrated in detail below.

Explanation of Common Term

Terms commonly used in the present specification described below have the following meanings unless otherwise stated.

Me represents a methyl group, Et represents an ethyl group, Bu represents a butyl group, i-Pr represents an isopropyl group, and t-Bu represents a tert-butyl group.

In the present specification, the hydrogen atom may be a heavy hydrogen atom.

In the present specification, a solid line representing a bond to a central metal in a structural formula representing a metal complex denotes a coordinate bond or a covalent bond.

"Polymer compound" denotes a polymer having molecular weight distribution and having a polystyrene-equivalent number average molecular weight of $1\times10^3$ to $1\times10^6$. The total amount of constitutional units contained in the polymer compound is 100 mol %.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes groups bonding to an aryl group or a monovalent heterocyclic group via a carbon-carbon bond.

"Low molecular weight compound" denotes a compound having no molecular weight distribution and having a molecular weight of $1\times10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The number of carbon atoms of a cycloalkyl group is, not including the number of carbon atoms of a substituent, usually 3 to 50, preferably 3 to 30, more preferably 4 to 20.

The alkyl group and cycloalkyl group optionally have a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a 1,1,3,3,-tetramethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group, a dodecyl group and a cyclohexyl group, and groups obtained by substituting a hydrogen atom in the foregoing groups with an alkyl group, a cycloalkyl group, an alkoxy group, a cycloalkoxy group, an aryl group, a fluorine atom or the like, and the alkyl group and cycloalkyl group having a substituent include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexylphenyl) propyl group, a 6-ethyloxyhexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in the foregoing groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The number of carbon atoms of "Cycloalkoxy group" is, not including the number of carbon atoms of a substituent, usually 3 to 40, preferably 4 to 10.

The alkoxy group and cycloalkoxy group optionally have a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group and a lauryloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in the foregoing groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from a heteroaromatic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidinyl group, a quinolinyl group, an isoquinolinyl group, a pyrimidinyl group, a triazinyl group, and groups obtained by substituting a hydrogen atom in the foregoing groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, the foregoing groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and the foregoing groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and the foregoing groups having a substituent, preferably, groups represented by the formulae (A-1) to (A-20). The arylene group includes groups obtained by linking a plurality of the foregoing groups.

[Chemical Formula 9]

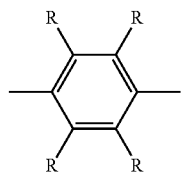

(A-1)

-continued
(A-2) 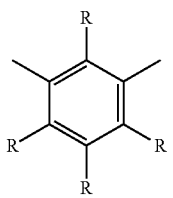
(A-3) 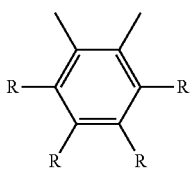
(A-4) 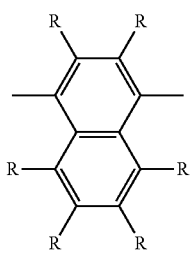
(A-5) 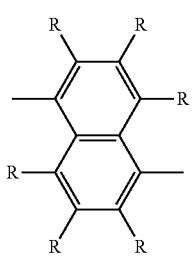
(A-6) 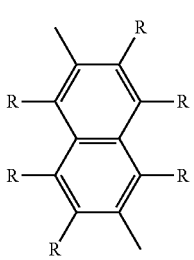
[Chemical Formula 10]
(A-7) 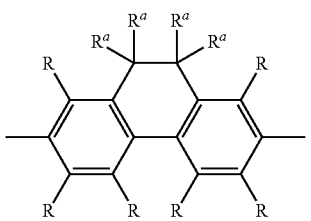
(A-8) 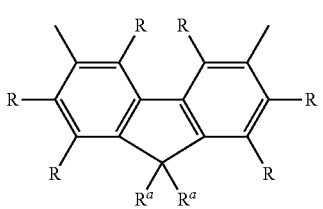
(A-9) 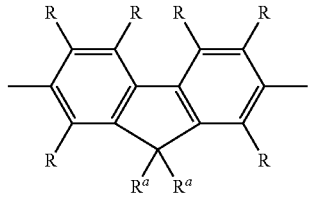
(A-10) 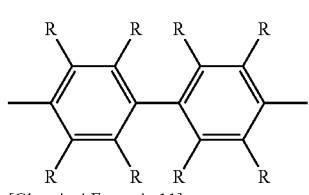
[Chemical Formula 11]
(A-11) 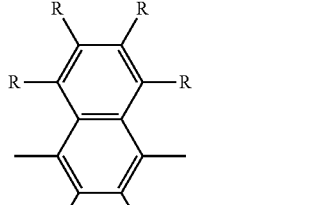
(A-12) 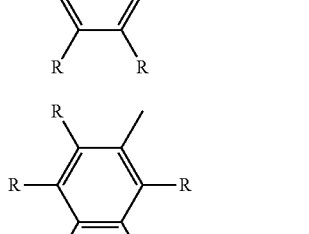
(A-13) 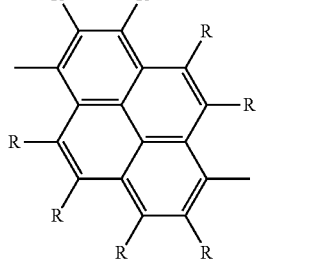
(A-14) 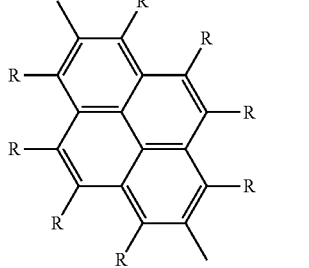

(A-15)
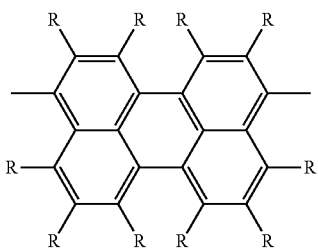
[Chemical Formula 12]

(A-16)
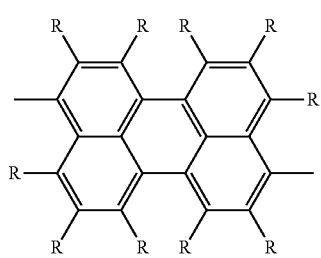

(A-17)
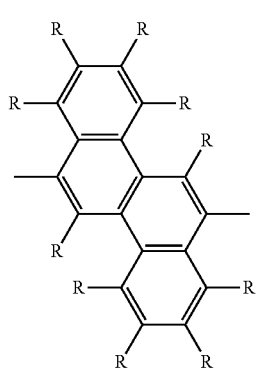

(A-18)
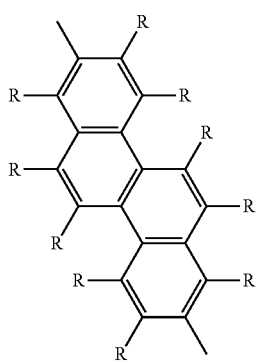

(A-19)
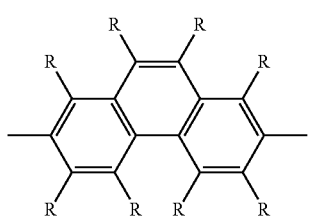

(A-20)
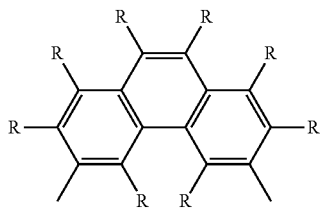

[wherein, R and $R^a$ each independently represent a hydrogen atom, an alkyl group, a cycloalkyl group, an aryl group or a monovalent heterocyclic group. The plurality of R and $R^a$ each may be the same or different, and adjacent $R^a$s may be combined together to form a ring together with the atoms to which they are attached.]

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of the foregoing groups.

[Chemical Formula 13]

(AA-1)
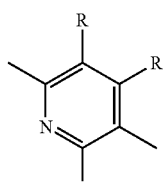

(AA-2)
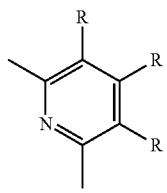

(AA-3)
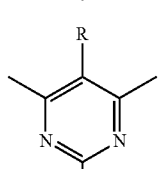

(AA-4)
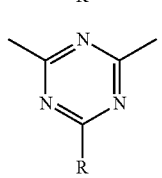

-continued
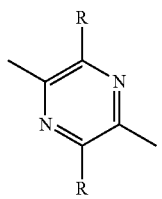 (AA-5)
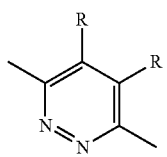 (AA-6)
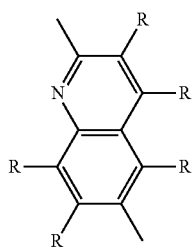 (AA-7)
[Chemical Formula 14]
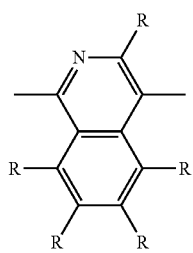 (AA-8)
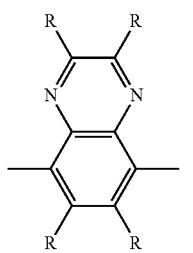 (AA-9)
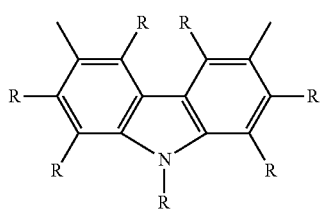 (AA-10)
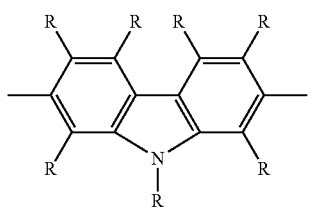 (AA-11)
-continued
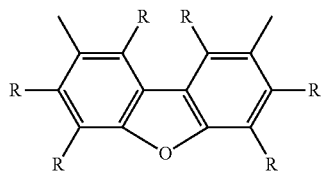 (AA-12)
[Chemical Formula 15]
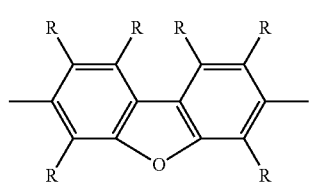 (AA-13)
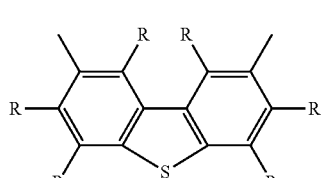 (AA-14)
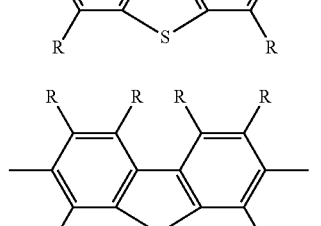 (AA-15)
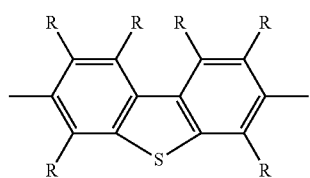 (AA-16)
[Chemical Formula 16]
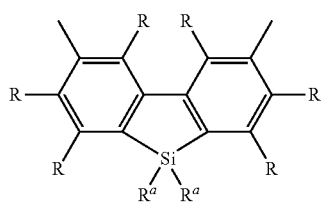 (AA-17)
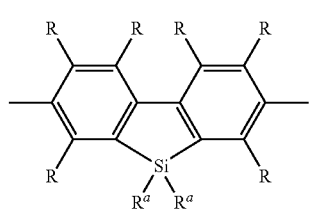 (AA-18)
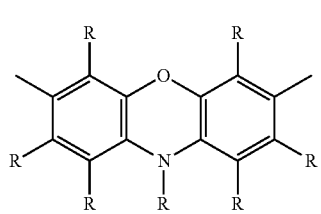 (AA-19)
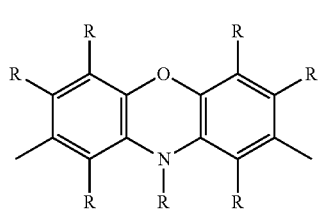

(AA-20)
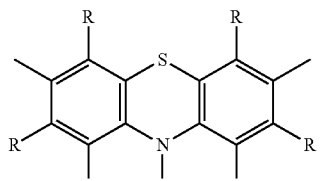

[Chemical Formula 17]

(AA-21)
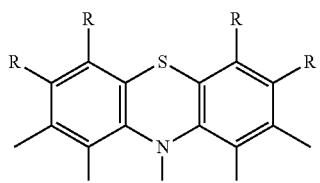

(AA-22)
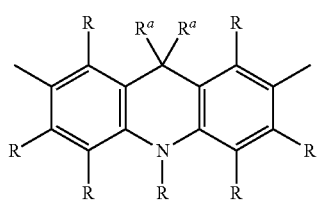

(AA-23)

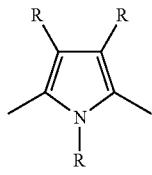
(AA-24)

[Chemical Formula 18]

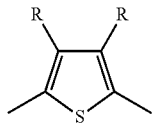
(AA-25)

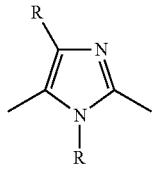
(AA-26)

(AA-27)

(AA-28)
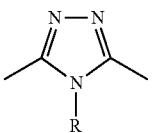

(AA-29)
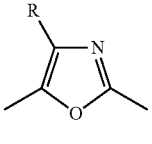

(AA-30)
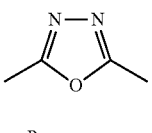

(AA-31)
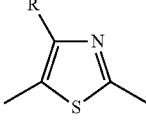

(AA-32)
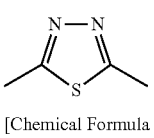

[Chemical Formula 19]

(AA-33)
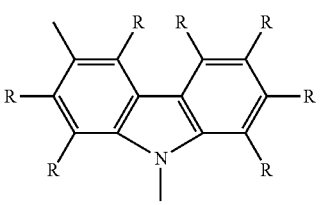

(AA-34)
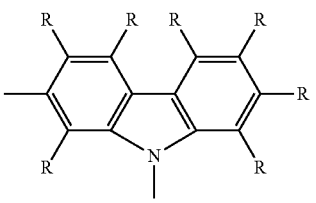

[wherein, R and $R^a$ are as defined above.]

"Cross-linkable group" is a group capable of forming a new bond by being subjected to a heating treatment, an ultraviolet irradiation treatment, a radical reaction and the like, and is preferably a group represented by the formula (B-1), (B-2), (B-3), (B-4), (B-5), (B-6), (B-7), (B-8), (B-9), (B-10), (B-11), (B-12), (B-13), (B-14), (B-15), (B-16) or (B-17).

[Chemical Formula 20]

(B-1)

(B-2)
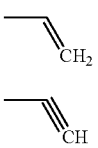

-continued (B-3) 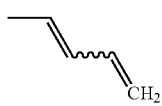

(B-4) 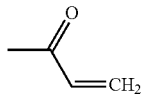

(B-5) 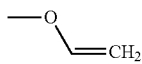

(B-6) 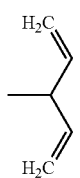

(B-7) 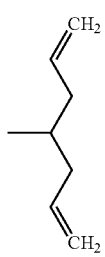

(B-8) 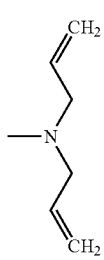

(B-9) 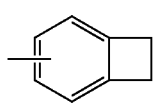

(B-10) 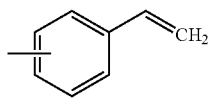

(B-11) 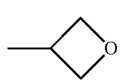

(B-12) 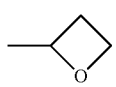

(B-13) 

(B-14) 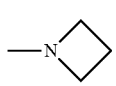

(B-15) 

(B-16) 

—N$_3$ (B-17) 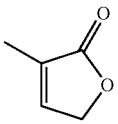

[wherein, the foregoing groups each optionally have a substituent.]

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

"Dendron" is a group having a regular dendritic branched structure having a branching point at an atom or ring (a dendrimer structure). A compound having a dendron as a partial structure (called a dendrimer in some cases) includes, for example, structures described in literatures such as Ser. No. 02/067,343, JP-A No. 2003-231692, NO 2003/079736, NO 2006/097717 and the like. Dendron is preferably a group represented by the formula (D-A) or a group represented by the formula (D-B).

$m^{DA1}$, $m^{DA2}$, $m^{DA3}$, $m^{DA4}$, $m^{DA5}$, $m^{DA6}$ and $m^{DA7}$ are usually an integer of 10 or less, preferably an integer of 5 or less, more preferably 0 or 1, further preferably 0. It is preferable that $m^{DA1}$, $m^{DA2}$, $m^{DA3}$, $m^{DA4}$, $m^{DA5}$, $m^{DA6}$ and $m^{DA7}$ are the same integer.

$G^{DA}$ is preferably a group represented by the formulae (GDA-11) to (GDA-15), and the foregoing groups each optionally have a substituent.

[Chemical Formula 21]

(GDA-11)

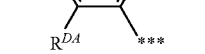

(GDA-12)

(GDA-13)

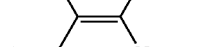

-continued (GDA-14)

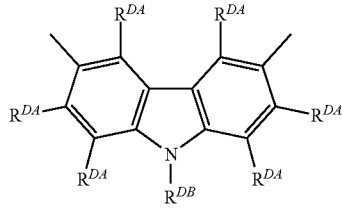

(GDA-15)

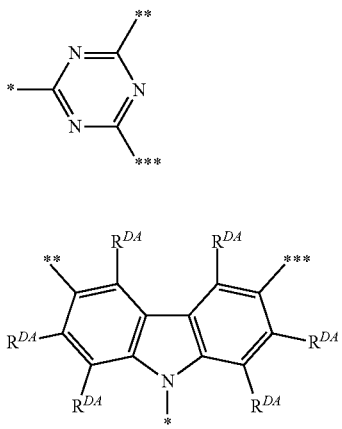

[wherein,

* represents a linkage to $Ar^{DA1}$ in the formula (D-A), $Ar^{DA1}$ in the formula (D-B), $Ar^{DA2}$ in the formula (D-B) or $Ar^{DA3}$ in the formula (D-B).

** represents a linkage to $Ar^{DA2}$ in the formula (D-A), $Ar^{DA2}$ in the formula (D-B), $Ar^{DA4}$ in the formula (D-B) or $Ar^{DA6}$ in the formula (D-B).

*** represents a linkage to $Ar^{DA3}$ in the formula (D-A), $Ar^{DA3}$ in the formula (D-B), $Ar^{DA5}$ in the formula (D-B) or $Ar^{DA7}$ in the formula (D-B).

$R^{DA}$ represents a hydrogen atom, an alkyl group, a cycloalkyl group, an alkoxy group, a cycloalkoxy group, an aryl group or a monovalent heterocyclic group, the foregoing groups each optionally having a substituent. When there are a plurality of $R^{DA}$, they may be the same or different.]

$R^{DA}$ is preferably a hydrogen atom, an alkyl group, a cycloalkyl group, an alkoxy group or a cycloalkoxy group, more preferably a hydrogen atom, an alkyl group or cycloalkyl group, the foregoing groups each optionally have a substituent.

It is preferable that $Ar^{DA1}$, $Ar^{DA2}$, $Ar^{DA3}$, $Ar^{DA4}$, $Ar^{DA5}$, $Ar^{DA6}$ and $Ar^{DA7}$ are each groups represented by the formulae (ArDA-1) to (ArDA-3).

[Chemical Formula 22]

(ArDA-1)

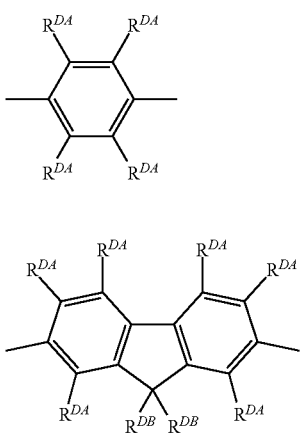

(ArDA-2)

(ArDA-3)

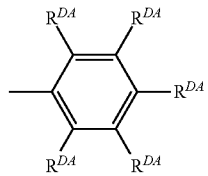

[wherein, $R^{DA}$ represents the same meaning as described above.

$R^{DB}$ represents a hydrogen atom, an alkyl group, a cycloalkyl group, an aryl group or a monovalent heterocyclic group, the foregoing groups each optionally having a substituent. When there are a plurality of $R^{DB}$, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group.

$T^{DA}$ is preferably groups represented by the formulae (TDA-1) to (TDA-3).

[Chemical Formula 23]

(TDA-1)

(TDA-2)

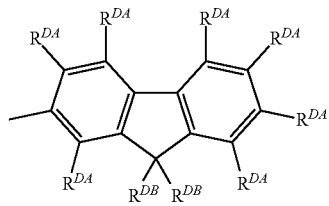

(TDA-3)

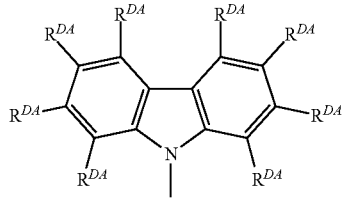

[wherein, $R^{DA}$ and $R^{DB}$ represent the same meaning described above.]

The group represented by the formula (D-A) is preferably a group represented by the formulae (D-A1) to (D-A3).

The group represented by the formula (D-B) is preferably a group represented by the formulae (D-B1) to (D-B3).

[Chemical Formula 24]

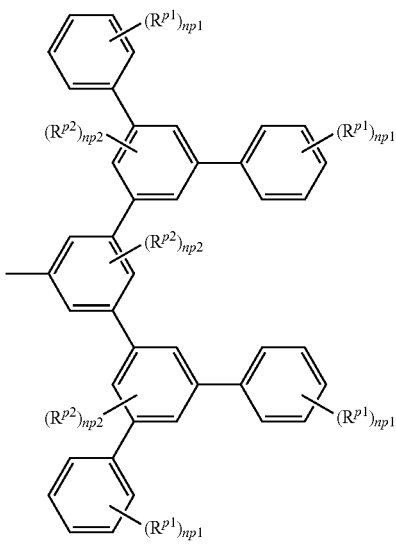
(D-B1)

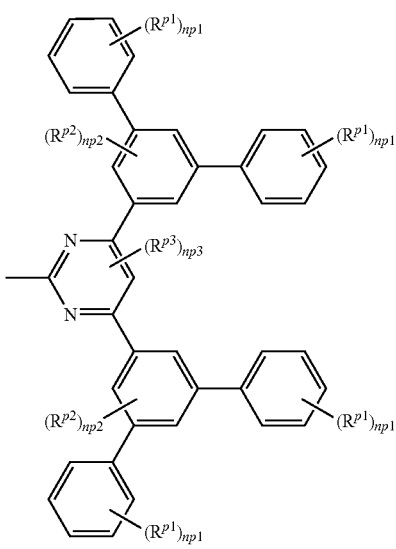
(D-B2)

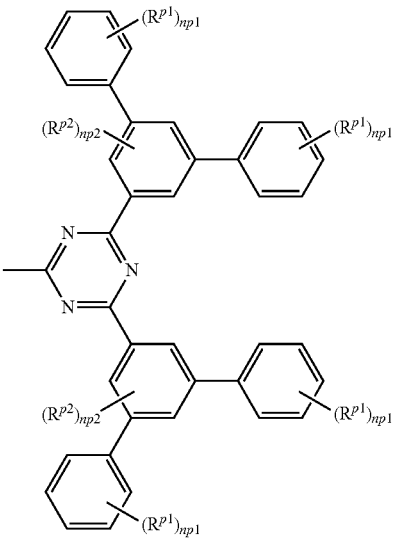
(D-B3)

[wherein, $R^{p1}$, $R^{p2}$ and $R^{p3}$ each independently represent an alkyl group, a cycloalkyl group, an alkoxy group, a cycloalkoxy group or a halogen atom. When there are a plurality of $R^{p1}$ or $R^{p2}$, they may be the same or different at each occurrence.

np1 represents an integer of 0 to 5, np2 represents an integer of 0 to 3, and np3 represents 0 or 1. The plurality of np1 may be the same or different.]

np1 is preferably 0 or 1, more preferably 1. np2 is preferably 0 or 1, more preferably 0. np3 is preferably 0.

$R^{p1}$, $R^{p2}$ and $R^{p3}$ are preferably an alkyl group or a cycloalkyl group.

<Metal Complex>

Next, the metal complex of the present invention will be illustrated. The metal complex of the present invention is represented by the formula (1), the formula (2) or the formula (3).

In the formula (1), the formula (2) and the formula (3), M is preferably an iridium atom, because a light emitting device using the metal complex of the present invention is excellent in the luminance life.

In the formula (1), the formula (2) and the formula (3), $n_2$ is preferably 0, because the metal complex of the present invention is more excellent in the quantum yield and because synthesis of the metal complex of the present invention is easy.

In the formula (1), the formula (2) and the formula (3), the anionic bidentate ligand represented by $A^1$-$G^1$-$A^2$ includes, for example, ligands shown below.

[Chemical Formula 25]

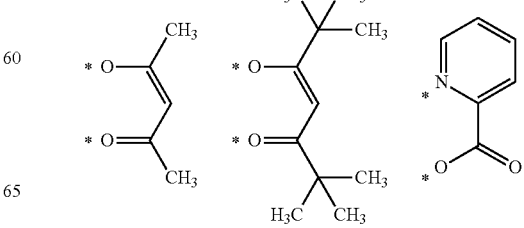

27
-continued
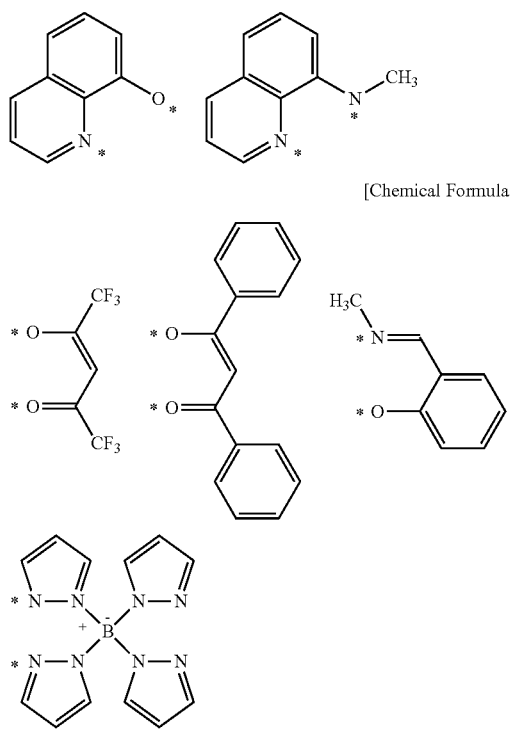
[Chemical Formula 26]
[wherein, * represents a position linking to an iridium atom or a platinum atom.]
In the formula (1), the formula (2) and the formula (3), the anionic bidentate ligand represented by $A^1$-$G^1$-$A^2$ may be a ligands represented by the following formulae.
[Chemical Formula 27]
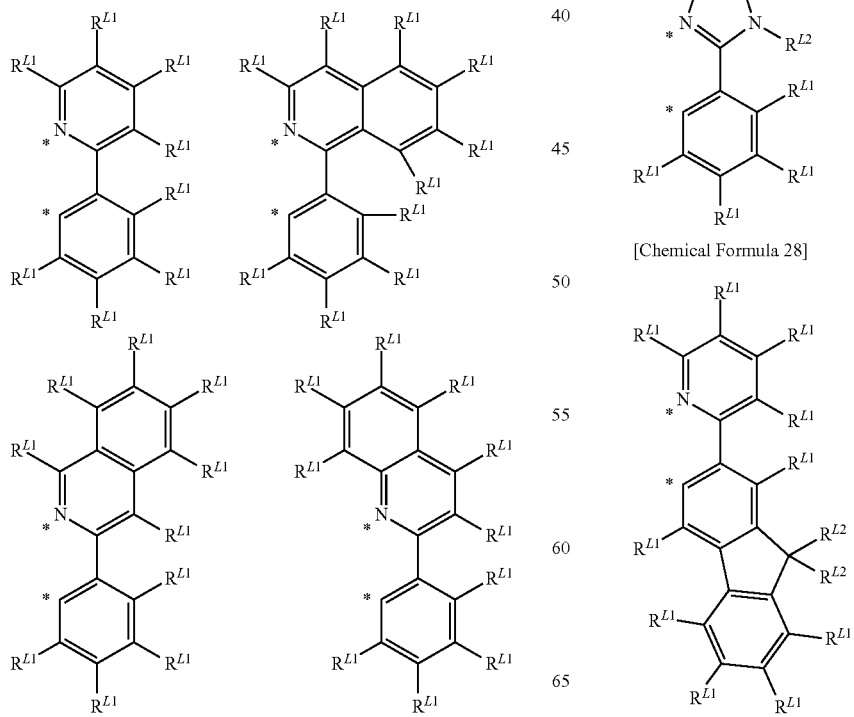
28
-continued
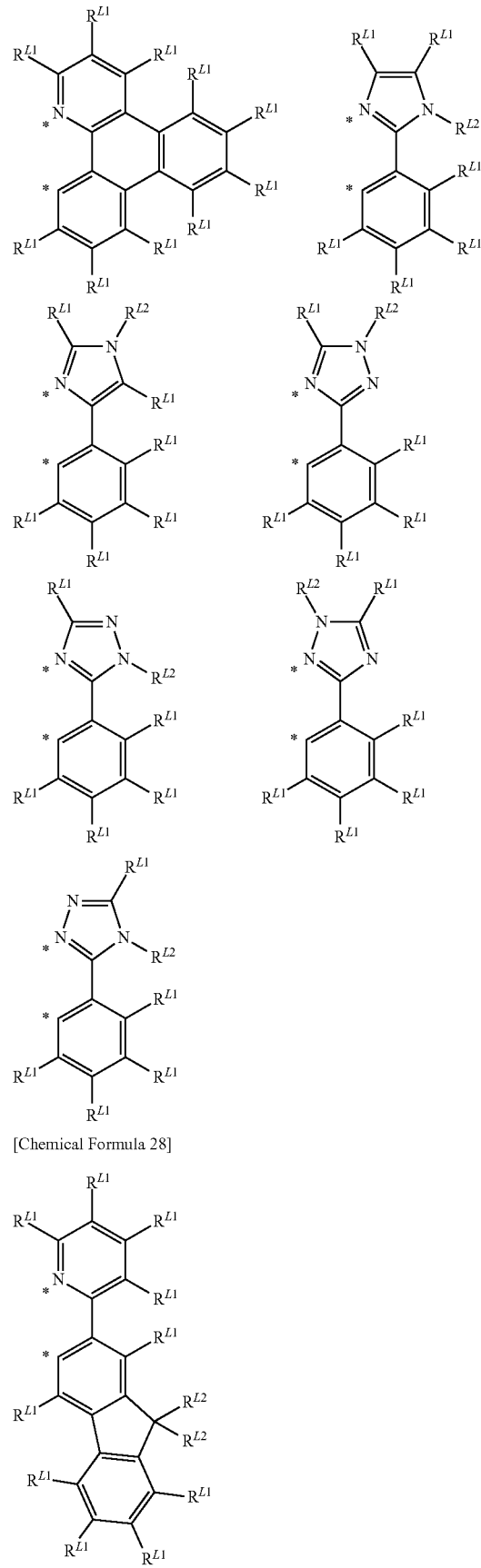
[Chemical Formula 28]

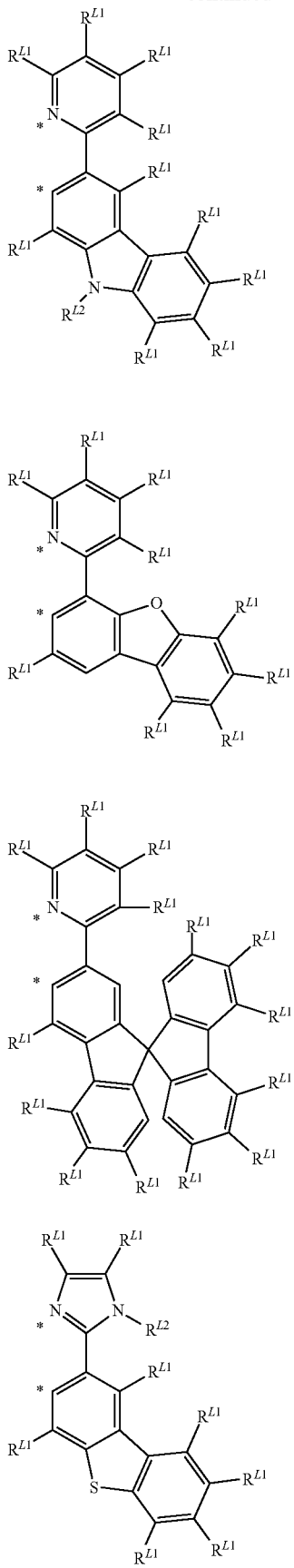

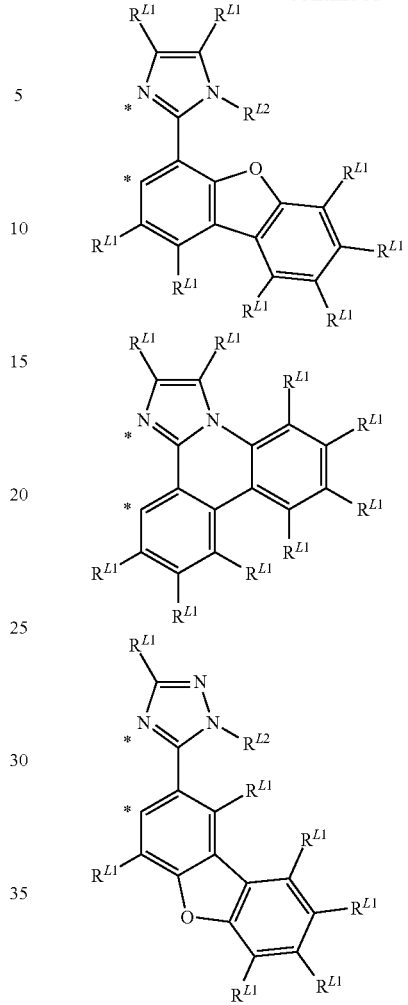

[wherein,
* represents a position linking to an iridium atom or a platinum atom.

$R^{L1}$ represents a hydrogen atom, an alkyl group, a cycloalkyl group, an aryl group, a monovalent heterocyclic group or a halogen atom, the foregoing groups each optionally having a substituent. The plurality of $R^{L1}$ may be the same or different.

$R^{L2}$ represents an alkyl group, a cycloalkyl group, an aryl group, a monovalent heterocyclic group or a halogen atom, the foregoing groups each optionally having a substituent. When there are a plurality of $R^{L2}$, they may be the same or different.]

In the formula (1), the formula (2) and the formula (3), $X^1$, $X^2$, $X^3$, $X^4$, $X^5$, $X^6$, $X^7$ and $X^8$ each represent preferably a carbon atom, because synthesis of the metal complex of the present invention is easy.

In the formula (1), the formula (2) and the formula (3), $R^1$, $R^2$, $R^3$, $R^4$, $R^5$ and $R^6$ each represent preferably a hydrogen atom, an alkyl group, a cycloalkyl group, an aryl group or a monovalent heterocyclic group, more preferably a hydrogen atom, an alkyl group, a cycloalkyl group or an aryl group, further preferably a hydrogen atom or an alkyl group, particularly preferably a hydrogen atom, because synthesis of the metal complex of the present invention is easy.

In the formula (1), the formula (2) and the formula (3), $R^6$ and $R^7$ each represent preferably a hydrogen atom, an alkyl group, a cycloalkyl group, an aryl group, a monovalent heterocyclic group or a halogen atom, more preferably a hydrogen atom, an alkyl group, a cycloalkyl group, an aryl group or a halogen atom, further preferably a hydrogen atom, an alkyl group, a cycloalkyl group or a halogen atom, particularly preferably a hydrogen atom or an alkyl group, because the solubility of the metal complex of the present invention in a solvent and the film formability thereof are excellent.

In the formula (1), the formula (2) and the formula (3), it is preferable that $R^1$ and $R^8$ each represent a hydrogen atom or an alkyl group, it is more preferable that $R^1$, $R^2$ and $R^8$ each represent a hydrogen atom or an alkyl group, $R^1$, $R^6$ and $R^8$ each represent a hydrogen atom or an alkyl group, or $R^1$, $R^7$ and $R^8$ each represent a hydrogen atom or an alkyl group, it is further preferable that $R^1$, $R^2$, $R^6$ and $R^8$ each represent a hydrogen atom or an alkyl group, or $R^1$, $R^2$, $R^7$ and $R^8$ each represent a hydrogen atom or an alkyl group, it is particularly preferable that $R^1$, $R^2$, $R^3$, $R^4$, $R^5$, $R^6$, $R^7$ and $R^8$ each represent a hydrogen atom or an alkyl group, because the luminance life of a light emitting device using the metal complex of the present invention is excellent.

In the formula (1), the formula (2) and the formula (3), ring A represents preferably a pyridine ring optionally having a substituent, a pyrimidine ring optionally having a substituent, a quinoline ring optionally having a substituent, an isoquinoline ring optionally having a substituent, an imidazole ring optionally having a substituent or a triazole ring optionally having a substituent, more preferably a pyridine ring optionally having a substituent, a pyrimidine ring optionally having a substituent, an imidazole ring optionally having a substituent or a triazole ring optionally having a substituent, further preferably a pyridine ring optionally having a substituent, an imidazole ring optionally having a substituent or a triazole ring optionally having a substituent, particularly preferably a pyridine ring optionally having a substituent or a triazole ring optionally having a substituent, because the luminance life of a light emitting device using the metal complex of the present invention is excellent. When ring A has a plurality of substituents, they may be the same or different, and may be combined together to form a ring together with the atoms to which they are attached.

When ring A has a substituent in the formula (1), the formula (2) and the formula (3), the substituent is preferably an alkyl group, a cycloalkyl group, an aryl group, a monovalent heterocyclic group, a substituted amino group or a halogen atom, more preferably an alkyl group, a cycloalkyl group, an aryl group or a monovalent heterocyclic group, further preferably an alkyl group, a cycloalkyl group or an aryl group, because the metal complex of the present invention is excellent in the solubility in a solvent and the film formability. It is preferable that the aryl group, the monovalent heterocyclic group and the substituted amino group are dendrons.

When ring A has a substituent in the formula (1), the formula (2) and the formula (3), at least one of the substituents is preferably a dendron, more preferably a group represented by the formula (D-A) or the formula (D-B), further preferably a group represented by the formula (D-A), particularly preferably a group represented by the formula (D-A1), (D-A2) or (D-A3), especially preferably a group represented by the formula (D-A3), because the quantum yield of the metal complex of the present invention is more excellent.

In the formula (1), the formula (2) and the formula (3), the aromatic heterocyclic ring represented by ring A includes, for example, aromatic heterocyclic rings represented by the following formulae (E-1) to (E-15) and the following formulae (F-1) to (F-15). Of them, aromatic heterocyclic rings represented by the formulae (E-1) to (E-4) or the formulae (F-1) to (F-13) are preferable, because synthesis of the metal complex of the present invention is easy, and aromatic heterocyclic rings represented by the formulae (E-1) to (E-3) or the formulae (F-2) to (F-6) are more preferable, aromatic heterocyclic rings represented by the formula (E-2), the formula (E-3) or the formula (F-6) are further preferable, one represented by the formula (E-2) is particularly preferable, because the luminance life of a light emitting device using the metal complex of the present invention is excellent.

[Chemical Formula 29]

(E-1)

(E-2)

(E-3)

(E-4)

(E-5)

(E-6)

-continued
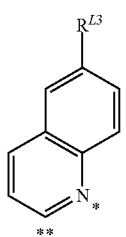 (E-7)
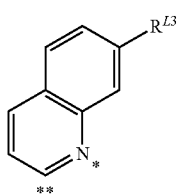 (E-8)
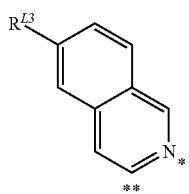 (E-9)
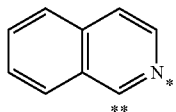 (E-10)
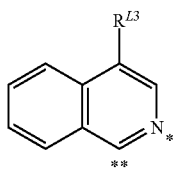 (E-11)
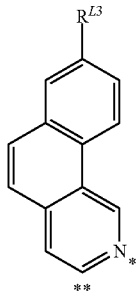 (E-12)
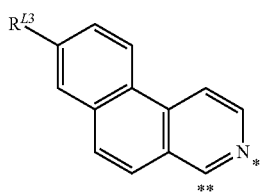 (E-13)
-continued
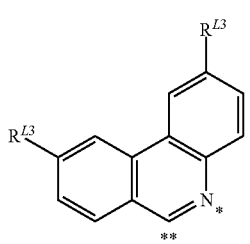 (E-14)
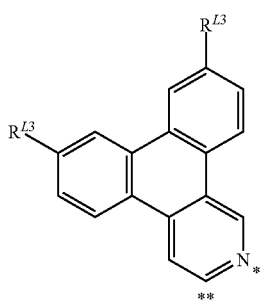 (E-15)
[Chemical Formula 30]
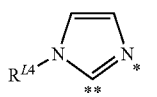 (F-1)
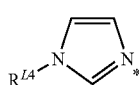 (F-2)
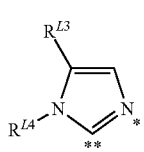 (F-3)
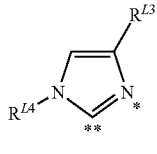 (F-4)
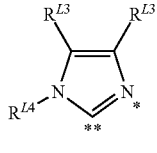 (F-5)
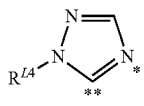 (F-6)
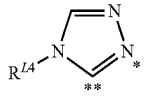 (F-7)

-continued (F-8)
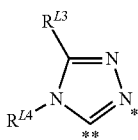

(F-9)
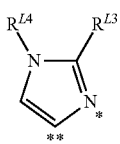

(F-10)
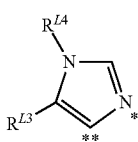

(F-11)
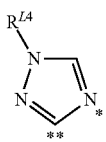

(F-12)
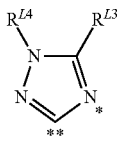

(F-13)
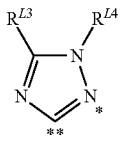

(F-14)
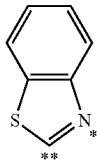

(F-15)
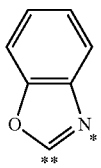

[wherein,

* represents a position linking to an iridium atom or a platinum atom.

** represents a position linking to an aromatic ring having $X^1$ and $X^4$ as a constituent atom, an aromatic ring having $X^3$ and $X^4$ as a constituent atom or an aromatic ring having $X^1$ and $X^2$ as a constituent atom.

$R^{L3}$ represents an alkyl group, a cycloalkyl group, an aryl group, a monovalent heterocyclic group, a substituted amino group or a halogen atom, the foregoing groups each optionally having a substituent. When there are a plurality of $R^{L3}$, they may be the same or different.

$R^{L4}$ represents an alkyl group, a cycloalkyl group, an aryl group, a monovalent heterocyclic group, a substituted amino group or a halogen atom, the foregoing groups each optionally having a substituent.].

In the formulae (E-1) to (E-15) and the formulae (F-1) to (F-15), $R^{L3}$ is preferably an alkyl group, an aryl group, a monovalent heterocyclic group or a substituted amino group, more preferably an aryl group, a monovalent heterocyclic group or a substituted amino group. It is preferable that the aryl group, the monovalent heterocyclic group and the substituted amino group are dendrons.

In the formulae (E-1) to (E-15) and the formulae (F-1) to (F-15), $R^{L4}$ is preferably an alkyl group, a cycloalkyl group, an aryl group or a substituted amino group, more preferably an alkyl group or an aryl group. It is preferable that the aryl group, the monovalent heterocyclic group and the substituted amino group are dendrons.

Because one of $X^a$ and $X^b$ is a single bond and the other is a group represented by $-CR^{11}R^{12}-CR^{13}R^{14}-$ in the formula (1), the formula (2) and the formula (3), the metal complex represented by the formula (1) is a metal complex represented by the formula (1-1) or the formula (1-2), the metal complex represented by the formula (2) is a metal complex represented by the formula (2-1) or the formula (2-2), and the metal complex represented by the formula (3) is a metal complex represented by the formula (3-1) or the formula (3-2).

[Chemical Formula 31]

(1-1)
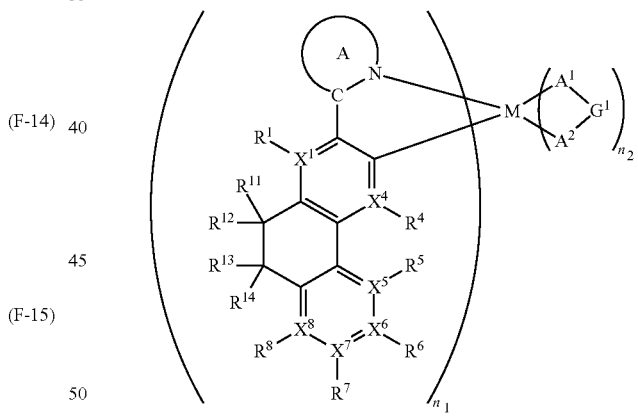

(1-2)
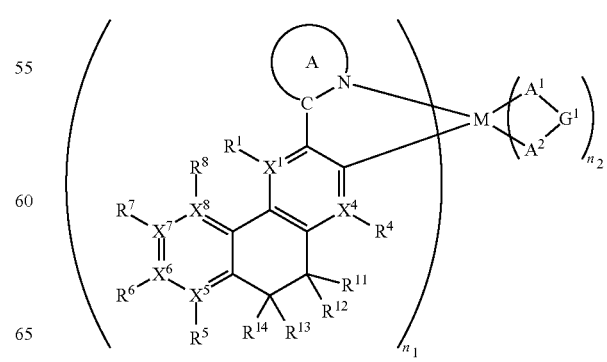

-continued

[Chemical Formula 32]

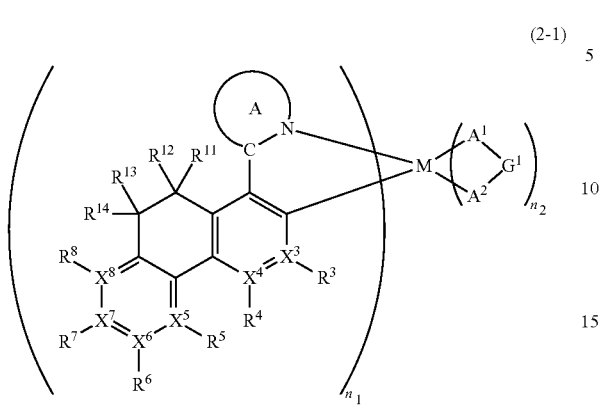

(2-1)

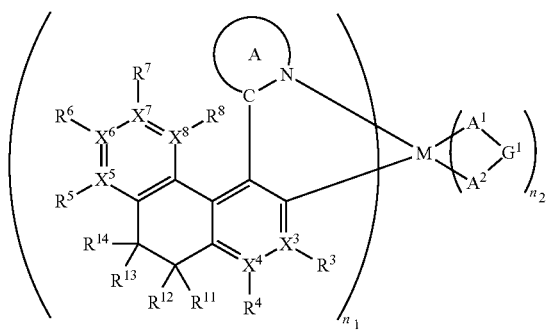

(2-2)

[Chemical Formula 33]

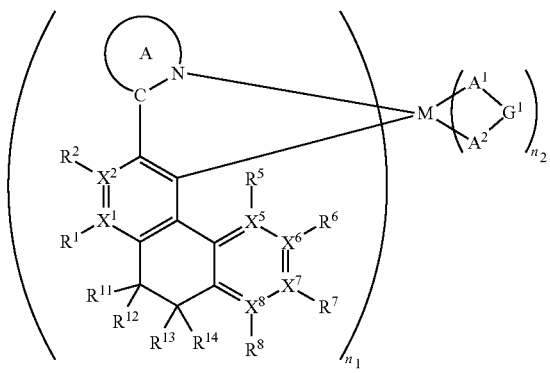

(3-1)

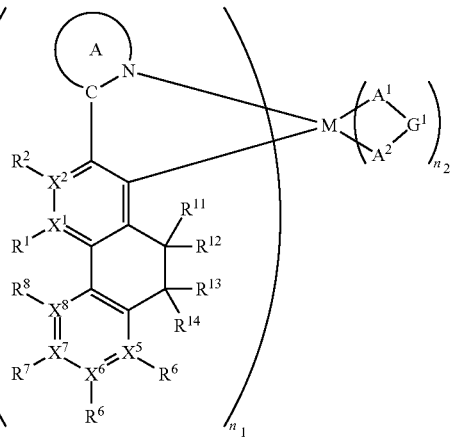

(3-2)

[wherein, M, $n_1$, $n_2$, $X^1$, $X^2$, $X^3$, $X^4$, $X^5$, $X^6$, $X^7$, $X^8$, $R^1$, $R^2$, $R^3$, $R^4$, $R^5$, $R^6$, $R^7$, $R^8$, $R^{11}$, $R^{12}$, $R^{13}$, $R^{14}$, ring A and $A^1$-$G^1$-$A^2$ are as defined above.].

Of metal complexes represented by the formula (1-1), the formula (1-2), the formula (2-1), the formula (2-2), the formula (3-1) and the formula (3-2), the preferable are metal complexes represented by the formula (1-1), the formula (1-2), the formula (2-1) or the formula (3-2), the more preferable are metal complexes represented by the formula (1-1), the formula (1-2) or the formula (2-1), the further preferable are metal complexes represented by the formula (1-1) or the formula (1-2), because synthesis of the metal complex of the present invention is easy.

In the formula (1-1), the formula (1-2), the formula (2-1), the formula (2-2), the formula (3-1) and the formula (3-2), at least one selected from the group consisting of $R^{11}$, $R^{12}$, $R^{13}$ and $R^{14}$ is an alkyl group, a cycloalkyl group, an alkoxy group, a cycloalkoxy group, an aryl group, an aryloxy group, a monovalent heterocyclic group or a halogen atom, and the more preferably is an alkyl group or an alkoxy group, the further preferably an alkyl group, because synthesis of the metal complex of the present invention is easy, and it is preferable that the foregoing groups have a substituent.

In the formula (1-1), the formula (1-2), the formula (2-1), the formula (2-2), the formula (3-1) and the formula (3-2), $R^{11}$ and $R^{12}$, $R^{13}$ and $R^{14}$, $R^{11}$ and $R^{13}$, and $R^{12}$ and $R^{14}$ each may be combined together to form a ring together with the atoms to which they are attached. The formed cyclic structure optionally has a substituent, and the substituent includes an alkyl group, a cycloalkyl group, an alkoxy group, a cycloalkoxy group, an aryl group, an aryloxy group, a monovalent heterocyclic group and a halogen atom.

In the formula (1-1), the formula (1-2), the formula (2-1), the formula (2-2), the formula (3-1) and the formula (3-2), $R^{11}$, $R^{12}$, $R^{13}$ and $R^{14}$ each represent preferably an alkyl group optionally having a substituent, and it is preferable that $R^{11}$, $R^{12}$, $R^{13}$ and $R^{14}$ each represent an alkyl group optionally having a substituent and $R^{11}$ and $R^{13}$ are combined together to form a ring together with the atoms to which they are attached and $R^{12}$ and $R^{14}$ are combined together to form a ring together with the atoms to which they are attached, because the luminance life of a light emitting device using the metal complex of the present invention is excellent.

The metal complex represented by the formula (1-1) is preferably a metal complex represented by the formula (1-3), the metal complex represented by the formula (1-2) is preferably a metal complex represented by the formula (1-4), the metal complex represented by the formula (2-1) is preferably a metal complex represented by the formula (2-3), the metal complex represented by the formula (2-2) is preferably a metal complex represented by the formula (2-4), the metal complex represented by the formula (3-1) is preferably a metal complex represented by the formula (3-3), and the metal complex represented by the formula (3-2) is preferably a metal complex represented by the formula (3-4).

[Chemical Formula 34]

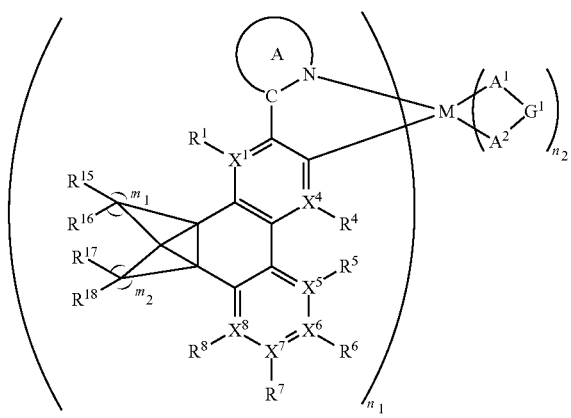

(1-3)

(1-4)

[Chemical Formula 35]

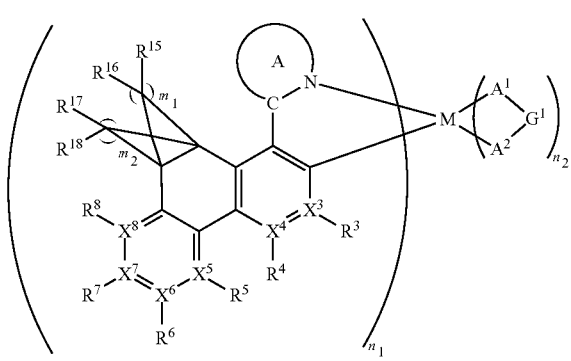

(2-3)

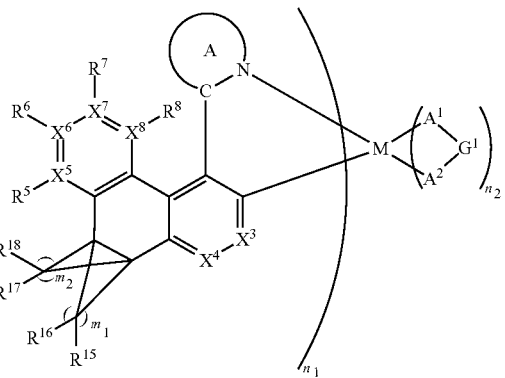

(2-4)

[Chemical Formula 36]

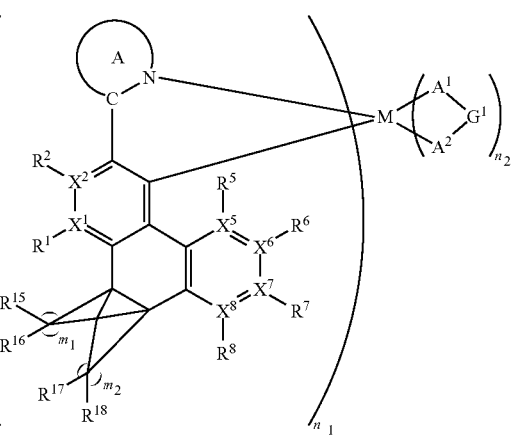

(3-3)

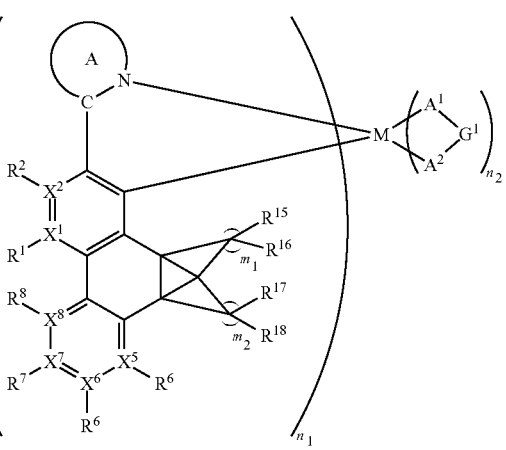

(3-4)

[wherein,

M, $n_1$, $n_2$, $X^1$, $X^2$, $X^3$, $X^4$, $X^5$, $X^6$, $X^7$, $X^8$, $R^1$, $R^2$, $R^3$, $R^4$, $R^5$, $R^6$, $R^7$, $R^8$, ring A and $A^1$-$G^1$-$A^2$ are as defined above.

$m_1$ and $m_2$ each independently represent an integer of 1 to 5. When there are a plurality of $m_1$ or $m_2$, they may be the same or different at each occurrence.

$R^{15}$, $R^{16}$, $R^{17}$ and $R^{18}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent. When there are a plurality of $R^{15}$, $R^{16}$, $R^{17}$ or $R^{18}$, they may be the same or different at each occurrence.]

Of metal complexes represented by the formula (1-3), the formula (1-4), the formula (2-3), the formula (2-4), the formula (3-3) and the formula (3-4), the preferable are metal complexes represented by the formula (1-3), the formula (1-4), the formula (2-3) or the formula (3-4), the more preferable are metal complexes represented by the formula (1-3), the formula (1-4) or the formula (2-3), the further preferable are metal complexes represented by the formula (1-3) or the formula (1-4), because synthesis of the metal complex of the present invention is easy.

In the formula (1-3), the formula (1-4), the formula (2-3), the formula (2-4), the formula (3-3) and the formula (3-4), $m_1$ and $m_2$ each represent preferably an integer of 3 to 5, more preferably 3 or 4, further preferably 3, because the luminance life of a light emitting device using the metal complex of the present invention is excellent.

In the formula (1-3), the formula (1-4), the formula (2-3), the formula (2-4), the formula (3-3) and the formula (3-4), $m_1$ and $m_2$ may be mutually the same or different, and it is preferable that $m_1$ and $m_2$ are mutually the same because synthesis of the metal complex of the present invention is easy.

In the formula (1-3), the formula (1-4), the formula (2-3), the formula (2-4), the formula (3-3) and the formula (3-4), $R^{15}$, $R^{16}$, $R^{17}$ and $R^{18}$ each represent preferably a hydrogen atom, an alkyl group or an aryl group, more preferably a hydrogen atom or an alkyl group, because the luminance life of a light emitting device using the metal complex of the present invention is excellent.

When at least one of $R^{15}$ and $R^{16}$ is a group other than a hydrogen atom and at least one of $R^{17}$ and $R^{18}$ is a hydrogen atom, when $R^{15}$ and $R^{16}$ are mutually different, and when $R^{17}$ and $R^{18}$ are mutually different, for example, in the metal complex represented by the formula (1-3), the formula (1-4), the formula (2-3), the formula (2-4), the formula (3-3) and the formula (3-4), stereoisomers can exist. The metal complex represented by the formula (1-3), the formula (1-4), the formula (2-3), the formula (2-4), the formula (3-3) and the formula (3-4) may be a metal complex having only the same stereoisomer or may be a metal complex having mutually different several stereoisomers. The stereoisomerism includes diastereomers and enantiomers.

When the metal complex represented by the formula (1-3) has a ligand represented by the formula (1-3-Z), the stereoisomerism of the ligand represented by the formula (1-3-Z) is represented by, for example, the formula (1-3-a), the formula (1-3-b), the formula (1-3-c) and the formula (1-3-d).

[Chemical Formula 37]

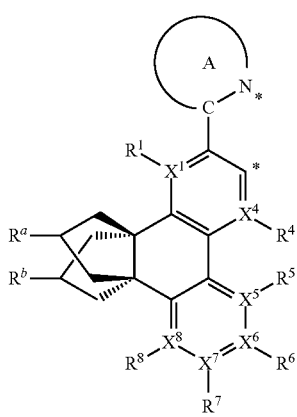

(1-3-Z)

[Chemical Formula 38]

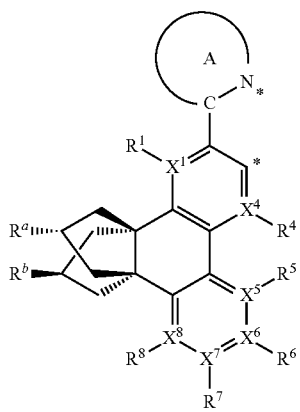

(1-3-a)

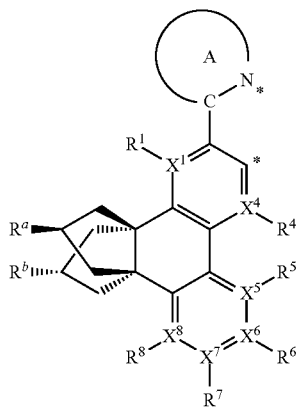

(1-3-b)

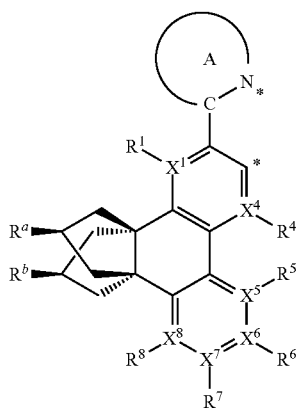

(1-3-c)

(1-3-d)

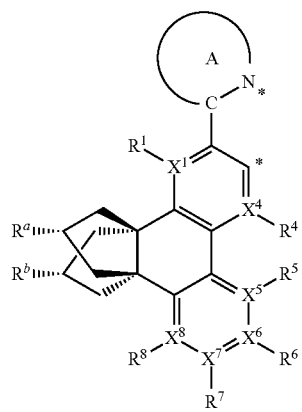

[wherein, * represents a position linking to an iridium atom or a platinum atom. $R^a$ and $R^b$ each independently represent an alkyl group or a cycloalkyl group, the foregoing groups each optionally having a substituent.]

The ligands represented by the formula (1-3-a), the formula (1-3-b), the formula (1-3-c) and the formula (1-3-d) are in a relation of mutual diastereomers.

The metal complexes represented by the formula (1), the formula (2) and the formula (3) include, for example, metal complexes represented by the following formulae (Ir-1) to (Ir-30). Of them, metal complexes represented by the formula (Ir-1) to the formula (Ir-24) are preferable and metal complexes represented by the formulae (Ir-1) to (Ir-3), (Ir-7) to (Ir-11), (Ir-13) to (Ir-18) or (Ir-20) to (Ir-24) are more preferable because the quantum yield of the metal complex of the present invention is more excellent, and metal complexes represented by the formulae (Ir-1), (Ir-7) to (Ir-10), (Ir-13), (Ir-15), (Ir-16), (Ir-18), (Ir-20) or (Ir-21) are further preferable and metal complexes represented by the formula (Ir-1), (Ir-10), (Ir-13) or (Ir-15) are particularly preferable because synthesis of the metal complex of the present invention is easy.

[Chemical Formula 39]

(Ir-2)

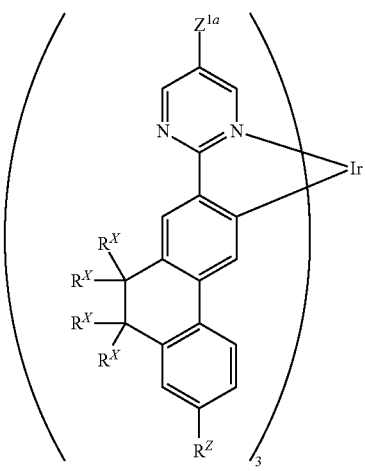

(Ir-3)

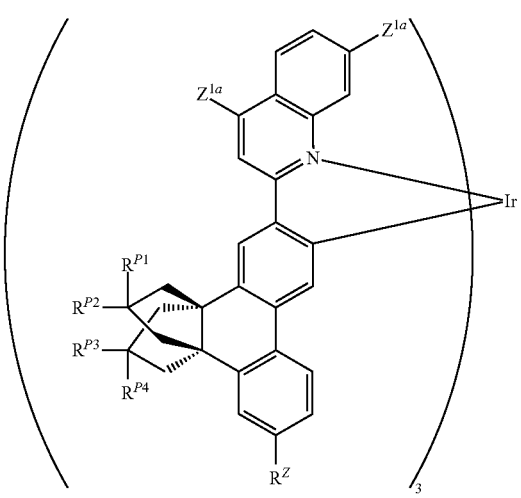

(Ir-1)

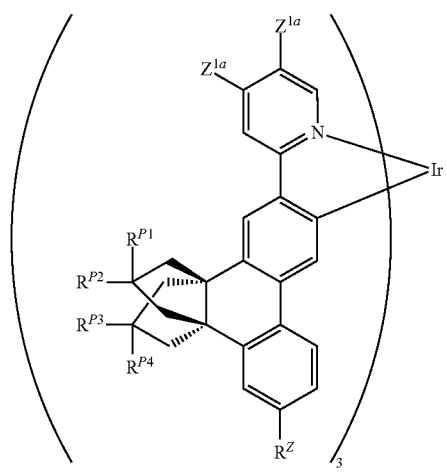

(Ir-4)

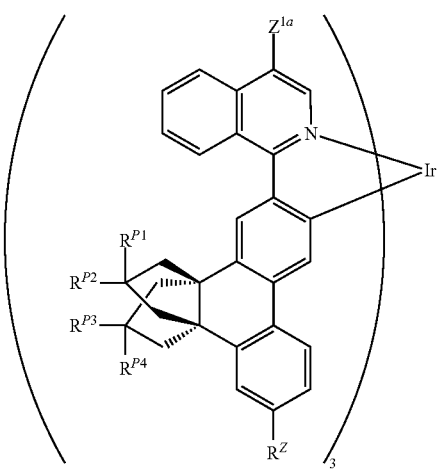

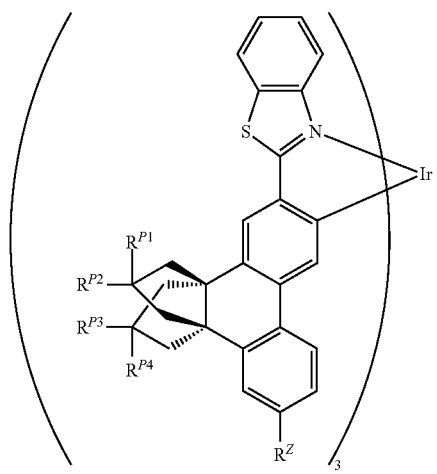
(Ir-5)
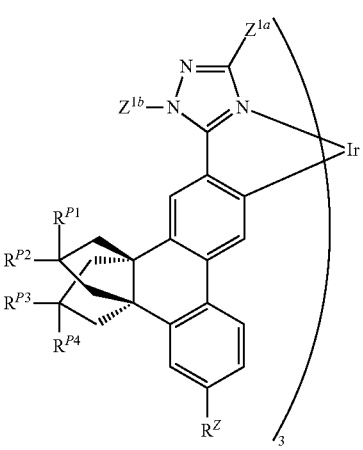
(Ir-8)
[Chemical Formula 40]
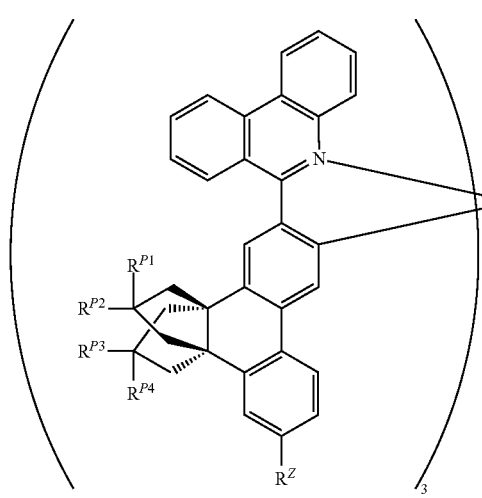
(Ir-6)
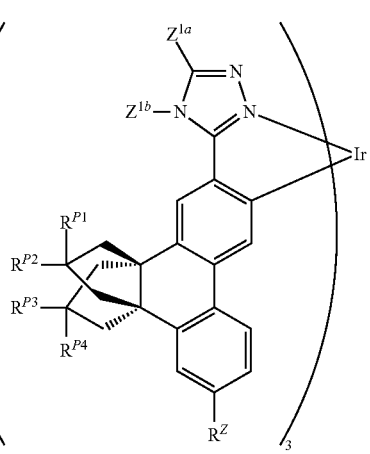
(Ir-9)
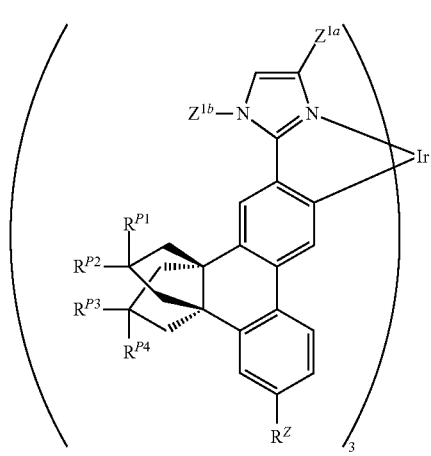
(Ir-7)
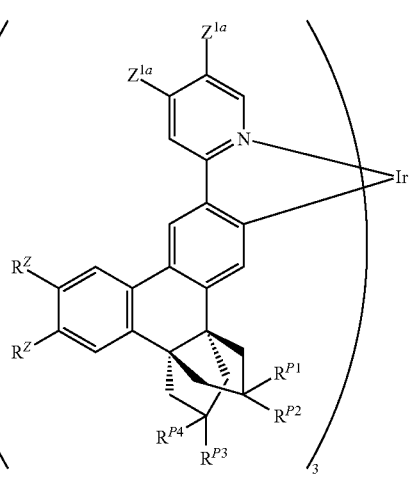
(Ir-10)

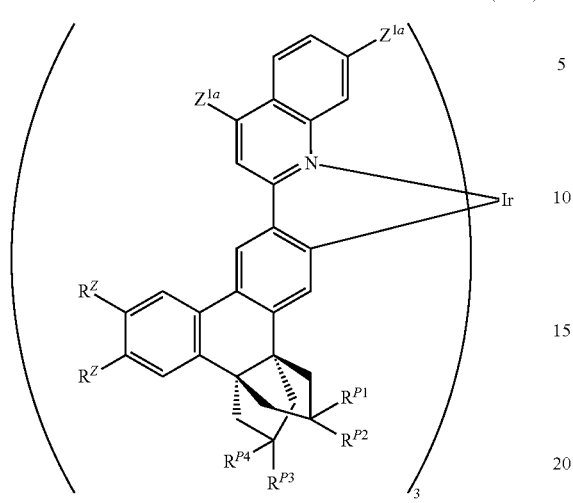
(Ir-11)
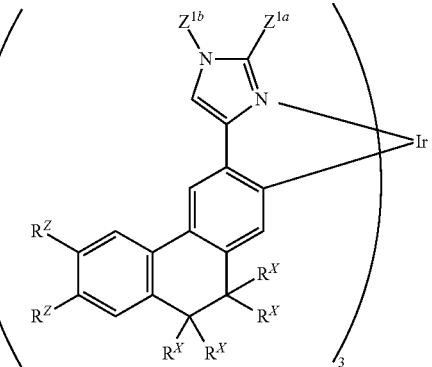
(Ir-14)
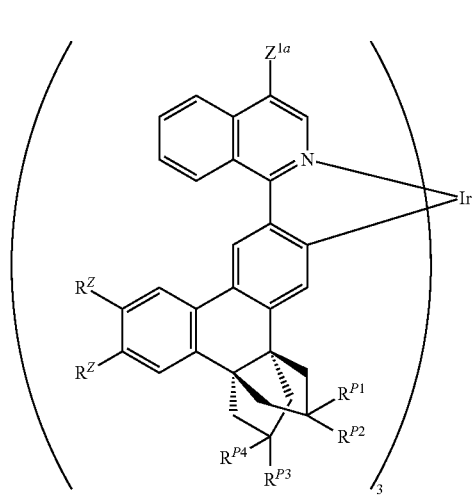
(Ir-12)
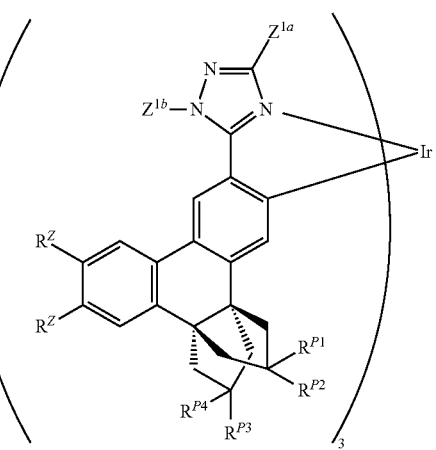
(Ir-15)
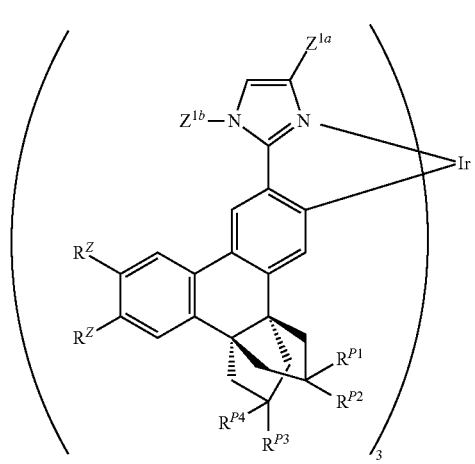
(Ir-13)
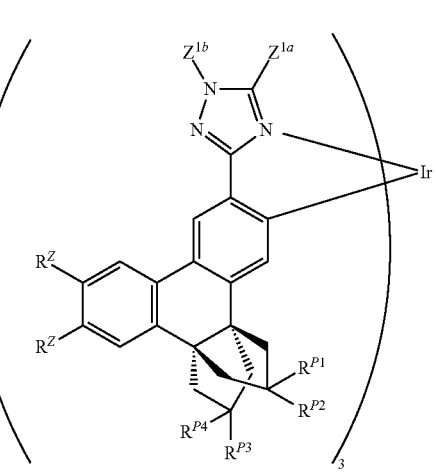
(Ir-16)

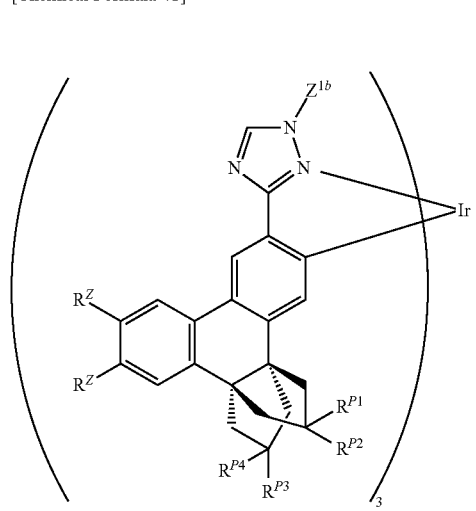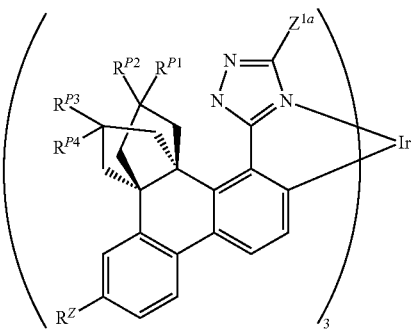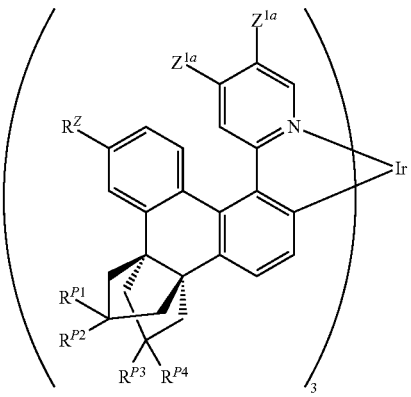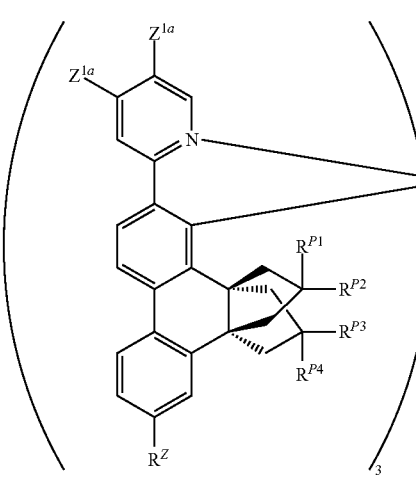

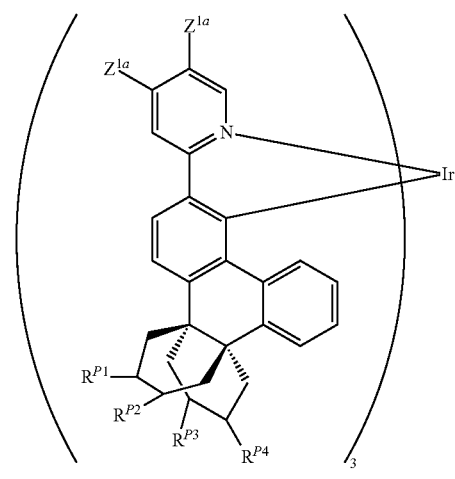
(Ir-24)
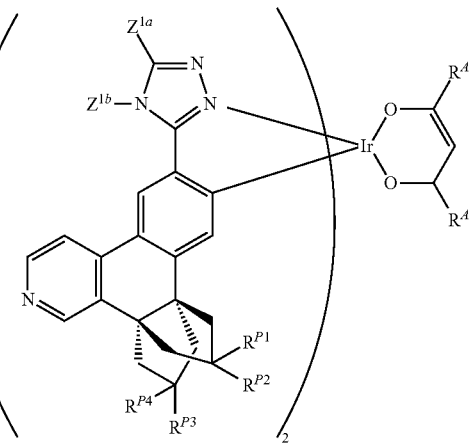
(Ir-27)
[Chemical Formula 42]
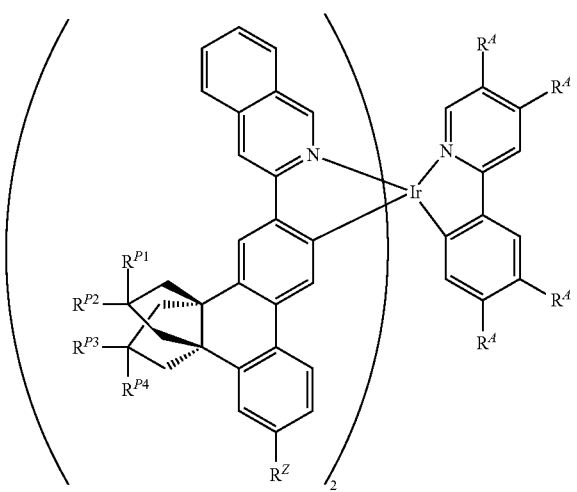
(Ir-25)
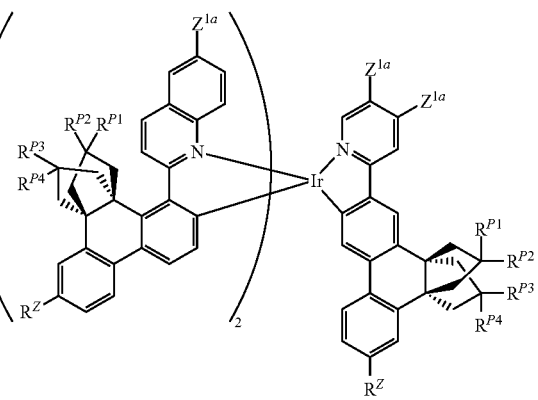
(Ir-28)
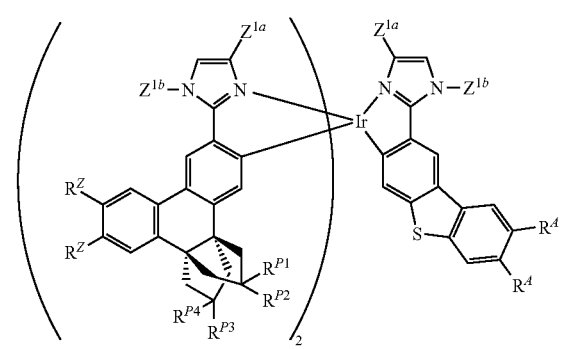
(Ir-26)
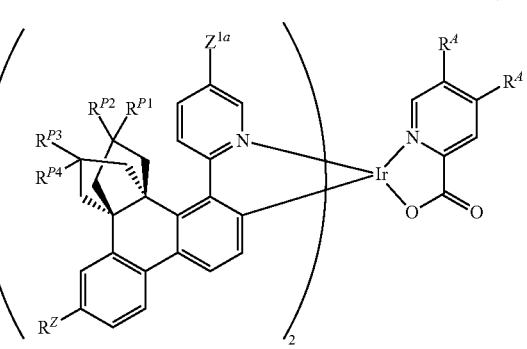
(Ir-29)

-continued (Ir-30)

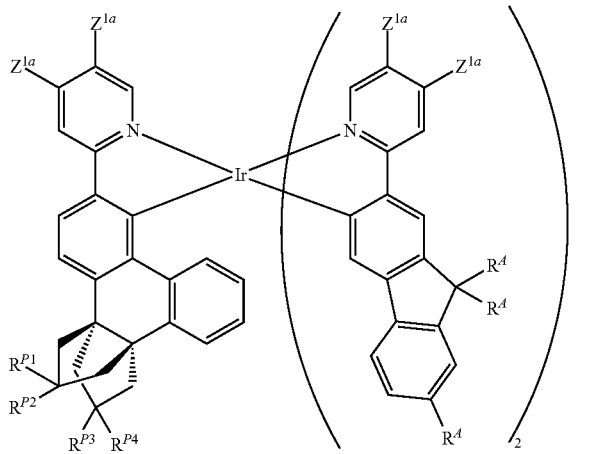

[wherein, $Z^{1a}$, $R^{P1}$, $R^{P2}$, $R^{P3}$, $R^{P4}$, $R^Z$ and $R^A$ each independently represent a hydrogen atom, an alkyl group, a cycloalkyl group, an aryl group, a monovalent heterocyclic group, a substituted amino group or a halogen atom, the foregoing groups each optionally having a substituent. When there are plurality of $Z^{1a}$, $R^{P1}$, $R^{P2}$, $R^{P3}$, $R^{P4}$, $R^Z$ or $R^A$, they may be the same or different at each occurrence.

$Z^{1b}$ represents an alkyl group, a cycloalkyl group, an aryl group, a monovalent heterocyclic group, a substituted amino group or a halogen atom, the foregoing groups each optionally having a substituent. When there are a plurality of $Z^{1b}$, they may be the same or different.

$R^X$ represents a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent. The plurality of $R^X$ may be the same or different, and may be combined together to form a ring together with the atoms to which they are attached. At least one of the plurality of $R^X$ is an alkyl group, a cycloalkyl group, an alkoxy group, a cycloalkoxy group, an aryl group, an aryloxy group, a monovalent heterocyclic group or a halogen atom.].

When the plurality of Rx are mutually different, when at least one of $R^{P1}$ and $R^{P2}$ is a group other than a hydrogen atom and at least one of $R^{P3}$ and $R^{P4}$ is a hydrogen atom, when $R^{P1}$ and $R^{P2}$ are mutually different, and when $R^{P3}$ and $R^{P4}$ are mutually different, for example, in the formulae (Ir-1) to (Ir-30), stereoisomers (diastereomer and/or enantiomer) can exist in the metal complex represented by the formulae (Ir-1) to (Ir-30). The metal complex represented by the formulae (Ir-1) to (Ir-30) may be a single stereoisomer or may be a mixture of different stereoisomers.

In the formulae (Ir-1) to (Ir-30), $Z^{1a}$ is preferably a group selected from Group I or a group selected from Group II described below, more preferably a group selected from Group II, further preferably a group represented by the formulae (II-1) to (II-15), particularly preferably a group represented by the formulae (11-7) to (II-15).

In the formulae (Ir-1) to (Ir-30), $Z^{1b}$ is preferably a group selected from Group I or a group selected from Group II described below, more preferably a group selected from Group I or a group represented by the formulae (II-1) to (11-6), further preferably a group selected from Group I, particularly preferably a group represented by the formulae (I-7) to (I-15).

In the formulae (Ir-1) to (Ir-30), $R^{P1}$, $R^{P2}$, $R^{P3}$, $R^{P4}$, $R^Z$, $R^A$ and $R^X$ each represent preferably a group selected from Group I or a group selected from Group II described below, more preferably a group selected from Group I, further preferably a group represented by the formulae (I-1) to (I-6).

<Group I>

[Chemical Formula 43]

—Me (I-1)

—C₃H₇ (I-2)

—Bu (I-3)

—t-Bu (I-4)

—C₆H₁₃ (I-5)

—Br (I-6)

[Chemical Formula 44]

(I-7)

[structure: para-methylphenyl]

(I-8)

[structure: para-butylphenyl]

(I-9)

[structure: para-t-butylphenyl]

(I-10)

[structure: para-hexylphenyl]

(I-11)

[structure: 3,5-dimethylphenyl]

(I-12) 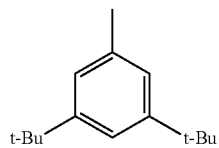
(I-13) 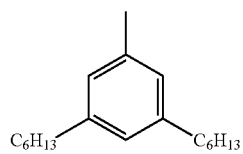
(I-14) 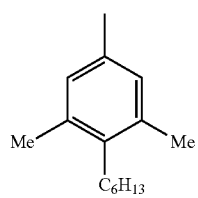
(I-15) 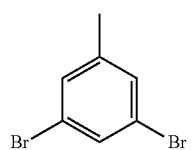
<Group II>
[Chemical Formula 45]
(II-1) 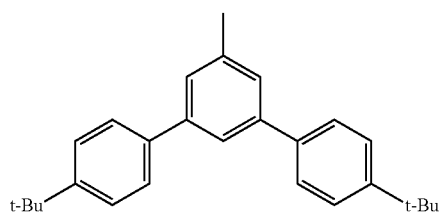
(II-2) 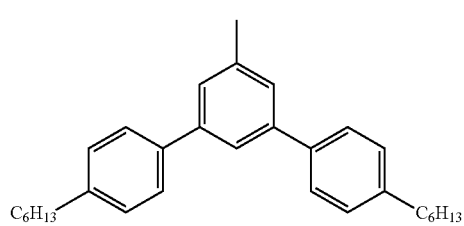
(II-3) 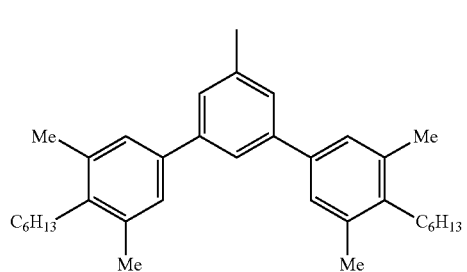
(II-4) 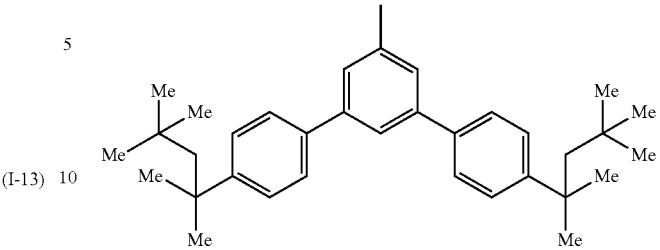
(II-5) 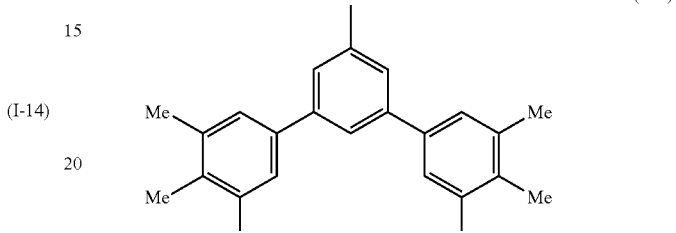
(II-6) 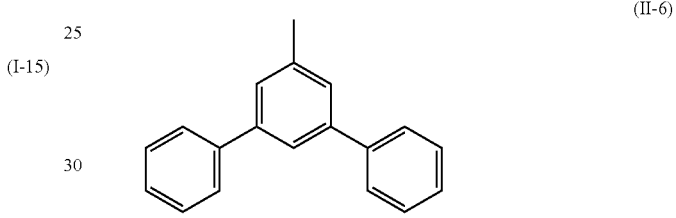
[Chemical Formula 46]
(II-7) 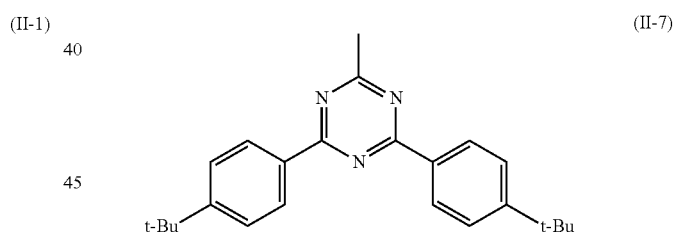
(II-8) 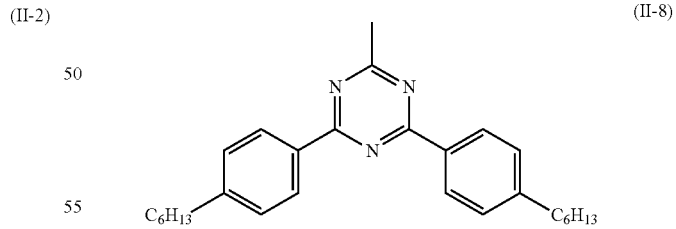
(II-9) 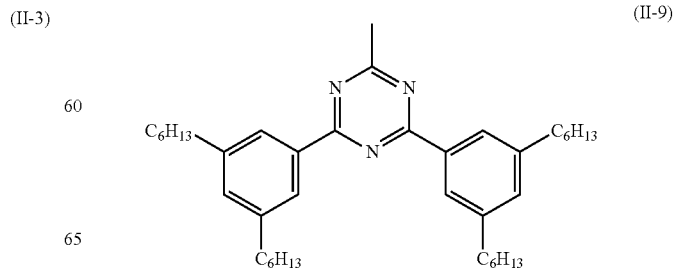

(II-10) 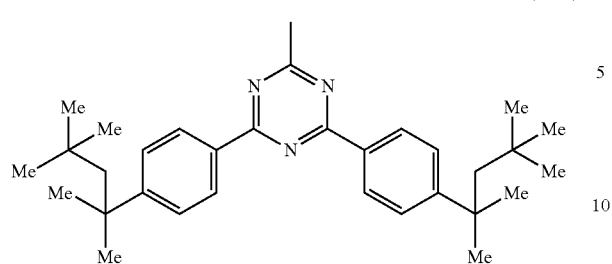
(II-11) 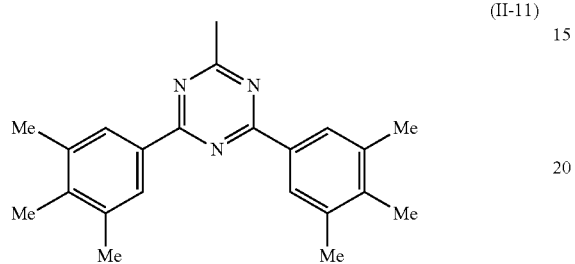
(II-12) 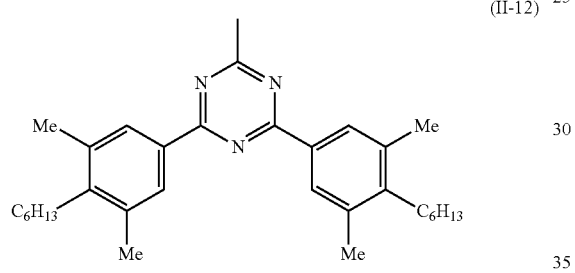
(II-13) 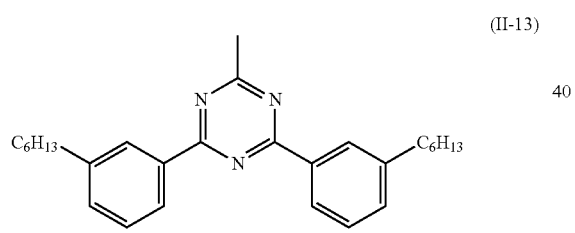
[Chemical Formula 48]
(II-14) 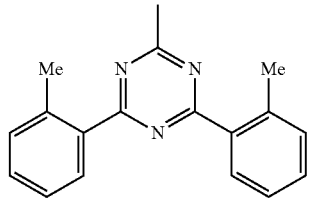
(II-15) 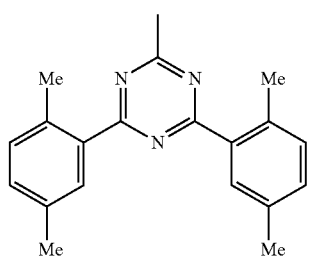
[Chemical Formula 47]
(II-16) 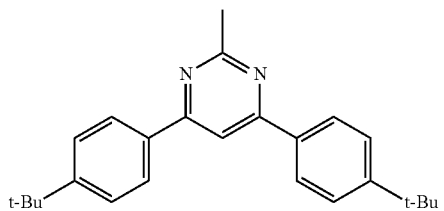
(II-17) 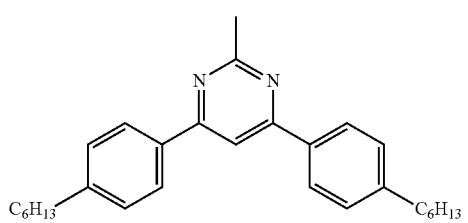
Examples of the metal complex represented by the formula (1) to the formula (3) include metal complexes represented by the following formulae (Ir-101) to (Ir-130).
(Ir-101) 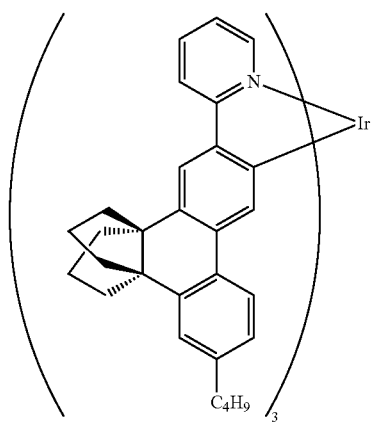

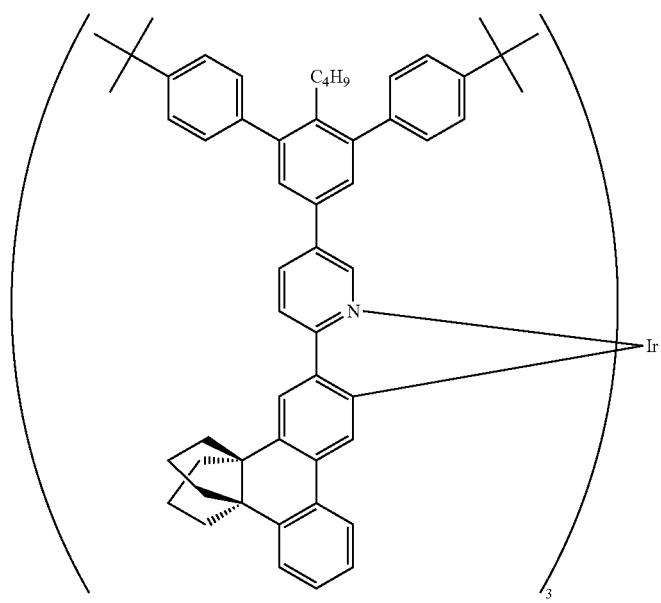
(Ir-102)
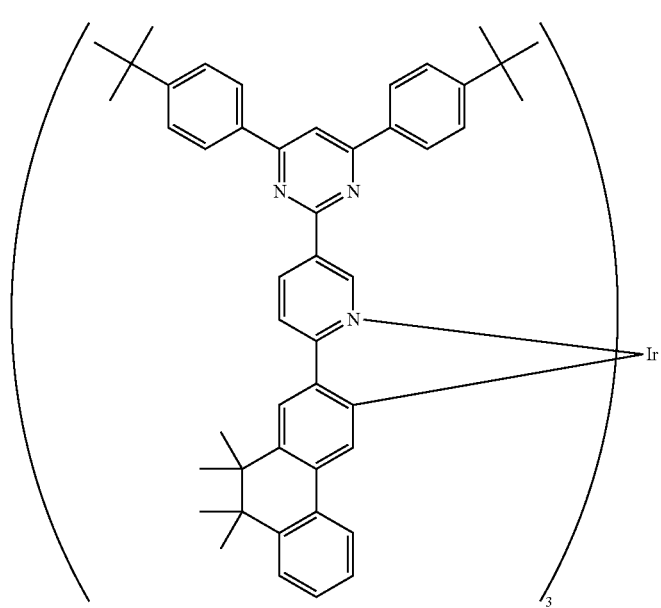
(Ir-103)

[Chemical Formula 49]
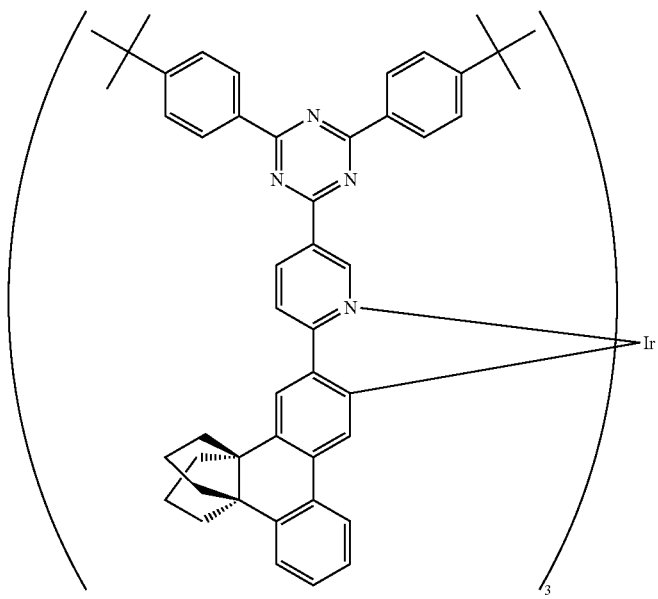
(Ir-104)
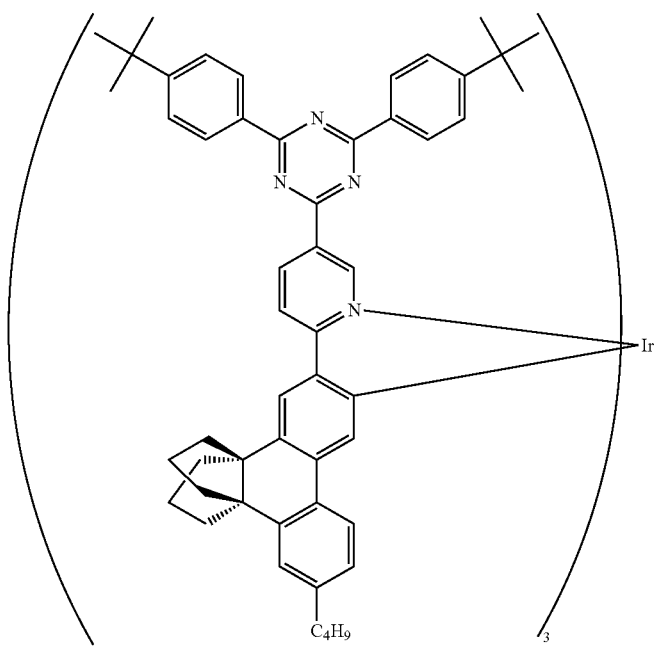
(Ir-105)

-continued
(Ir-106)
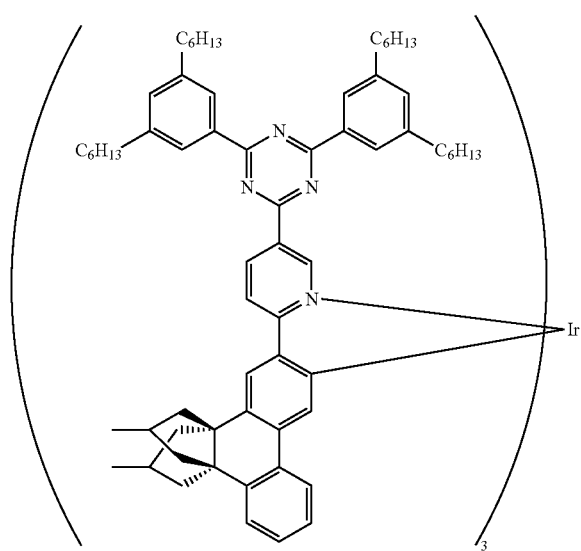
[Chemical Formula 50]
(Ir-107)
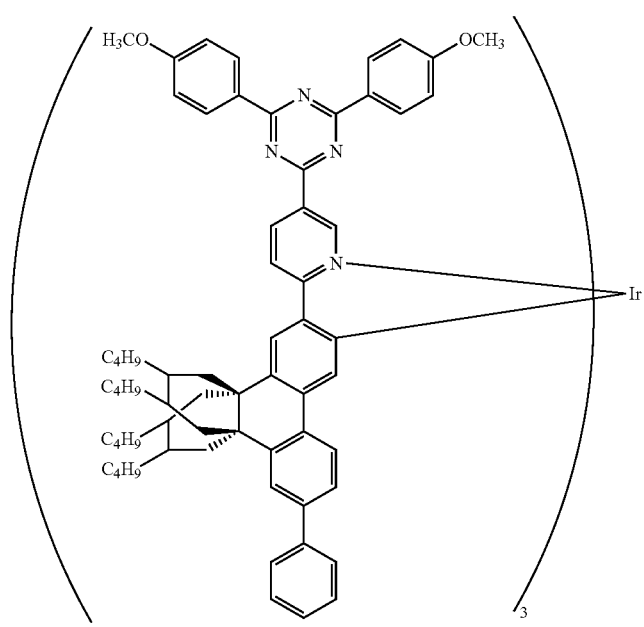

(Ir-108)
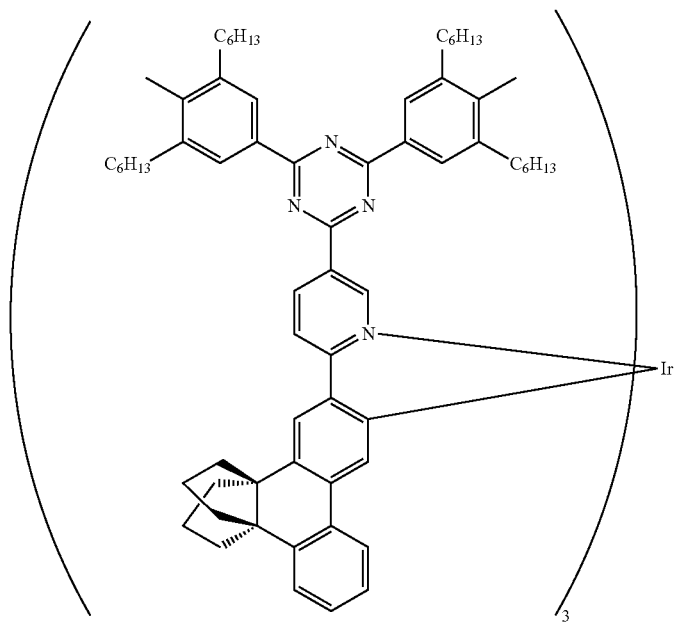
(Ir-109)
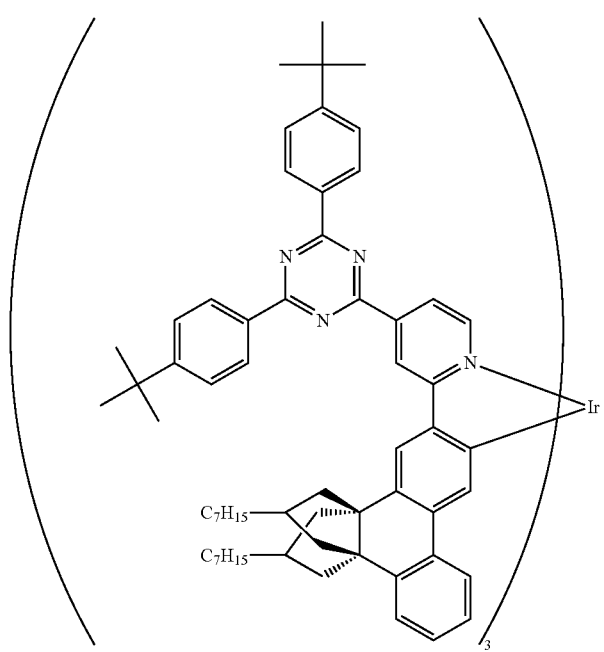

[Chemical Formula 51]
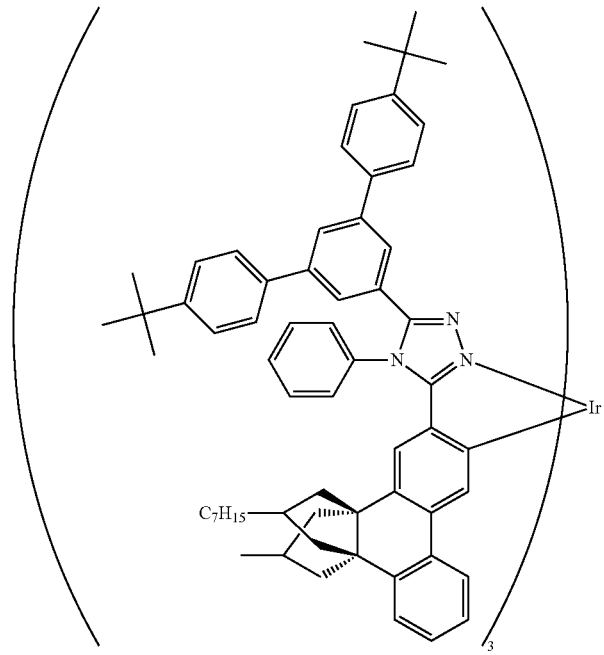
(Ir-110)
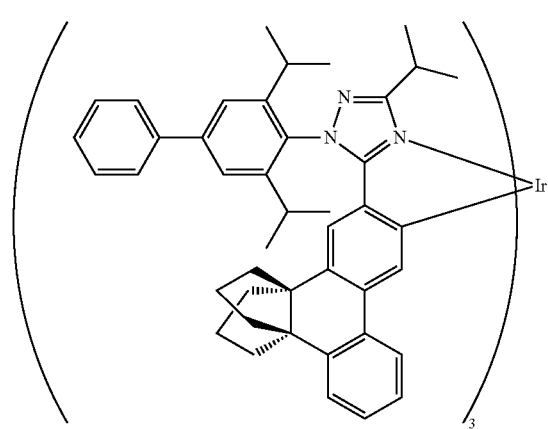
(Ir-111)

-continued
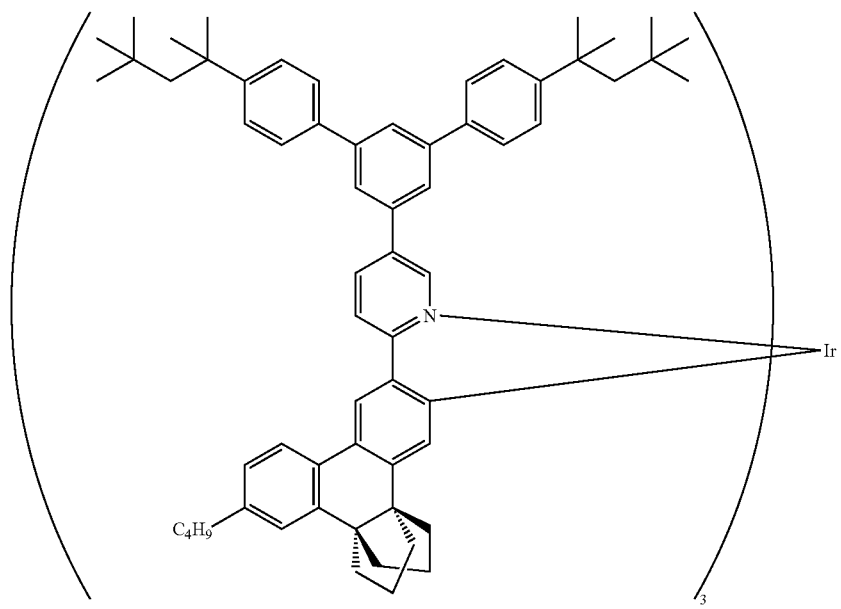
(Ir-112)
[Chemical Formula 52]
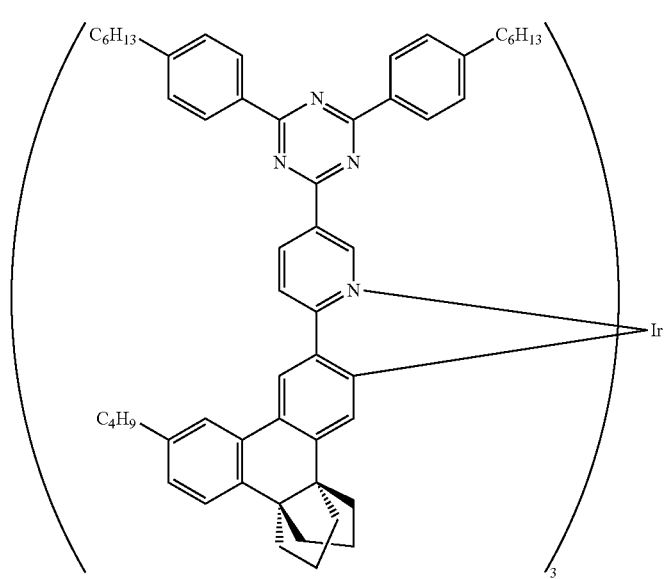
(Ir-113)

(Ir-114)
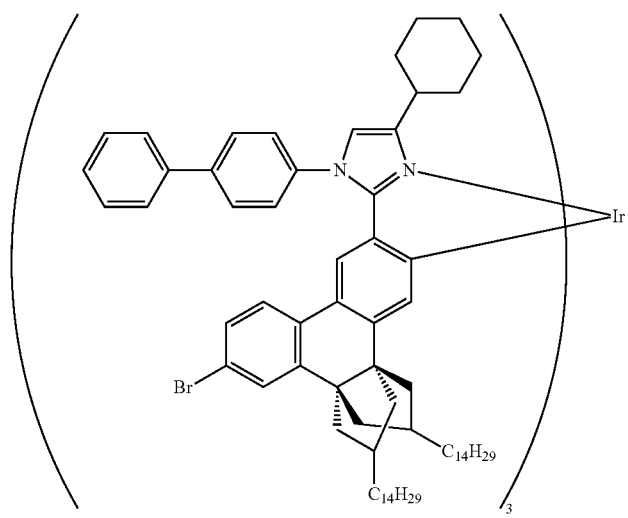
(Ir-115)
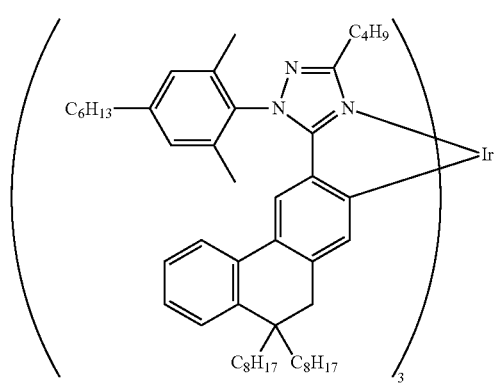
[Chemical Formula 53]
(Ir-116)
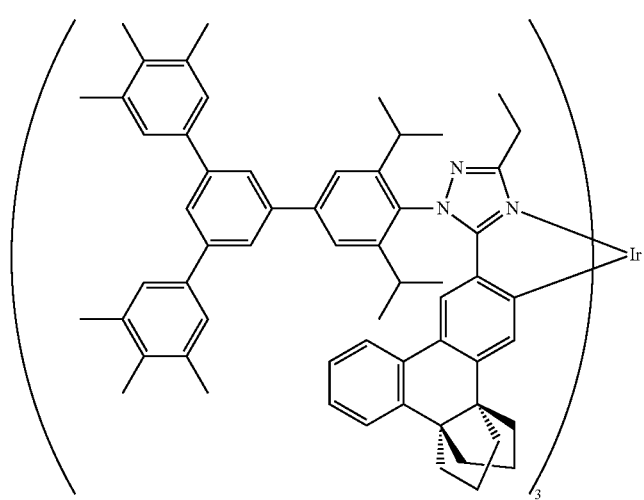

(Ir-117)
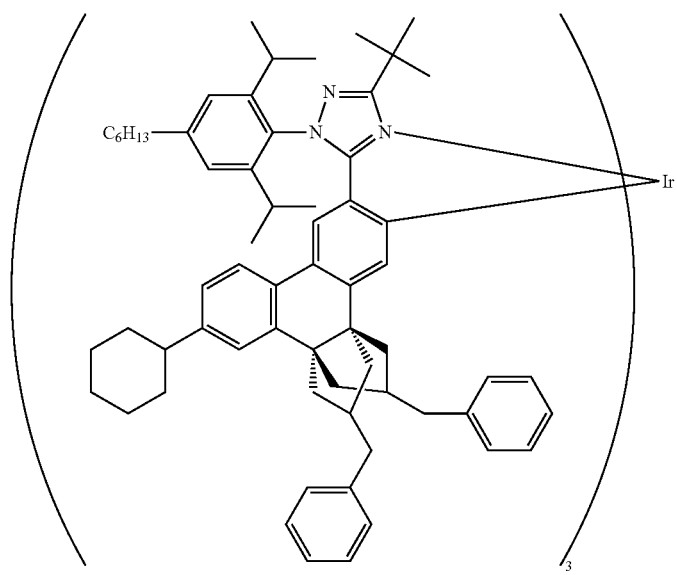
(Ir-118)
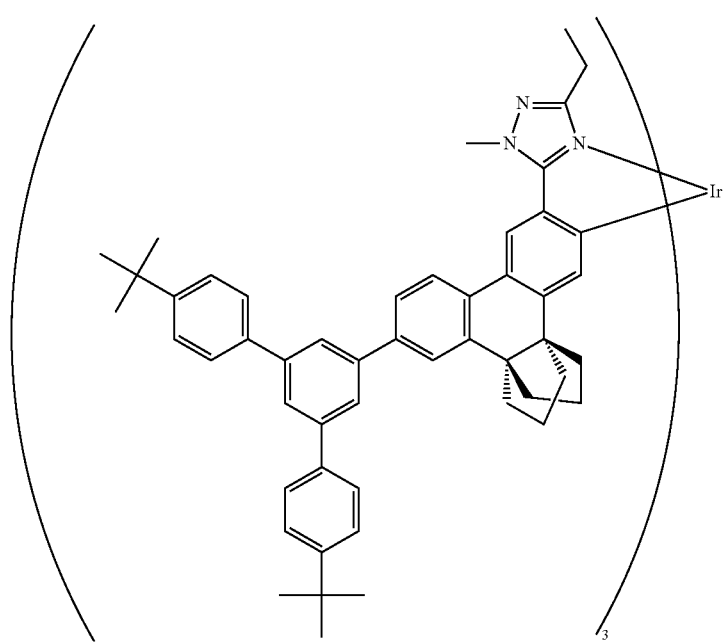

-continued
[Chemical Formula 54]
(Ir-119)
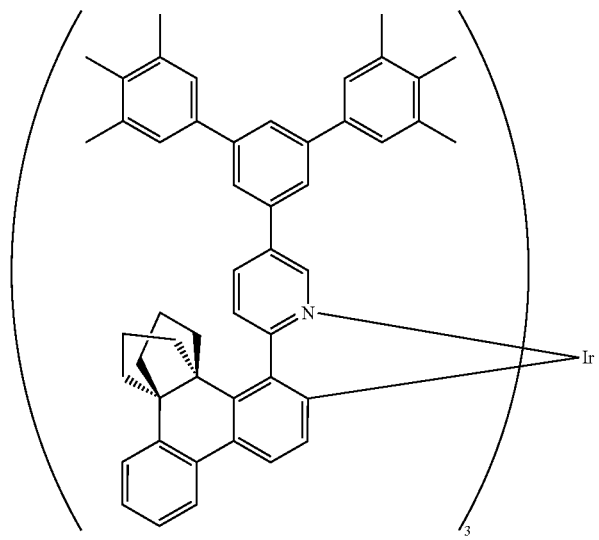
(Ir-120)
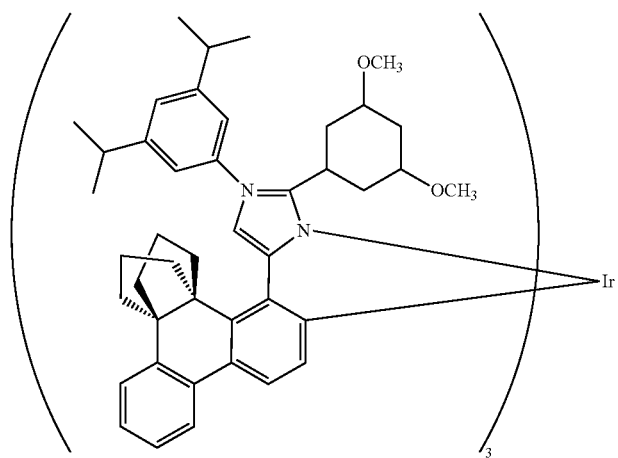
(Ir-121)
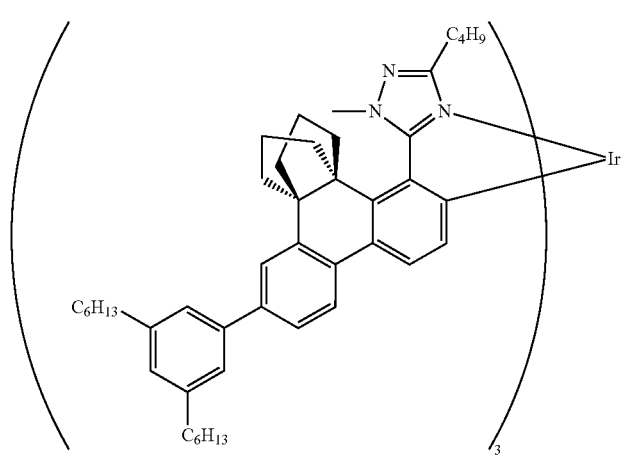

[Chemical Formula 55]
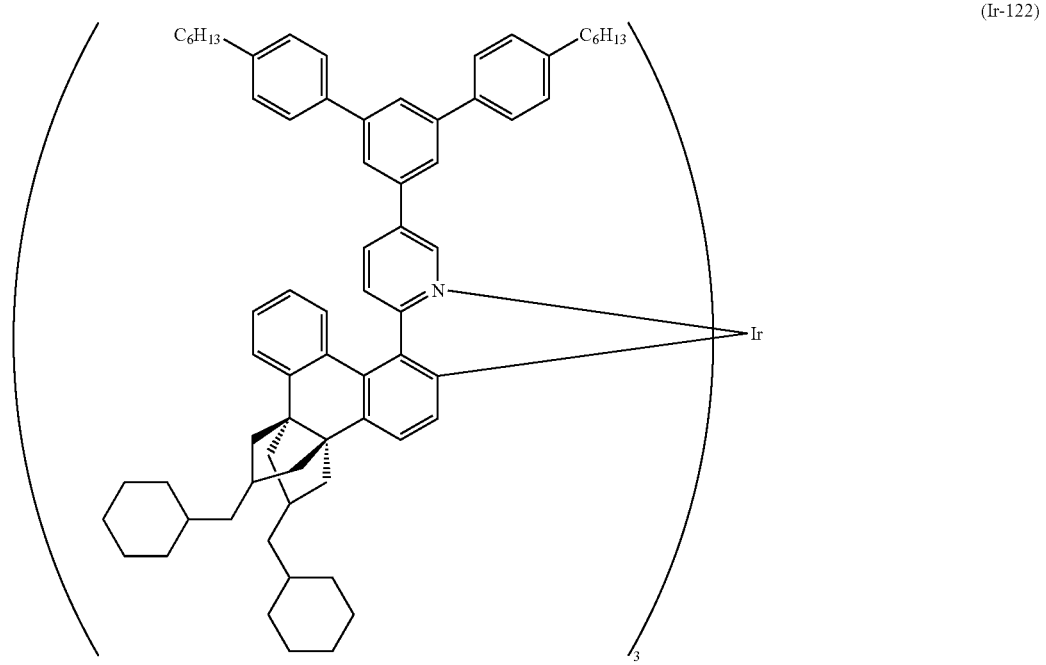
(Ir-122)
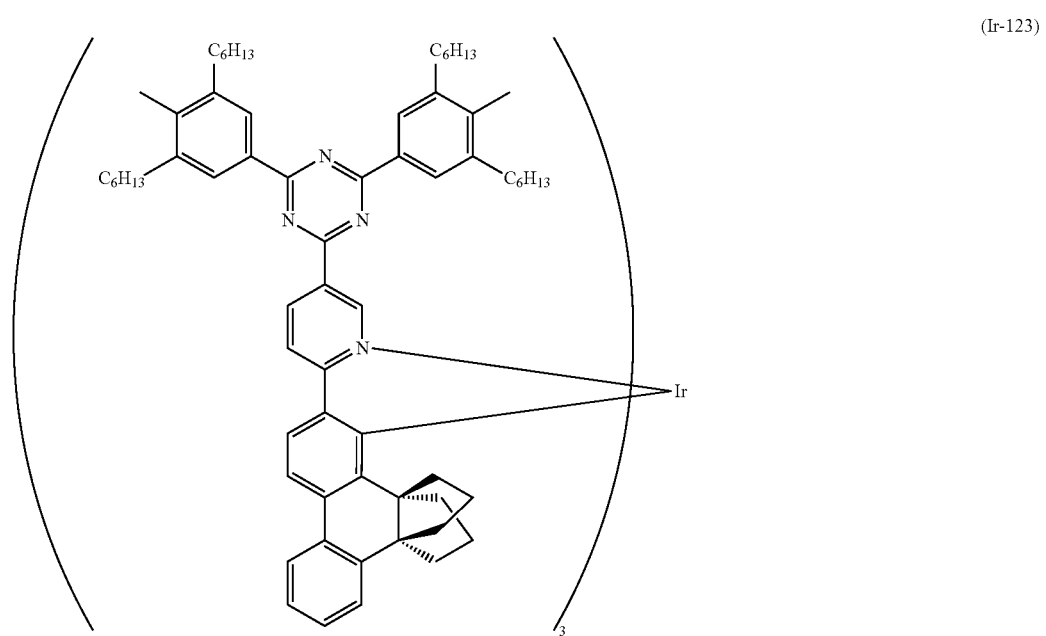
(Ir-123)

(Ir-124)
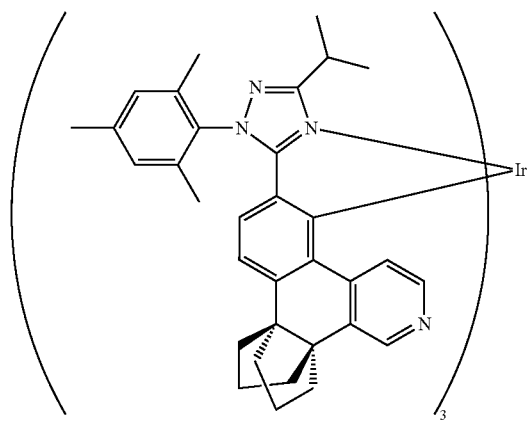
[Chemical Formula 56]
(Ir-125)
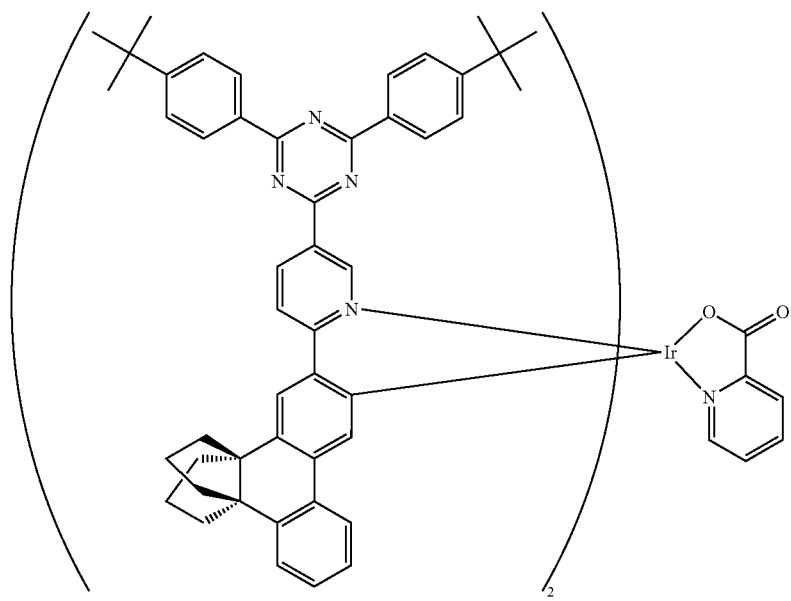
(Ir-126)
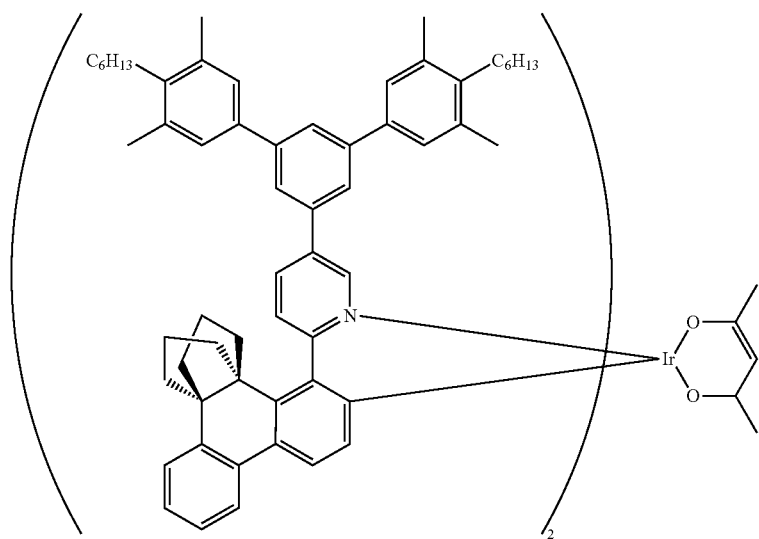

[Chemical Formula 57]
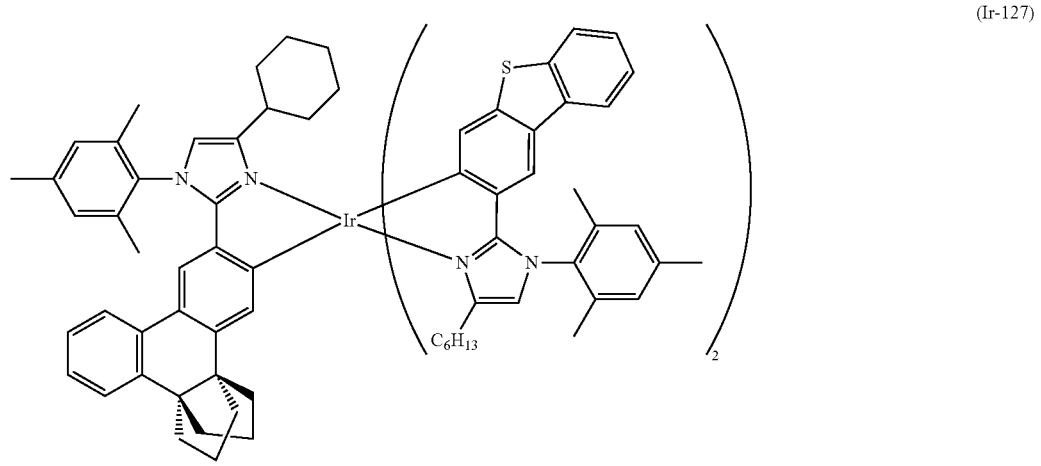
(Ir-127)
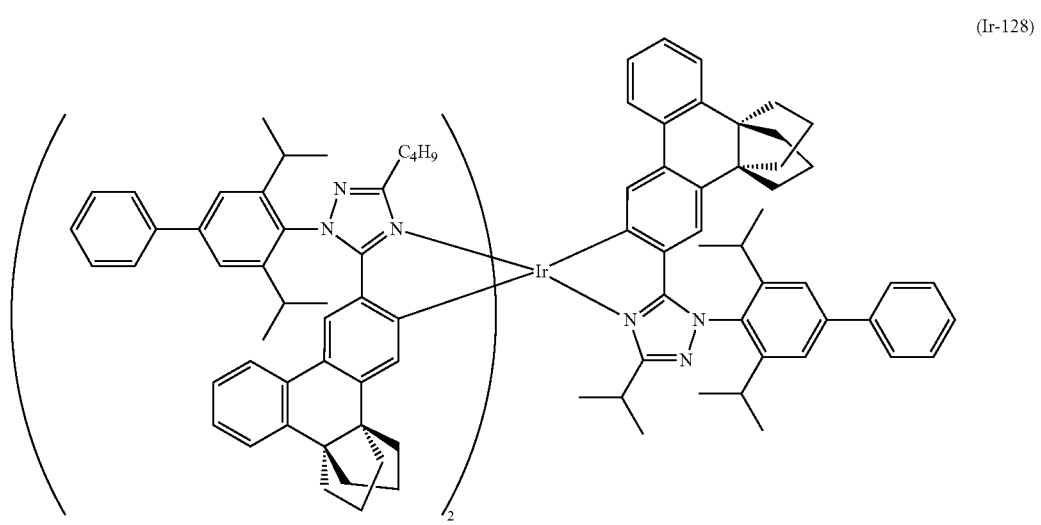
(Ir-128)

[Chemical Formula 58]

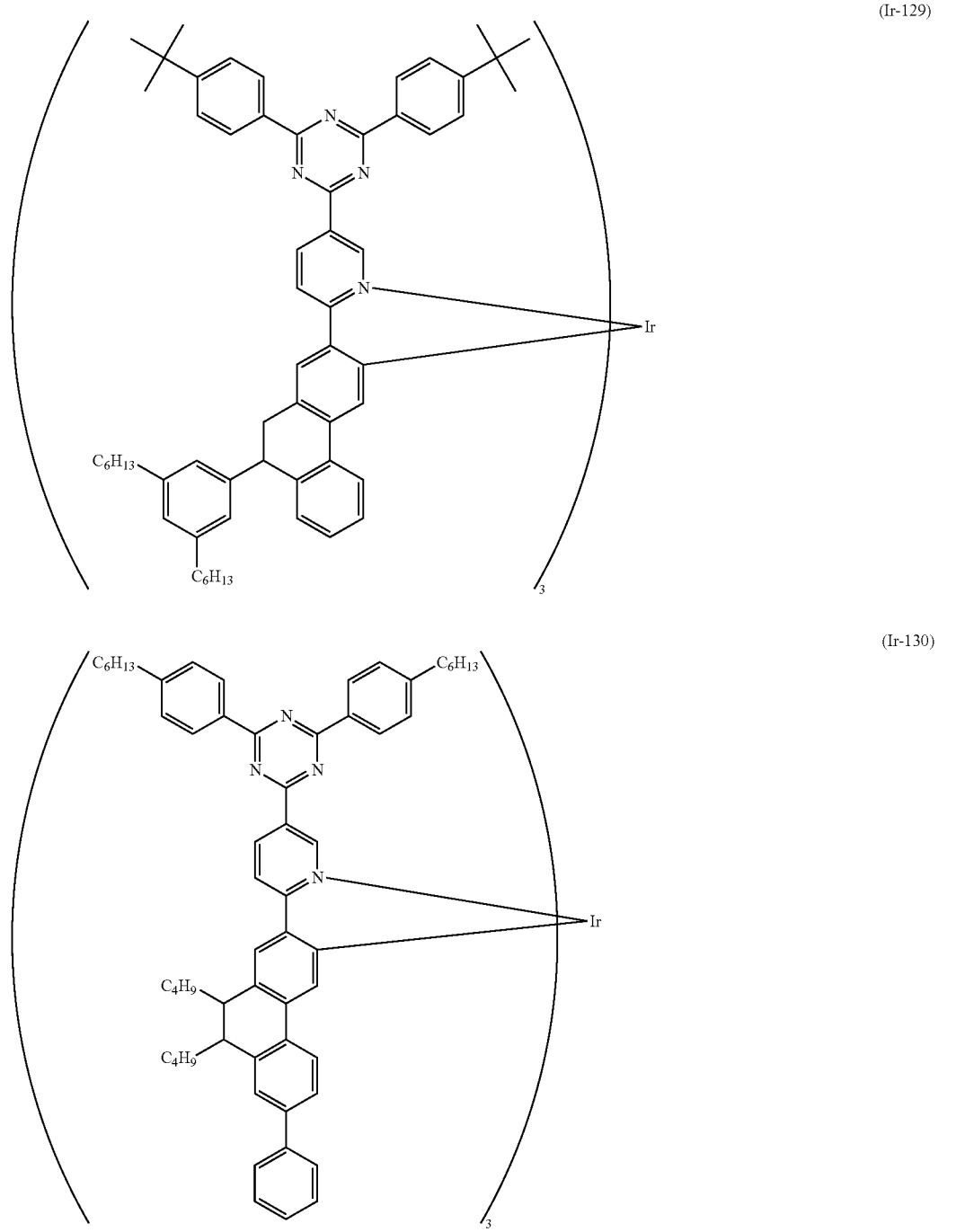

(Ir-129)

(Ir-130)

The metal complex represented by the formula (1) to the formula (3) can include a plurality of stereoisomers. The metal complex includes, for example, a metal complex having a ligand as an enantiomer, a metal complex having a ligand as a diastereomer, a metal complex which is totally a diastereomer owing to the presence of a plurality of ligands as an enantiomer, and the like.

Of the metal complexes represented by the formula (1) to the formula (3), the metal complex in which M is an iridium atom and $n_2$ is 0 can include stereoisomers as a facial isomer or a meridional isomer, and the proportion of the facial isomer with respect to the total metal complex is preferably 80% by mol or more, more preferably 90% by mol or more, further preferably 99% by mol or more, particularly preferably 100%, by mol (that is, no meridional isomer is contained), because the full width at half maximum of the emission spectrum of the metal complex of the present invention is more excellent.

In a light emitting device produced by using the metal complex of the present invention, the metal complexes of the present invention may be used singly or in combination of two or more.

<Production Method of Metal Complex Represented by Formula (1)>
[Production Method 1]

A metal complex represented by the formula (1) as the metal complex of the present invention can be produced, for example, by a method of reacting a metal compound and a compound as a ligand. If necessary, a reaction of exchanging functional groups of a ligand of the metal complex may be performed.

Of the metal complexes represented by the formula (1), the metal complex in which M is an iridium atom and n1 is 3 can be produced, for example, by a method comprising a step A1 of reacting a compound represented by the formula (M1-1) and an iridium compound or its hydrate to synthesize a metal complex represented by the formula (M1-2) and a step B1 of reacting the metal complex represented by the formula (M1-2) and the compound represented by the formula (M1-1) or a precursor of a ligand represented by $A^1$-$G^1$-$A^2$ such as methanol, ethanol, propanol, ethylene glycol, propylene glycol, glycerin, 2-methoxyethanol, 2-ethoxyethanol, 2-(2-ethoxyethoxy)ethanol, 2-(i-propoxy)ethanol, 2-(n-butoxy)ethanol, 2-(t-butoxy)ethanol and the like; ether solvents such as diehyl ether, tetrahydrofuran, dioxane, cyclopentyl methyl ether, diglyme and the like; halogen-based solvents such as methylene chloride, chloroform and the like; nitrile solvents such as acetonitrile, benzonitrile and the like; hydrocarbon solvents such as hexane, decalin, toluene, xylene, mesitylene and the like; amide solvents such as N,N-dimethylformamide, N,N-dimethylacetamide and the like; acetone, dimethyl sulfoxide, and water.

In the step A1 and the step B1, the reaction time is usually 30 minutes to 150 hours and the reaction temperature is usually between the melting point and the boiling point of a solvent present in the reaction system.

In the step A1, the amount of the compound represented by the formula (M1-1) is usually 2 to 20 mol with respect to 1 mol of the iridium compound or its hydrate.

[Chemical Formula 59]

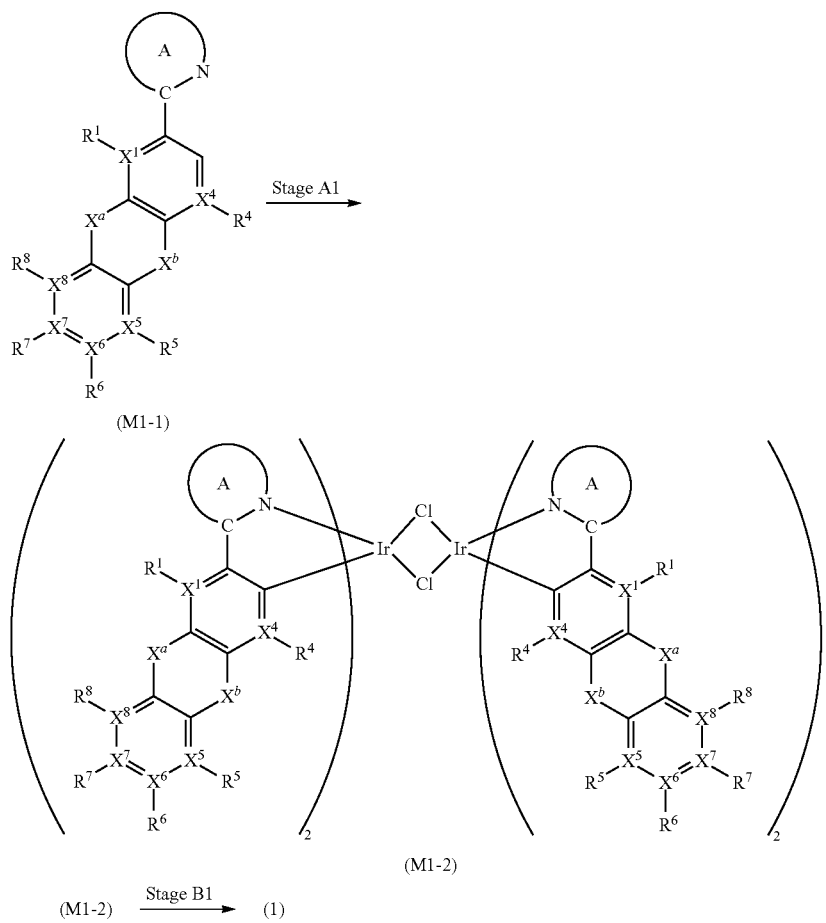

[wherein, $X^1$, $X^4$ to $X^8$, $R^1$, $R^4$ to $R^8$, $X^a$, $X^b$ and ring A are as defined above.]

In the step A1, the iridium compound includes, for example, iridium chloride, tris(acetylacetonato)iridium(III), chloro(cyclooctadiene)iridium(I) dimer and iridium(III) acetate, and the hydrate of the iridium compound includes, for example, iridium chloride*trihydrate.

The step A1 and the step B1 are usually conducted in a solvent. The solvent includes, for example, alcohol solvents In the step B1, the amount of the compound represented by the formula (M1-1) or the precursor of a ligand represented by $A^1$-$G^1$-$A^2$ is usually 1 to 100 mol with respect to 1 mol of the metal complex represented by the formula (M1-2).

In the step B1, the reaction is preferably conducted in the presence of a silver compound such as silver trifluoromethanesulfonate and the like. When a silver compound is used, its amount is usually 2 to 20 mol with respect to 1 mol of the metal complex represented by the formula (M1-2).

When ring A has a group represented by the above-described formula (D-A) or the formula (D-B) as a substituent, the compound represented by the formula (M1-1) can be synthesized, for example, by a step of conducting a coupling reaction such as the Suzuki reaction, the Kumada reaction, the Stille reaction and the like of a compound represented by the formula (M1-3) and a compound represented by the formula (M1-4).

[Chemical Formula 60]

(M1-3) + $Z^1$—$W^1$ (M1-4) → (M1-1)

[wherein, $X^1$, $X^4$ to $X^8$, $R^1$, $R^4$ to $R^8$, $X^a$ and $X^b$ are as defined above.

Ring B represents a heteroaromatic ring having a group represented by $W^{11}$ as a substituent and this aromatic heterocyclic ring optionally has a substituent other than a group represented by $W^{11}$. $W^{11}$ represents a group represented by —B(OR$^{W1}$)$_2$, an alkylsulfonyloxy group, a cycloalkylsulfonyloxy group, an arylsulfonyloxy group, a chlorine atom, a bromine atom or an iodine atom, the foregoin groups each optionally having a substituent.

$Z^1$ represents a group represented by the above-described formula (D-A) or (D-B).

$W^1$ represents a group represented by —B(OR$^{W1}$)$_2$, an alkylsulfonyloxy group, a cycloalkylsulfonyloxy group, an arylsulfonyloxy group, a chlorine atom, a bromine atom or an iodine atom, the foregoing groups each optionally having a substituent.

$R^{W1}$ represents a hydrogen atom, an alkyl group, a cycloalkyl group, an aryl group or an amino group, the foregoing groups each optionally having a substituent. The plurality of $R^{W1}$ may be the same or different, and may be combined together to form a ring structure together with the atoms to which they are attached.]

The group represented by —B(OR$^{W1}$)$_2$ includes, for example, groups represented by the following formulae (W-1) to (W-10).

[Chemical Formula 61]

The alkylsulfonyloxy group represented by $W^1$ includes, for example, a methanesulfonyloxy group, an ethanesulfonyloxy group and a trifluoromethanesulfonyloxy group.

The arylsulfonyloxy group represented by $W^1$ includes, for example, a p-toluenesulfonyloxy group.

$W^1$ is preferably a group represented by —B(OR$^{W1}$)$_2$, a trifluoromethanesulfonyloxy group, a chlorine atom, a bromine atom or an iodine atom because the coupling reaction of a compound represented by the formula (M1-3) and a compound represented by the formula (M1-4) progresses easily, and of them, a chlorine atom, a bromine atom or a group represented by the formula (W-7) is more preferable because synthesis of a compound represented by the formula (M1-4) is easy.

The alkylsulfonyloxy group, the cycloalkylsulfonyloxy group and the arylsulfonyloxy group represented by $W^{11}$ represent the same meaning as the alkylsulfonyloxy group, the cycloalkylsulfonyloxy group and the arylsulfonyloxy group represented by $W^{11}$, respectively.

$W^{11}$ is preferably a bromine atom, an iodine atom or a group represented by the formula (W-7).

$Z^1$ represents preferably a group represented by the formula (D-A), more preferably groups represented by the formula (D-A1) to the formula (D-A3).

The coupling reaction of a compound represented by the formula (M1-3) and a compound represented by the formula (M1-4) is usually conducted in a solvent. The solvent to be used, the reaction time and the reaction temperature are the same as those explained in the step A1 and the step B1.

In the coupling reaction of a compound represented by the formula (M1-3) and a compound represented by the formula (M1-4), the amount of the compound represented by the formula (M1-4) is usually 0.05 to 20 mol with respect to 1 mol of the compound represented by the formula (M1-3).

The compound represented by the formula (M1-4) includes, for example, compounds in which $Z^1$ is a group represented by the formulae (D-A1) to (D-A3) and $W^1$ is a group represented by —B(OR$^{W1}$)$_2$, a trifluoromethanesulfonyloxy group, a bromine atom or an iodine atom.

A compound represented by the formula (M1-4-1) as one embodiment of the compound represented by the formula (M1-4) can be synthesized, for example, by the following method.

[Chemical Formula 62]

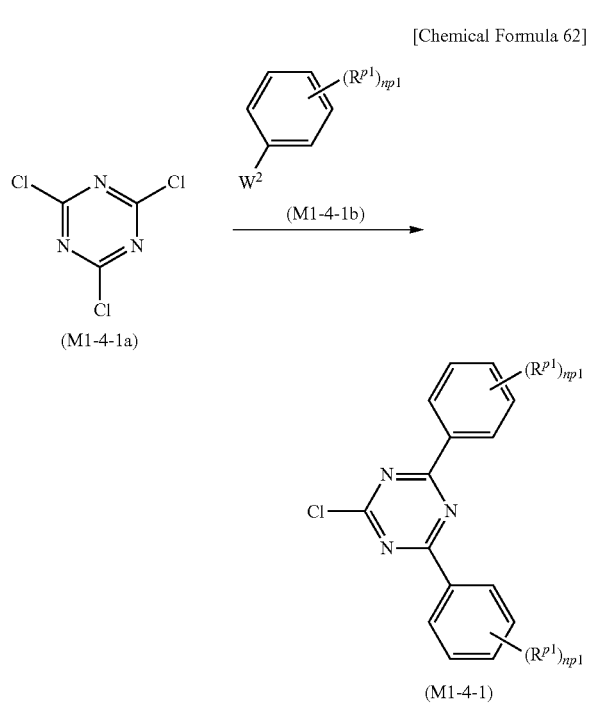

[wherein,
R$^{p1}$ and np1 are as defined above.
$W^2$ represents a group represented by —B(OR$^{W1}$)$_2$, an alkylsulfonyloxy group, a cycloalkylsulfonyloxy group, an arylsulfonyloxy group, a chlorine atom, a bromine atom or an iodine atom, the foregoing groups each optionally having a substituent.]

The compound represented by the formula (M1-4-1) can be produced, for example, by conducting a coupling reaction of a compound represented by the formula (M1-4-1a) and a compound represented by the formula (M1-4-1b). This coupling reaction is the same as that explained for the compound represented by the formula (M1-1).

A compound represented by the formula (M1-4-2) as one embodiment of the compound represented by the formula (M1-4) can be synthesized, for example, by the following method.

[Chemical Formula 63]

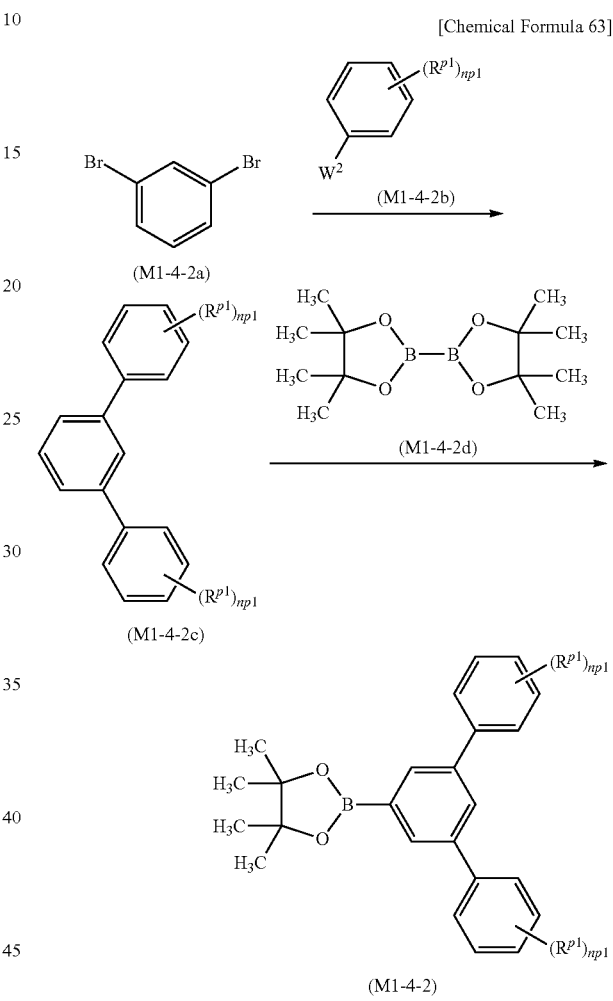

[wherein, R$^{p1}$, np1 and $W^2$ are as defined above.]

A compound represented by the formula (M1-4-2c) can be produced, for example, by conducting a coupling reaction of a compound represented by the formula (M1-4-2a) and a compound represented by the formula (M1-4-2b). This coupling reaction is the same as that explained for the compound represented by the formula (M1-1) in which ring A has a group represented by the above-described formula (D-A) or the formula (D-B) as a substituent.

The compound represented by the formula (M1-4-2) can be synthesized, for example, by conducting the Ishiyama-Miyaura-Hartwig reaction of the compound represented by the formula (M1-4-2c) and a compound represented by the formula (M1-4-2d).

A compound represented by the formula (M1-3) can be produced, for example, by conducting a coupling reaction of a compound represented by the formula (M1-5) and a compound represented by the formula (M1-6). This coupling reaction is the same as that explained for the compound represented by the formula (M1-1) in which ring A has a group represented by the above-described formula (D-A) or the formula (D-B) as a substituent.

[Chemical Formula 64]

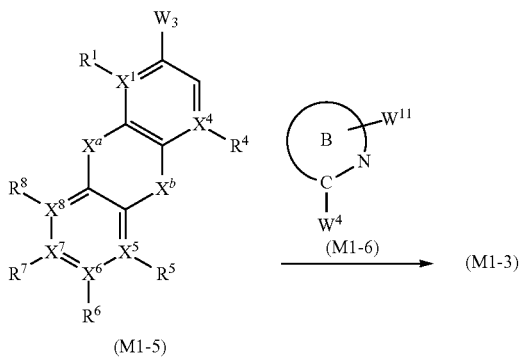

(M1-5) + (M1-6) → (M1-3)

[wherein,
$X^1$, $X^4$ to $X^8$, $R^1$, $R^4$ to $R^8$, $X^a$, $X^b$, ring B and $W^{11}$ are as defined above.

$W^3$ and $W^4$ each independently represent a group represented by —$B(OR^{W1})_2$, an alkylsulfonyloxy group, a cycloalkylsulfonyloxy group, an arylsulfonyloxy group, a chlorine atom, a bromine atom or an iodine atom, the foregoing groups each optionally having a substituent.]

When ring A does not have a group represented by the above-described formula (D-A) or the formula (D-B) as a substituent, the compound represented by the formula (M1-1) can be produced, for example, by coupling reaction of a compound represented by the formula (M1-5) and a compound represented by the formula (M1-7). This coupling reaction is the same as explained for the compound represented by the formula (M1-1) in which ring A has a group represented by the above-described formula (D-A) or the formula (D-B) as a substituent.

[Chemical Formula 65]

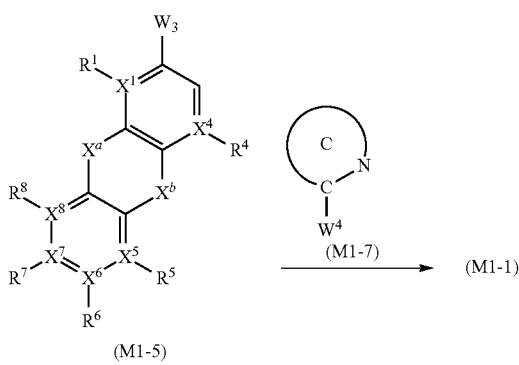

(M1-5) + (M1-7) → (M1-1)

[wherein,
$X^1$, $X^4$ to $X^8$, $R^1$, $R^4$ to $R^8$, $X^a$, $X^b$, $W^3$ and $W^4$ are as defined above.

Ring C represents a heteroaromatic ring having no group represented by the above-described formula (D-A) or the formula (D-B) as a substituent, and this aromatic heterocyclic ring optionally has a substituent other than a group represented by the above-described formula (D-A) or the formula (D-B).]

[Production Method 2]

The metal complex represented by the formula (1) as the metal complex of the present invention can also be produced, for example, by a method of reacting a precursor of a metal complex and a precursor of a ligand of a metal complex.

The metal complex represented by the formula (1') as one embodiment of the metal complex represented by the formula (1) can be produced, for example, by coupling reaction of a compound represented by the formula (M1-4) described above and a metal complex represented by the formula (M1-8) (the metal complex represented by the formula (M1-8) is one embodiment of the metal complex represented by the formula (1)). This coupling reaction is the same as explained for the compound represented by the formula (M1-1) in which ring A has a group represented by the above-described formula (D-A) or the formula (D-B) as a substituent.

[Chemical Formula 66]

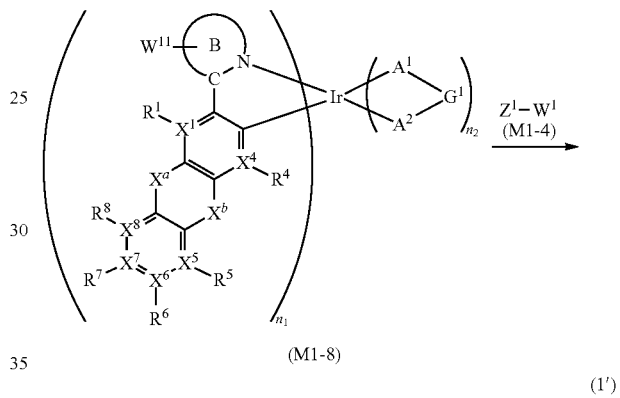

(M1-8) + (M1-4) → (1')

[wherein, $n_1$, $n_2$, $X^1$, $X^4$ to $X^8$, $R^1$, $R^4$ to $R^8$, $X^a$, $X^b$, ring B, $A^1$-$G^1$-$A^2$, $Z^1$ and $W^1$ are as defined above. When there are a plurality of ring B, they may be the same or different.]

The metal complex represented by the formula (M1-8) can be synthesized, for example, by using a compound represented by the formula (M1-3) described above instead of the compound represented by the formula (M1-1) in the step A1 and the step B1 in [Production method 1] of the metal complex represented by the formula (1) described above.

<Production Method of Metal Complex Represented by Formula (2)>

[Production Method 3]

The metal complex represented by the formula (2) as the metal complex of the present invention can be produced, for example, by the same method as [Production method 1] of the metal complex represented by the formula (1) described above.

Specifically, the above-described metal complex can be produced by a method comprising a step A2 of synthesizing a metal complex represented by the formula (M2-2) by using a compound represented by the formula (M2-1) instead of the compound represented by the formula (M1-1) in [Production method 1] of the metal complex represented by the formula (1) described above, and a step B2 of reacting a metal complex represented by the formula (M2-2) with a compound represented by the formula (M2-1) or a precursor of a ligand represented by $A^1$-$G^1$-$A^2$. The step A2 and the step B2 can be carried out by the same methods as the step A1 and the step B1 in [Production method 1] of the metal complex represented by the formula (1) described above, respectively.

[Chemical Formula 67]

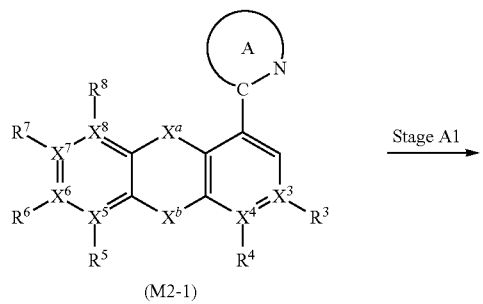

(M2-1)

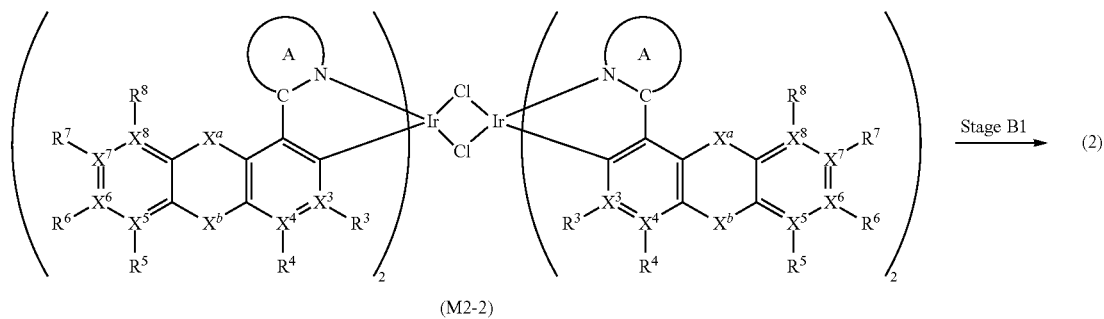

(M2-2)

[wherein, $X^3$ to $X^8$, $R^3$ to $R^8$, $X^a$, $X^b$ and ring A are as defined above.]

When ring A has a group represented by the above-described formula (D-A) or the formula (D-B) as a substituent, the compound represented by the formula (M2-1) can be synthesized, for example, by using a compound represented by the formula (M2-3) instead of the compound represented by the formula (M1-3) in [Production method 1] of the metal complex represented by the formula (1) described above.

[Chemical Formula 68]

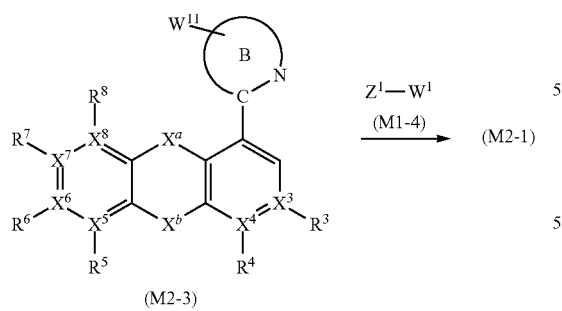

(M2-3)

[wherein, $X^3$ to $X^8$, $R^3$ to $R^8$, $X^a$, $X^b$, ring B, $Z^1$ and $W^1$ are as defined above.]

The compound represented by the formula (M2-3) can be synthesized, for example, by using a compound represented by the formula (M2-5) instead of the compound represented by the formula (M1-5) in [Production method 1] of the metal complex represented by the formula (1) described above.

[Chemical Formula 69]

(M2-5)     (M1-6)     (M2-3)

[wherein, $X^3$ to $X^8$, $R^3$ to $R^8$, $X^a$, $X^b$, $W^3$, $W^4$ and ring B are as defined above.]

When ring A does not have a group represented by the above-described formula (D-A) or the formula (D-B) as a substituent, the compound represented by the formula (M2-1) can be produced, for example, by coupling reaction of a compound represented by the formula (M2-5) and a compound represented by the formula (M1-7). This coupling reaction is the same as explained for the compound represented by the formula (M1-1) in which ring A has a group represented by the above-described formula (D-A) or the formula (D-B) as a substituent.

[Chemical Formula 70]

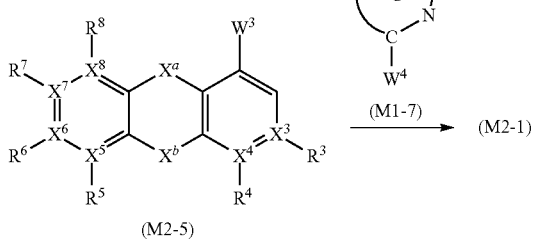

(M2-5)

[wherein, $X^3$ to $X^8$, $R^3$ to $R^8$, $X^a$, $X^b$, $W^3$, $W^4$ and ring C are as defined above.]

[Production Method 4]

The metal complex represented by the formula (2') as one embodiment of the metal complex represented by the formula (2) can be produced, for example, by the same method as [Production method 2] of the metal complex represented by the formula (1) described above.

Specifically, the above-described metal complex can be produced by using a metal complex represented by the formula (M2-8) (the metal complex represented by the formula (M2-8) is one embodiment of the metal complex represented by the formula (2)) instead of the metal complex represented by the formula (M1-8) in [Production method 2] of the metal complex represented by the formula (1) described above. This reaction can be carried out by the same method as the reaction in [Production method 2] of the metal complex represented by the formula (1) described above.

[Chemical Formula 71]

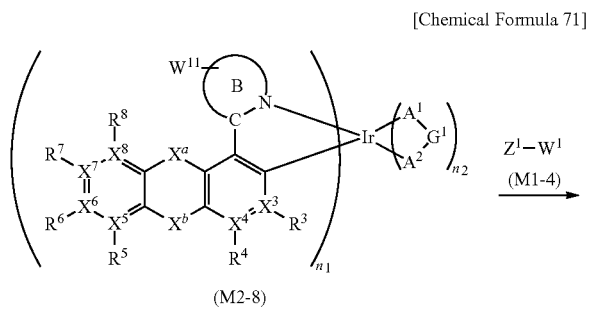

[wherein, $n_1$, $n_2$, $X^3$ to $X^8$, $R^3$ to $R^8$, $X^a$, $X^b$, ring B, $A^1$-$G^1$-$A^2$, $Z^1$ and $W^1$ are as defined above. When there are a plurality of ring B, they may be the same or different.]

The metal complex represented by the formula (M2-8) can be synthesized, for example, by using a compound represented by the formula (M2-3) described above instead of the compound represented by the formula (M1-1) in the step A1 and the step B1 in [Production method 1] of the metal complex represented by the formula (1) described above.

<Production Method of Metal Complex Represented by Formula (3)>

[Production Method 5]

The metal complex represented by the formula (3) as the metal complex of the present invention can be produced, for example, by the same method as [Production method 1] of the metal complex represented by the formula (1) described above.

Specifically, the above-described metal complex can be produced by a method comprising a step A3 of synthesizing a metal complex represented by the formula (M3-2) by using a compound represented by the formula (M3-1) instead of the compound represented by the formula (M1-1) in [Production method 1] of the metal complex represented by the formula (1) described above, and a step B3 of reacting a metal complex represented by the formula (M3-2) with a compound represented by the formula (M3-1) or a precursor of a ligand represented by $A^1$-$G^1$-$A^2$. The step A3 and the step B3 can be carried out by the same methods as the step A1 and the step B1 in [Production method 1] of the metal complex represented by the formula (1) described above, respectively.

[Chemical Formula 72]

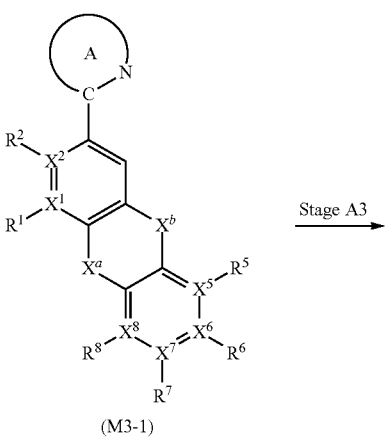

Stage A3

(M3-1)

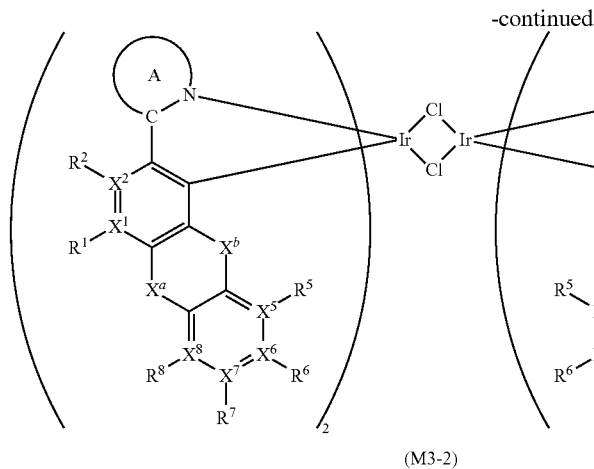
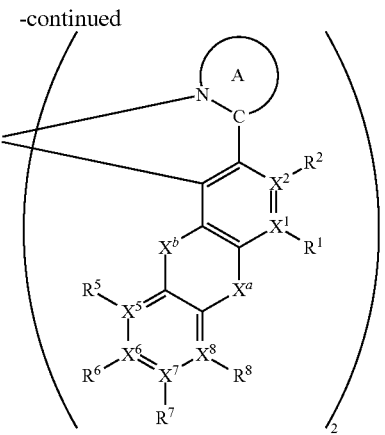

(M3-2)

[wherein, $X^1$, $X^3$, $X^5$ to $X^8$, $R^1$, $R^2$, $R^5$ to $R^8$, $X^a$, $X^b$ and ring A are as defined above.]

When ring A has a group represented by the above-described formula (D-A) or the formula (D-B) as a substituent, the compound represented by the formula (M3-1) can be synthesized, for example, by using a compound represented by the formula (M3-3) instead of the compound represented by the formula (M1-3) in [Production method 1] of the metal complex represented by the formula (1) described above.

[Chemical Formula 73]

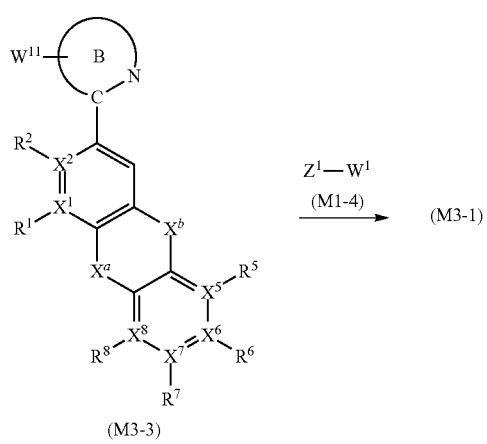

(M3-3)

[wherein, $X^1$, $X^2$, $X^5$ to $X^8$, $R^1$, $R^2$, $R^5$ to $R^8$, $X^a$, $X^b$, ring B, $Z^1$ and $W^1$ are as defined above.]

The compound represented by the formula (M3-3) can be synthesized, for example, by using a compound represented by the formula (M3-5) instead of the compound represented by the formula (M1-5) in [Production method 1] of the metal complex represented by the formula (1) described above.

[Chemical Formula 74]

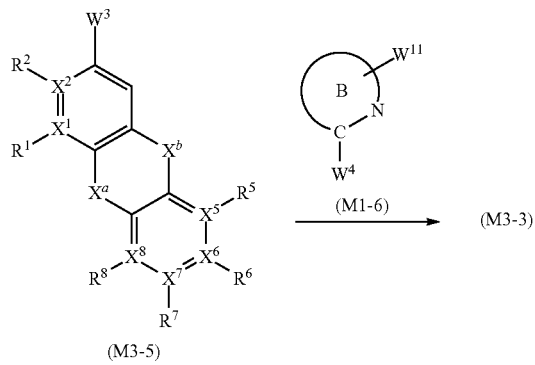

[wherein, $X^1$, $X^2$, $X^5$ to $X^8$, $R^1$, $R^2$, $R^5$ to $R^8$, $X^a$, $X^b$, $W^1$, $W^4$ and ring B are as defined above.]

When ring A does not have a group represented by the above-described formula (D-A) or the formula (D-B) as a substituent, the compound represented by the formula (M3-1) can be produced, for example, by coupling reaction of a compound represented by the formula (M3-5) and a compound represented by the formula (M1-7). This coupling reaction is the same as explained for the compound represented by the formula (M1-1) in which ring A has a group represented by the above-described formula (D-A) or the formula (D-B) as a substituent.

[Chemical Formula 75]

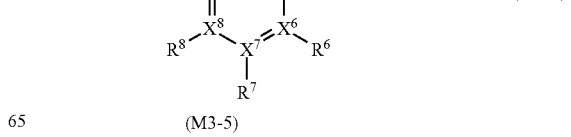

[wherein, $X^1$, $X^2$, $X^5$ to $X^8$, $R^1$, $R^2$, $R^5$ to $R^8$, $X^a$, $X^b$, $W^3$, $W^4$ and ring C are as defined above.].

[Production Method 6]

A metal complex represented by the formula (3') as one embodiment of the metal complex represented by the formula (3) can be produced, for example, by the same method as [Production method 2] of the metal complex represented by the formula (1) described above.

Specifically, the above-described metal complex can be produced by using a metal complex represented by the formula (M3-8) (the metal complex represented by the formula (M3-8) is one embodiment of the metal complex represented by the formula (3)) instead of the metal complex represented by the formula (M1-8) in [Production method 2] of the metal complex represented by the formula (1) described above. This reaction can be carried out by the same method as the reaction in [Production method 2] of the metal complex represented by the formula (1) described above.

[Chemical Formula 76]

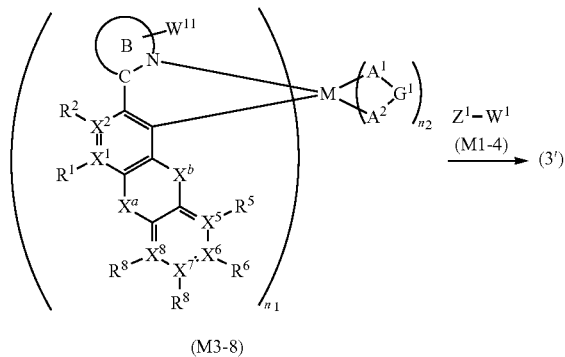

[wherein, $n^1$, $n^2$, $X^1$, $X^2$, $X^5$ to $X^8$, $R^1$, $R^2$, $R^5$ to $R^8$, $X^a$, $X^b$, ring B, $A^1$-$G^1$-$A^2$, $Z^1$ and $W^1$ are as defined above. When there are a plurality of ring B, they may be the same or different.]

The metal complex represented by the formula (M3-8) can be synthesized, for example, by using a compound represented by the formula (M3-3) described above instead of the compound represented by the formula (M1-1) in the step A1 and the step B1 in [Production method 1] of the metal complex represented by the formula (1) described above.

[Coupling Reaction in Production Method 1 to Production Method 6]

In the coupling reaction, catalysts such as a palladium catalyst and the like may be used for promoting the reaction. The palladium catalyst includes, for example, palladium acetate, bis(triphenylphosphine)palladium(II) dichloride, tetrakis(triphenylphosphine)palladium(0), [1,1'-bis(diphenylphosphino)ferrocene]dichloropalladium(II) and tris(dibenzylideneacetone)dipalladium(0).

The palladium catalyst may also be used together with a phosphorus compound such as triphenylphosphine, tri(o-tolyl)phosphine, tri(tert-butyl)phosphine, tricyclohexylphosphine, 1,1'-bis(diphenylphosphino)ferrocene and the like.

When the palladium catalyst is used in the coupling reaction, its amount is usually an effective amount with respect to 1 mol of a compound represented by the formula (M1-3), the formula (M1-4), the formula (M1-4-1a), the formula (M1-4-1b), the formula (M1-4-2a), the formula (M1-4-2b), the formula (M1-5), the formula (M1-6), the formula (M1-7), the formula (M1-8), the formula (M2-3), the formula (M2-5) the formula (M2-8), the formula (M3-3), the formula (M3-5), or the formula (M3-8), and preferably 0.00001 to 10 mol in terms of a palladium element.

In the coupling reaction, a base may be used together, if necessary.

For the compounds, the catalysts and the solvents used in the reactions explained in <Production method of metal complex>, each of them may be used singly or in combination of two or more.

<Composition>

The composition of the present invention comprises at least one material selected from the group consisting of a hole transporting material, a hole injection material, an electron transporting material, an electron injection material, a light emitting material (the light emitting material is different from the metal complex of the present invention), an antioxidant and a solvent, and the metal complex of the present invention.

In the composition of the present invention, the metal complex of the present invention may be contained singly or in combination.

[Host Material]

By a composition comprising the metal complex of the present invention and a host material having at least one function selected from hole injectability, hole transportability, electron injectability and electron transportability, a light emitting device produced by using the metal complex of the present invention has more excellent external quantum efficiency. In the composition of the present invention, a host material may be contained singly or two or more host materials may be contained.

In the composition comprising the metal complex of the present invention and the host material, the content of the metal complex of the present invention is usually 0.01 to 80 parts by weight, preferably 0.05 to 50 parts by weight, more preferably 0.1 to 40 parts by weight, further preferably 0.5 to 35 parts by weight, particularly preferably 1 to 20 parts by weight, when the total amount of the metal complex of the present invention and the host material is 100 parts by weight.

It is preferable that the lowest excited triplet state (Ti) of the host material has energy level equal to or higher than the lowest excited triplet state (Ti) of the metal complex of the present invention because a light emitting device produced by using the composition of the present invention has more excellent external quantum efficiency.

It is preferable that the host material shows solubility in a solvent which is capable of dissolving the metal complex of the present invention from the standpoint of producing a light emitting device produced by using the composition of the present invention by a solution coating process.

The host materials are classified into low molecular weight compounds and polymer compounds.

The low molecular weight compound used as the host material includes, for example, a compound having a carbazole structure, a compound having a triarylamine structure, a compound having a phenanthroline structure, a compound having a triaryltriazine structure, a compound having an azole structure, a compound having a benzothiophene structure, a compound having a benzofuran structure, a compound having a fluorene structure and a compound having a spirofluorene structure. Specific examples of the low molecular weight compound used as the host material include compounds shown below.

[Chemical Formula 77]

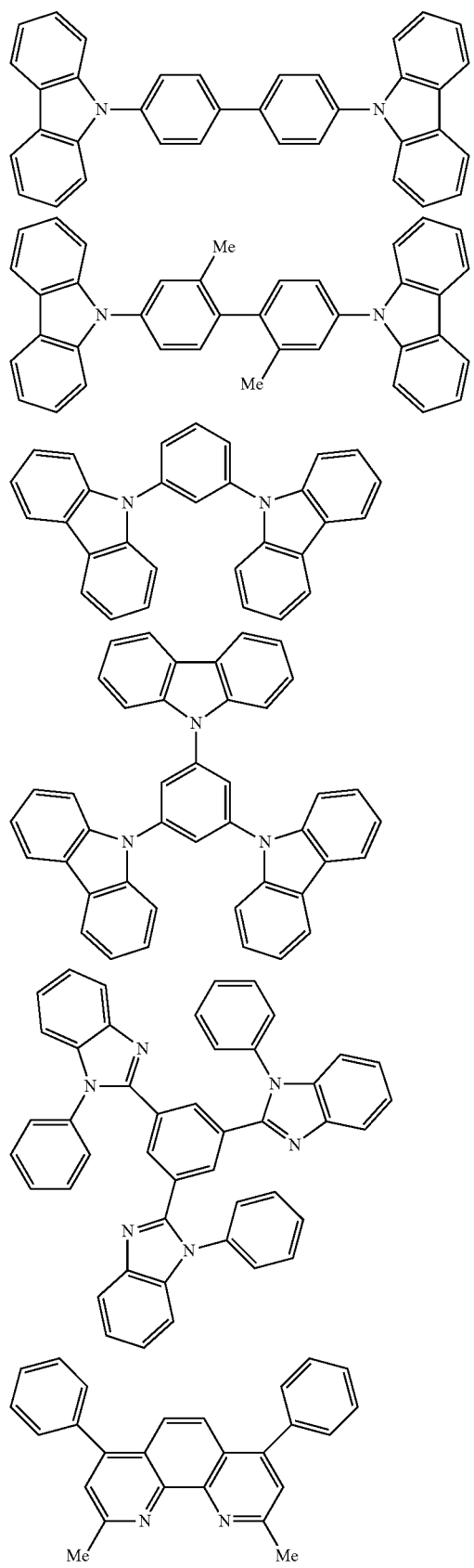

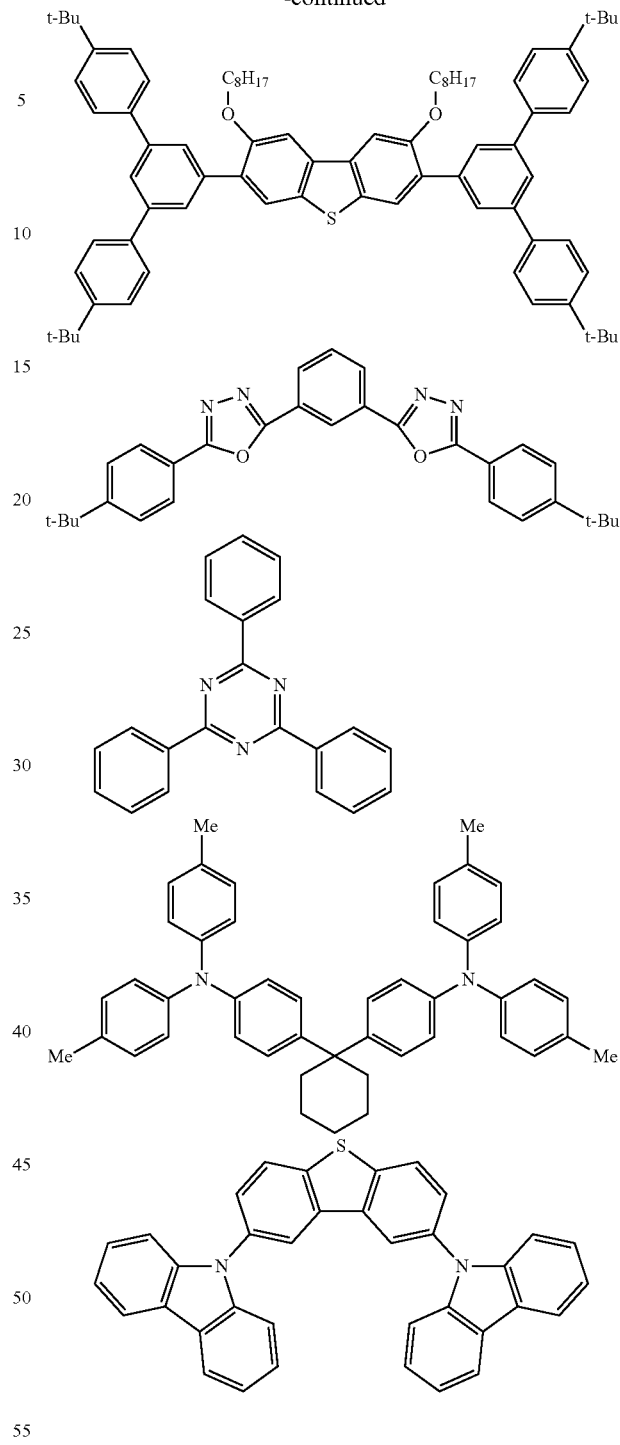

The polymer compound used as a host material includes, for example, polymer compounds as a hole transporting material described later and polymer compounds as an electron transporting material described later.

[Polymer Host]

The polymer compound which is preferable as a host compound (hereinafter, referred to also as "polymer host") will be explained.

The polymer host is preferably a polymer compound comprising a constitutional unit represented by the formula (Y).

The arylene group represented by Ar$^{Y1}$ is more preferably a group represented by the formula (A-1), the formula (A-2), the formulae (A-6) to (A-10), the formula (A-19) or the formula (A-20), further preferably a group represented by the formula (A-1), the formula (A-2), the formula (A-7), the formula (A-9) or the formula (A-19), the foregoing groups each optionally having a substituent.

The divalent heterocyclic group represented by Ar$^{Y1}$ is more preferably a group represented by the formulae (AA-1) to (AA-4), the formulae (AA-10) to (AA-15), the formulae (AA-18) to (AA-21), the formula (A-33) or the formula (A-34), further preferably a group represented by the formula (AA-4), the formula (AA-10), the formula (AA-12), the formula (AA-14) or the formula (AA-33), the foregoing groups each optionally having a substituent.

The more preferable range and the further preferable range of the arylene group and the divalent heterocyclic group in the divalent group in which at least one arylene group and at least one divalent heterocyclic group are bonded directly to each other represented by Ar$^{Y1}$ are the same as the more preferable range and the further preferable range of the arylene group and the divalent heterocyclic group represented by Ar$^{Y1}$ described above, respectively.

"The divalent group in which at least one arylene group and at least one divalent heterocyclic group are bonded directly to each other" includes, for example, groups represented by the following formulae, and each of them optionally has a substituent.

[Chemical Formula 78]

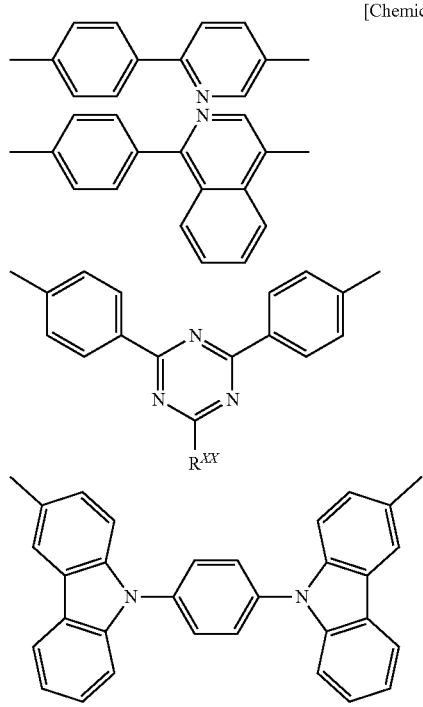

[wherein, R$^{XX}$ represents a hydrogen atom, an alkyl group, a cycloalkyl group, an aryl group or a monovalent heterocyclic group, the foregoing groups each optionally having a substituent.]

R$^{XX}$ is preferably an alkyl group, a cycloalkyl group or an aryl group, the foregoing groups each optionally having a substituent.

The substituent which the group represented by Ar$^{Y1}$ optionally has is preferably an alkyl group, a cycloalkyl group or an aryl group, the foregoing groups each optionally further having a substituent.

The constitutional unit represented by the formula (Y) includes, for example, constitutional units represented by the formulae (Y-1) to (Y-10), and from the standpoint of the luminance life of the light emitting device using the composition comprising the polymer host and the metal complex of the present invention, the preferable are constitutional units represented by the formula (Y-1), (Y-2) or (Y-3), from the standpoint of electron transportability, the preferable are constitutional units represented by the formulae (Y-4) to (Y-7), and from the standpoint of hole transportability, the preferable are constitutional units represented by the formulae (Y-8) to (Y-10).

[Chemical Formula 79]

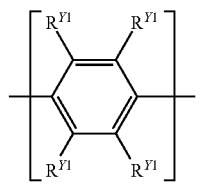

(Y-1)

[wherein, R$^{Y1}$ represents a hydrogen atom, an alkyl group, a cycloalkyl group, an alkoxy group, a cycloalkoxy group, an aryl group or a monovalent heterocyclic group, the foregoing groups each optionally having a substituent. The plurality of R$^{Y1}$ may be the same or different, and adjacent R$^{Y1}$s may be combined together to form a ring together with the atoms to which they are attached.]

R$^{Y1}$ is preferably a hydrogen atom, an alkyl group, a cycloalkyl group or an aryl group, the foregoing groups each optionally having a substituent.

It is preferable that the constitutional unit represented by the formula (Y-1) is a constitutional unit represented by the formula (Y-1').

[Chemical Formula 80]

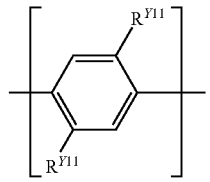

(Y-1')

[wherein, R$^{Y11}$ represents an alkyl group, a cycloalkyl group, an alkoxy group, a cycloalkoxy group, an aryl group or a monovalent heterocyclic group, the foregoing groups each optionally having a substituent. The plurality of R$^{Y1}$ may be the same or different.]

R$^{Y11}$ is preferably an alkyl group, a cycloalkyl group or an aryl group, more preferably an alkyl group or a cycloalkyl group, the foregoing groups each optionally having a substituent.

[Chemical Formula 81]

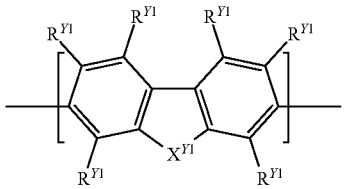
(Y-2)

[wherein, $R^{Y1}$ represents the same meaning as described above. $X^{Y1}$ represents a group represented by —C($R^{Y2}$)$_2$—, —C($R^{Y2}$)=C($R^2$)— or —C($R^{Y2}$)$_2$—C($R^{Y2}$)$_2$—. $R^{Y2}$ represents a hydrogen atom, an alkyl group, a cycloalkyl group, an alkoxy group, a cycloalkoxy group, an aryl group or a monovalent heterocyclic group, the foregoing groups each optionally having a substituent. The plurality of $R^{Y2}$ may be the same or different, and these $R^{Y2}$s may be combined together to form a ring together with the atoms to which they are attached.]

$R^{Y2}$ is preferably an alkyl group, a cycloalkyl group, an aryl group or a monovalent heterocyclic group, more preferably an alkyl group a cycloalkyl group or an aryl group, the foregoing groups each optionally having a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, the foregoing groups each optionally having a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formulae (Y-A1) to (Y-A5), more preferably a group represented by the formula (Y-A4), the foregoing groups each optionally having a substituent.

[Chemical Formula 82]

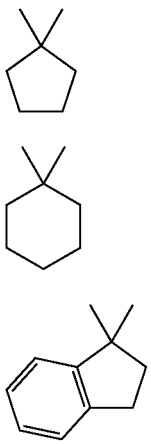

(Y-A1)

(Y-A2)

(Y-A3)

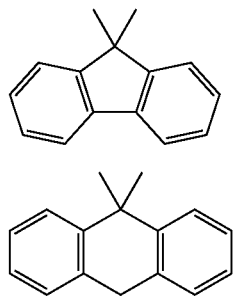

(Y-A4)

(Y-A5)

Regarding the combination of two $R^{Y2}$s in the group represented by —C($R^{Y2}$)—C($R^{Y2}$)— in $X^{Y1}$, it is preferable that the both are an alkyl group or cycloalkyl group, or one is an alkyl group or a cycloalkyl group and the other is an aryl group, the foregoing groups each optionally having a substituent.

Four $R^{Y2}$s in the group represented by —C($R^{Y2}$)$_2$—C($R^{Y2}$)$_2$— in $X^{Y1}$ are preferably an alkyl group or a cycloalkyl group optionally having a substituent. The plurality of $R^{Y2}$ may be combined together to form a ring together with the atoms to which they are attached, and when the groups $R^{Y2}$ form a ring, the group represented by —C($R^{Y2}$)$_2$—C($R^{Y2}$)$_2$— is preferably a group represented by the formulae (Y-B1) to (Y-B5), more preferably a group represented by the formula (Y-B3), the foregoing groups each optionally having a substituent.

[Chemical Formula 83]

(Y-B1)

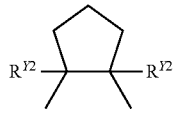
(Y-B2)

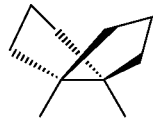
(Y-B3)

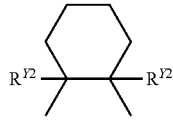
(Y-B4)

(Y-B5)

[wherein, $R^{Y2}$ are as defined above.]

It is preferable that the constitutional unit represented by the formula (Y-2) is a constitutional unit represented by the formula (Y-2′).

[Chemical Fomula 84]

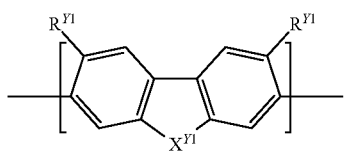

(Y-2')

[wherein, $R^{Y1}$ and $X^{Y1}$ are as defined above.]

[Chemical Fomula 85]

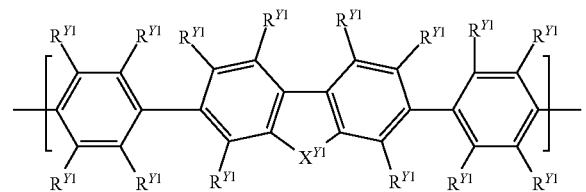

(Y-3)

[wherein, $R^{Y1}$ and $X^{Y1}$ are as defined above.]

It is preferable that the constitutional unit represented by the formula (Y-3) is a constitutional unit represented by the formula (Y-3').

[Chemical Fomula 86]

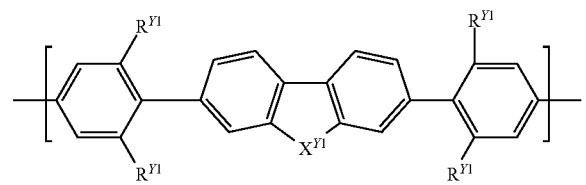

(Y-3')

[wherein, $R^{Y1}$ and $X^{Y1}$ are as defined above.]

[Chemical Formula 87]

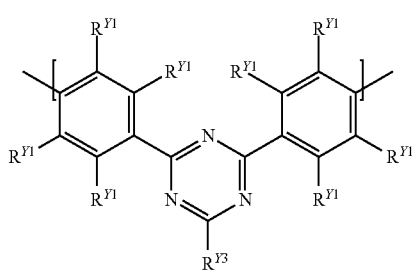

(Y-4)

-continued

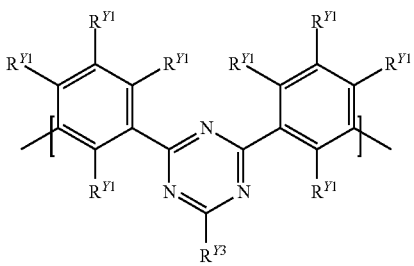

(Y-5)

[Chemical Formula 88]

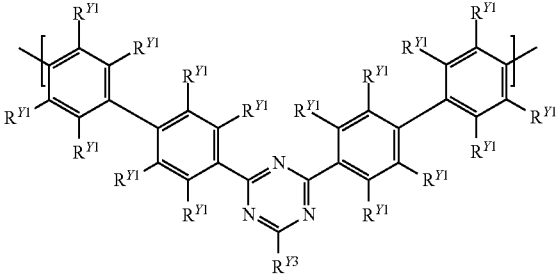

(Y-6)

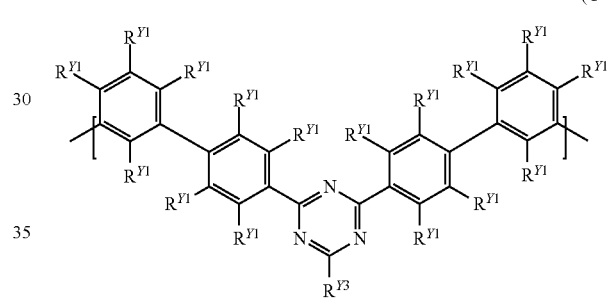

(Y-7)

[wherein, $R^{Y1}$ represents the same meaning as described above. $R^{Y3}$ represents a hydrogen atom, an alkyl group, a cycloalkoxy group, an alkoxy group, a cycloalkoxy group or an aryl group or a monovalent heterocyclic group, the foregoing groups each optionally having a substituent.]

$R^{Y3}$ is preferably an alkyl group, a cycloalkyl group, an alkoxy group, a cycloalkoxy group, an aryl group or a monovalent heterocyclic group, more preferably an aryl group, the foregoing groups each optionally having a substituent.

It is preferable that the constitutional unit represented by the formula (Y-4) is a constitutional unit represented by the formula (Y-4'). It is preferable that the constitutional unit represented by the formula (Y-6) is a constitutional unit represented by the formula (Y-6').

[Chemical Formula 89]

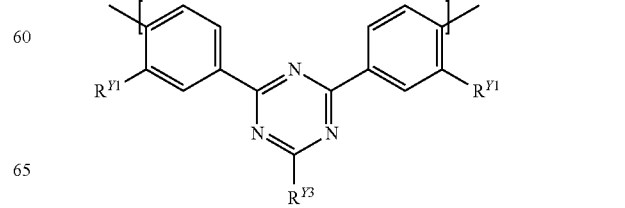

(Y-4')

(Y-6′)

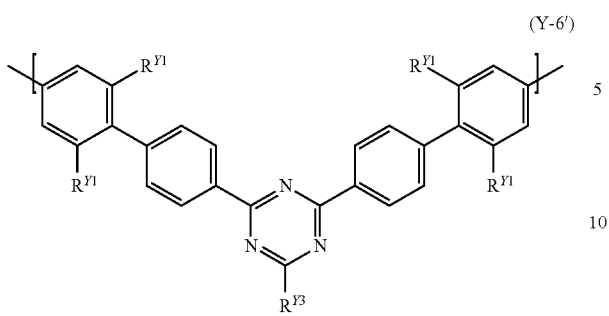

[wherein, $R^{Y1}$ and $R^{Y3}$ are as defined above.]

[Chemical Formula 90]

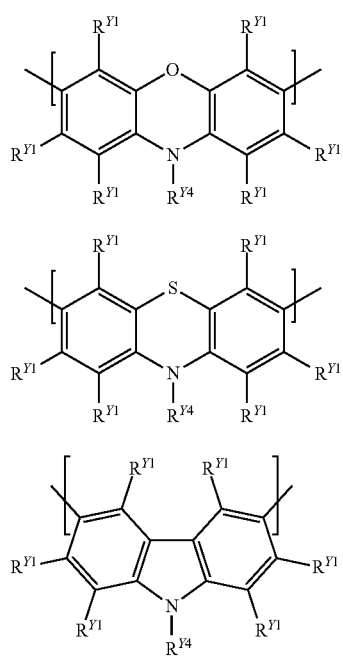

(Y-8)

(Y-9)

(Y-10)

[wherein, $R^{Y1}$ are as defined above. $R^{Y4}$ represents a hydrogen atom, an alkyl group, a cycloalkyl group, an alkoxy group, a cycloalkoxy group, an aryl group or a monovalent heterocyclic group, the foregoing groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, the foregoing groups each optionally having a substituent.

The constitutional unit represented by the formula (Y) includes, for example, a constitutional unit composed of an arylene group represented by the formulae (Y-101) to (Y-121), a constitutional unit composed of a divalent heterocyclic group represented by the formulae (Y-201) to (Y-206), and a constitutional unit composed of a divalent group in which at least one arylene group and at least one divalent heterocyclic group are bonded directly to each other represented by the formulae (Y-301) to (Y-304).

[Chemical Formula 91]

(Y-101)

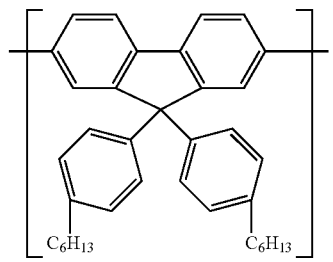

(Y-102)

(Y-103)

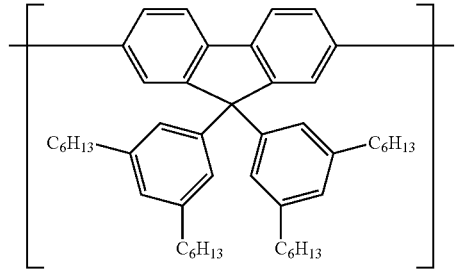

[Chemical Formula 92]

(Y-104)

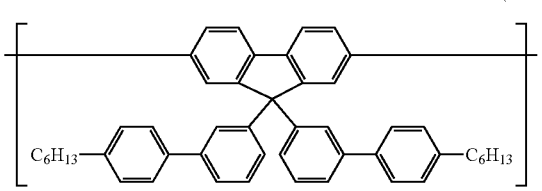

(Y-105)

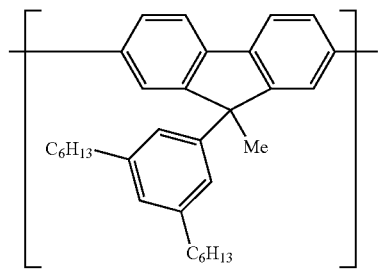

[Chemical Formula 93]

(Y-106)

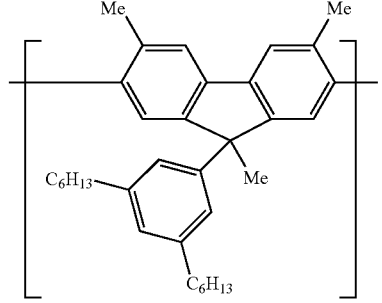

(Y-107) 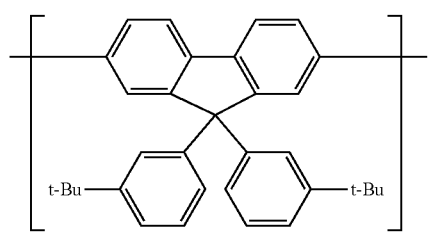
(Y-108) 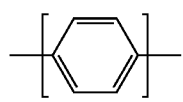
(Y-109) 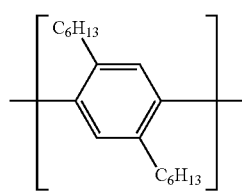
[Chemical Formula 94]
(Y-110) 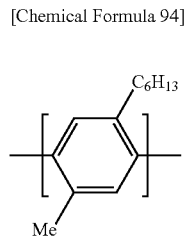
(Y-111) 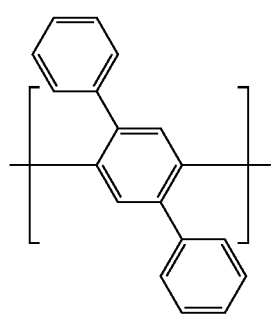
(Y-112) 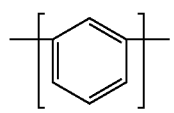
(Y-113) 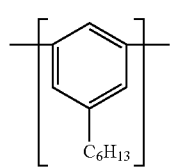
(Y-114) 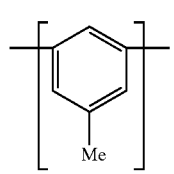
[Chemical Formula 95]
(Y-115) 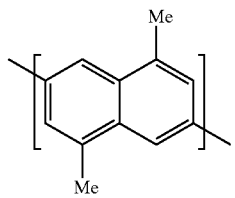
(Y-116) 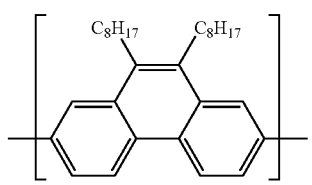
(Y-117) 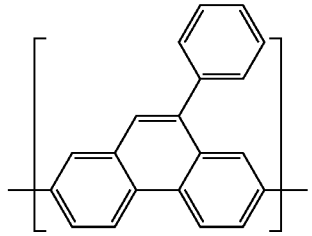
(Y-118) 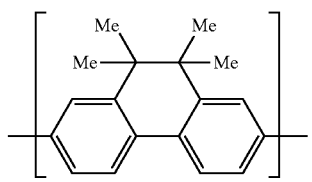
[Chemical Formula 96]
(Y-119) 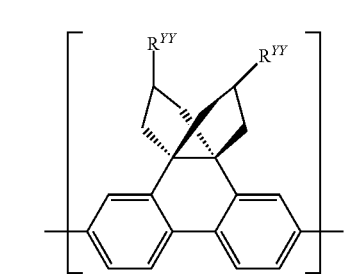
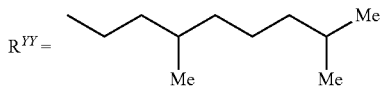
(Y-120) 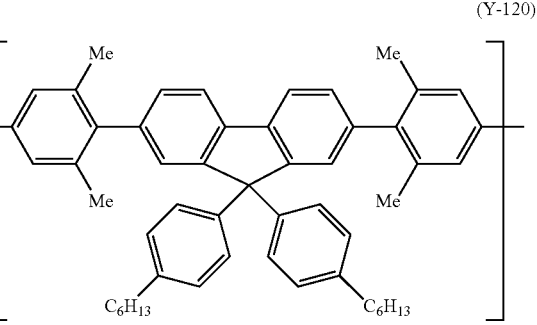

(Y-121)
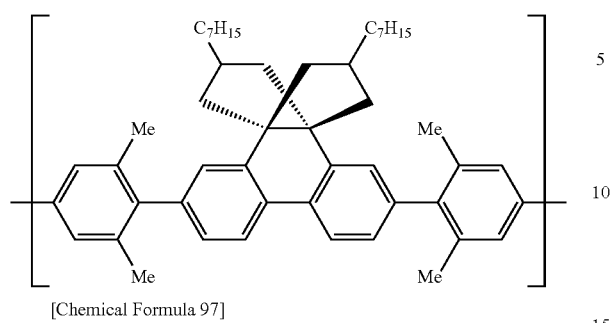
[Chemical Formula 97]
(Y-201)
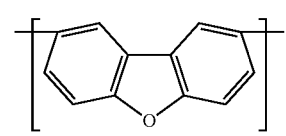
(Y-202)
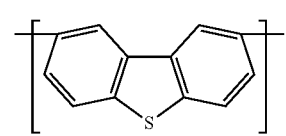
(Y-203)
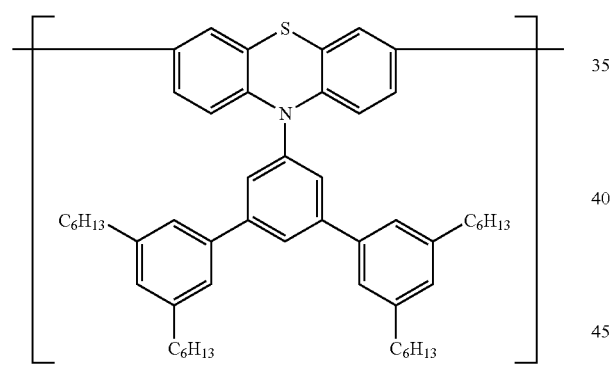
(Y-204)
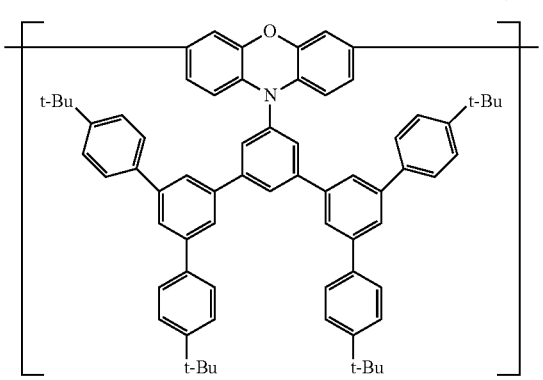
[Chemical Formula 98]
(Y-205)
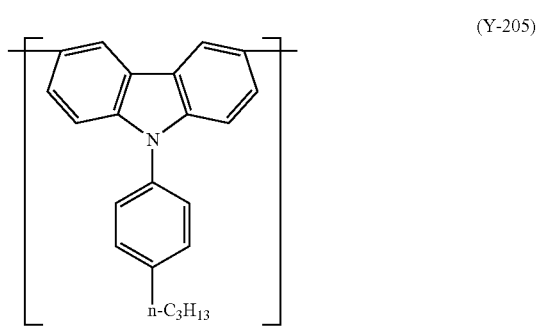
(Y-206)
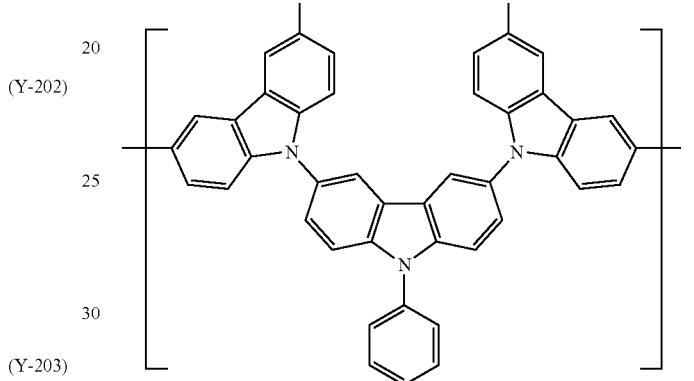
(Y-301)
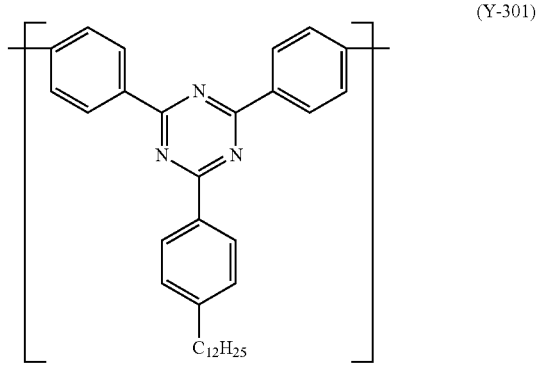
[Chemical Formula 99]
(Y-302)
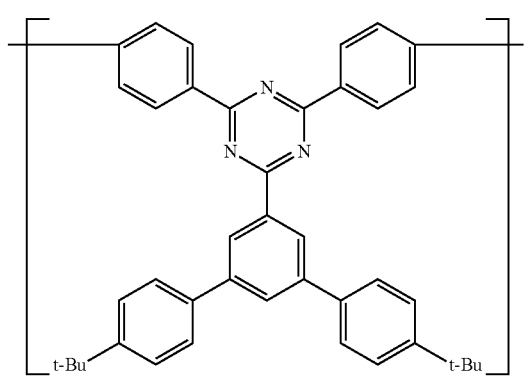

-continued (Y-303)

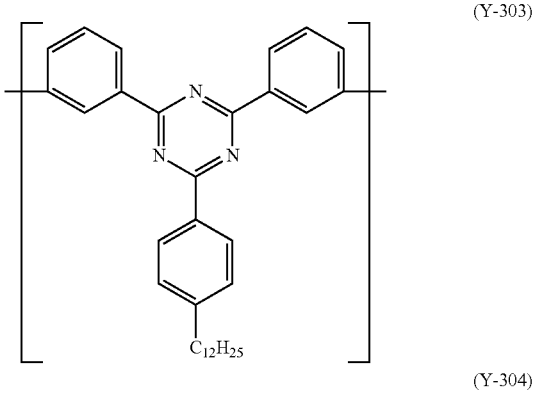

(Y-304)

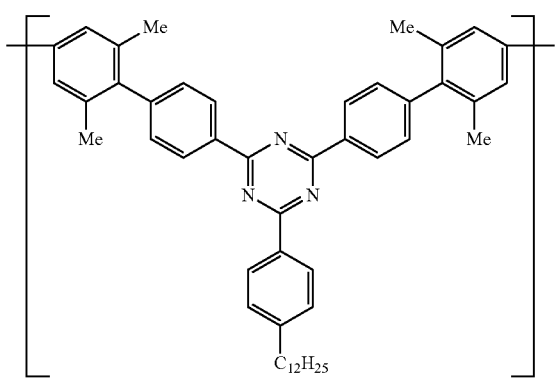

The amount of the constitutional unit represented by the formula (Y) in which $Ar^{Y1}$ is an arylene group is preferably 0.5 to 100 mol %, more preferably 60 to 95 mol % with respect to the total amount of constitutional units contained in a polymer compound, because the luminance life of a light emitting device by using a composition comprising a polymer host and the metal complex of the present invention is excellent.

The amount of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 30 mol %, more preferably 3 to 20 mol % with respect to the total amount of constitutional units contained in a polymer compound, because the charge transportability of a light emitting device by using a composition comprising a polymer host and the metal complex of the present invention is excellent.

The constitutional unit represented by the formula (Y) may be contained only singly or two or more units thereof may be contained in the polymer host.

It is preferable that the polymer host further comprises a constitutional unit represented by the following formula (X), because then hole transportability is excellent.

[Chemical Formula 100]

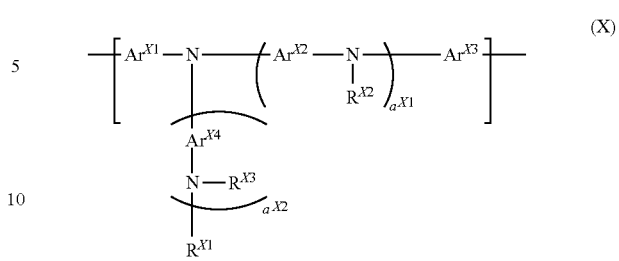

(X)

[wherein, $a^{X1}$ and $a^{X2}$ each independently represent an integer of 0 or more. $Ar^{X1}$ and $Ar^{X3}$ each independently represent an arylene group or a divalent heterocyclic group, the foregoing groups each optionally having a substituent. $Ar^{X2}$ and $Ar^{X4}$ each independently represent an arylene group, a divalent heterocyclic group or a divalent group in which at least one arylene group and at least one divalent heterocyclic group are bonded directly to each other, the foregoing groups each optionally having a substituent. $R^{X1}$, $R^{X2}$ and $R^{X3}$ each independently represent a hydrogen atom, an alkyl group, a cycloalkyl group, an aryl group or a monovalent heterocyclic group, the foregoing groups each optionally having a substituent.]

$a^{X1}$ is preferably 2 or less, more preferably 1 because the luminance life of the light emitting device by using the composition comprising the polymer host and the metal complex of the present invention is excellent.

$a^{X2}$ is preferably 2 or less, more preferably 0 because the luminance life of the light emitting device by using the composition comprising the polymer host and the metal complex of the present invention is excellent.

$R^{X1}$, $R^{X2}$ and $R^{X3}$ are preferably an alkyl group, a cycloalkyl group, an aryl group or a monovalent heterocyclic group, more preferably an aryl group, the foregoing groups each optionally having a substituent.

The arylene group represented by $Ar^{X1}$ and $Ar^{X3}$ is more preferably a group represented by the formula (A-1) or the formula (A-9), further preferably a group represented by the formula (A-1), the foregoing groups each optionally having a substituent.

The divalent heterocyclic group represented by $Ar^{X1}$ and $Ar^{X3}$ is more preferably a group represented by the formula (AA-1), the formula (AA-2) or the formulae (AA-7) to (AA-26), the foregoing groups each optionally having a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formulae (A-9) to (A-11) or the formula (A-19), the foregoing groups each optionally having a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by Ar$^{X1}$ and Ar$^{X3}$, respectively.

The divalent group in which at least one arylene group and at least one divalent heterocyclic group are bonded directly to each other represented by Ar$^{X2}$ and Ar$^{X4}$ includes the same groups as the divalent group in which at least one arylene group and at least one divalent heterocyclic group are bonded directly to each other represented by Ar$^{Y1}$ in the formula (Y).

Ar$^{X2}$ and Ar$^{X4}$ are preferably an arylene group optionally having a substituent.

The substituent which the group represented by Ar$^{X1}$ to Ar$^{X4}$ and R$^{X1}$ to R$^{X3}$ optionally has is preferably an alkyl group, a cycloalkyl group or an aryl group, the foregoing groups each optionally further having a substituent.

The constitutional unit represented by the formula (X) is preferably a constitutional unit represented by the formulae (X-1) to (X-7), more preferably a constitutional unit represented by the formulae (X-1) to (X-6), further preferably a constitutional unit represented by the formulae (X-3) to (X-6).

[Chemical Formula 101]

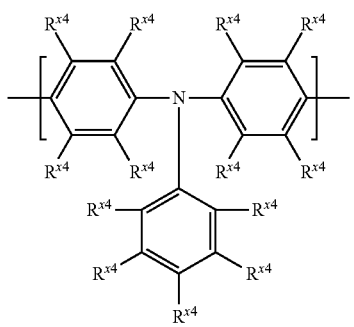
(X-1)

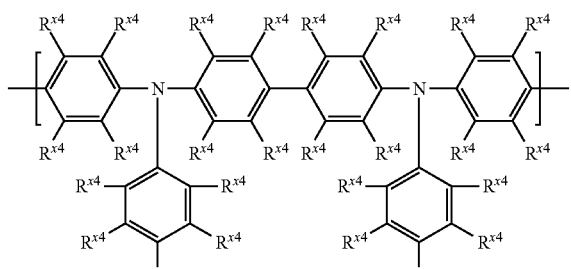
(X-2)

[Chemical Formula 102]

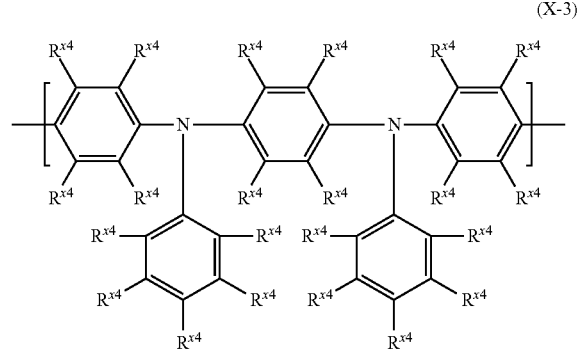
(X-3)

[Chemical Formula 103]

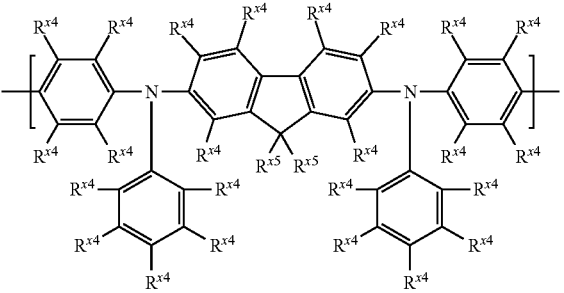
(X-4)

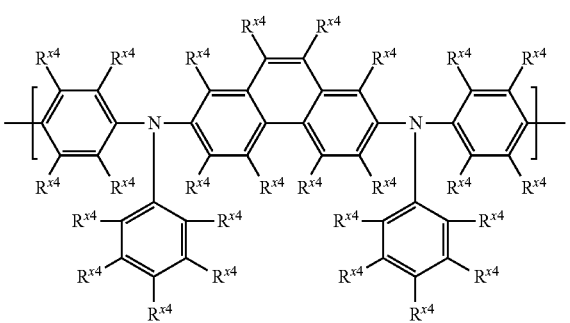
(X-5)

[Chemical Formula 104]

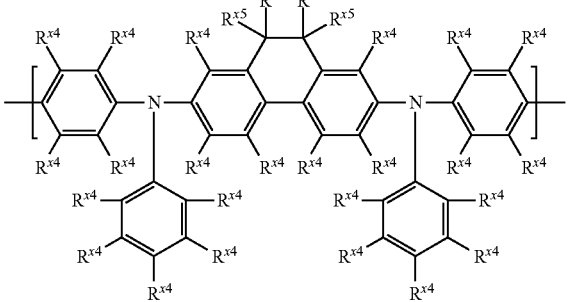
(X-6)

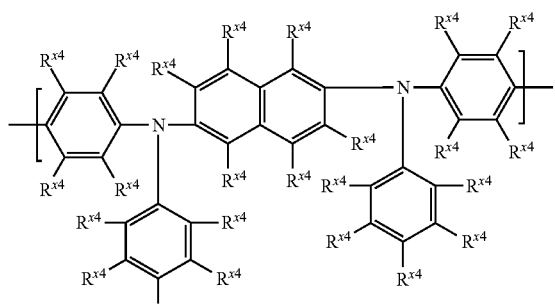
(X-7)

[wherein, R$^{X4}$ and R$^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, the foregoing groups each optionally having a substituent. The plurality of R$^{X4}$ may be the same or different. The plurality of R$^{X5}$ may be the same or different, and adjacent groups $R^{X5}$ may be combined together to form a ring together with the atoms to which they are attached.]

The amount of the constitutional unit represented by the formula (X) is preferably 0.1 to 50 mol %, more preferably 1 to 40 mol %, further preferably 2 to 30 mol % with respect to the total amount of constitutional units contained in a polymer host, because hole transportability is excellent.

The constitutional unit represented by the formula (X) includes, for example, constitutional units represented by the formulae (X1-1) to (X1-11), preferably constitutional units represented by the formulae (X1-3) to (X1-10).

[Chemical Formula 105]

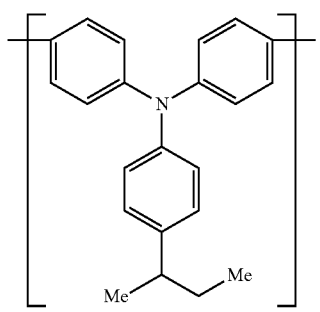
(X1-1)

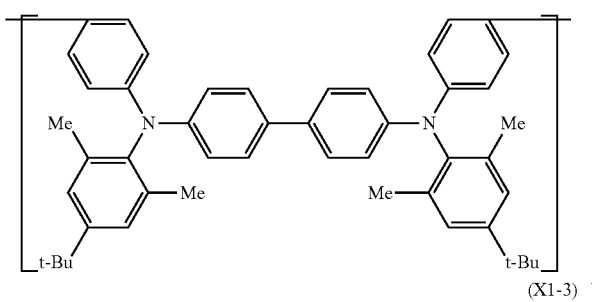
(X1-2)

[Chemical Formula 106]

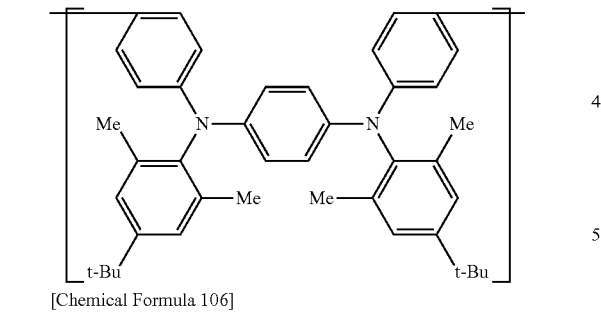
(X1-3)

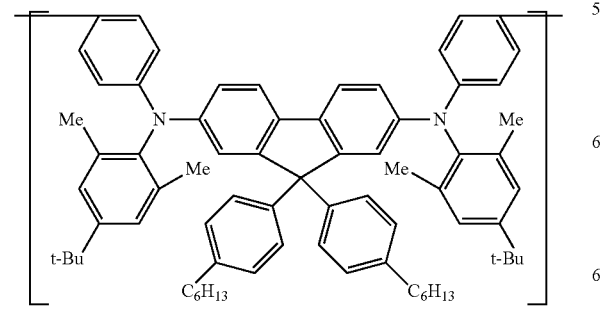
(X1-4)

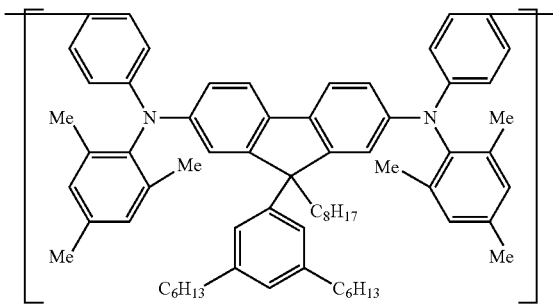
(X1-5)

[Chemical Formula 107]

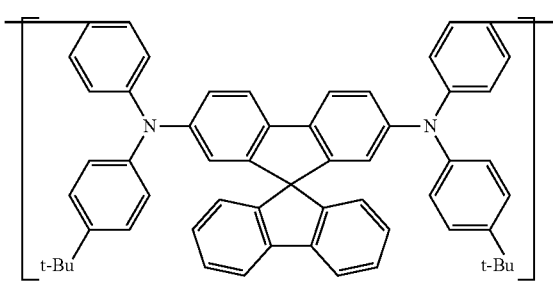
(X1-6)

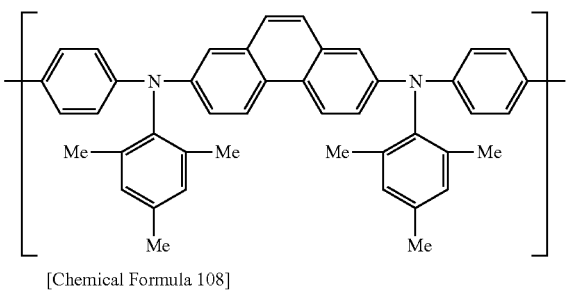
(X1-7)

[Chemical Formula 108]

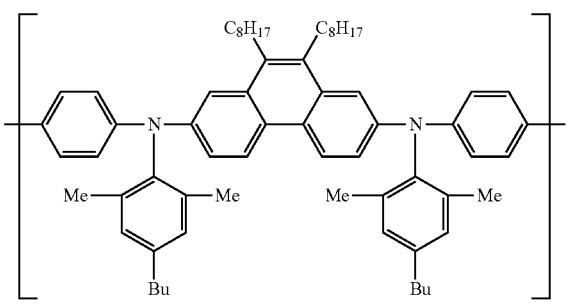
(X1-8)

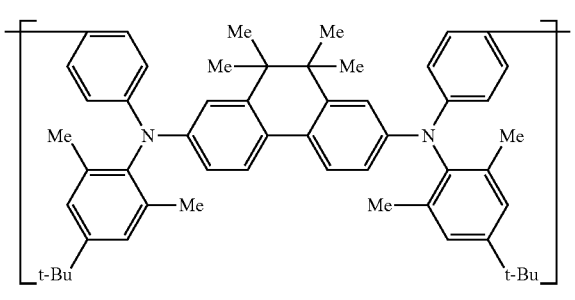
(X1-9)

-continued

[Chemical Formula 109]

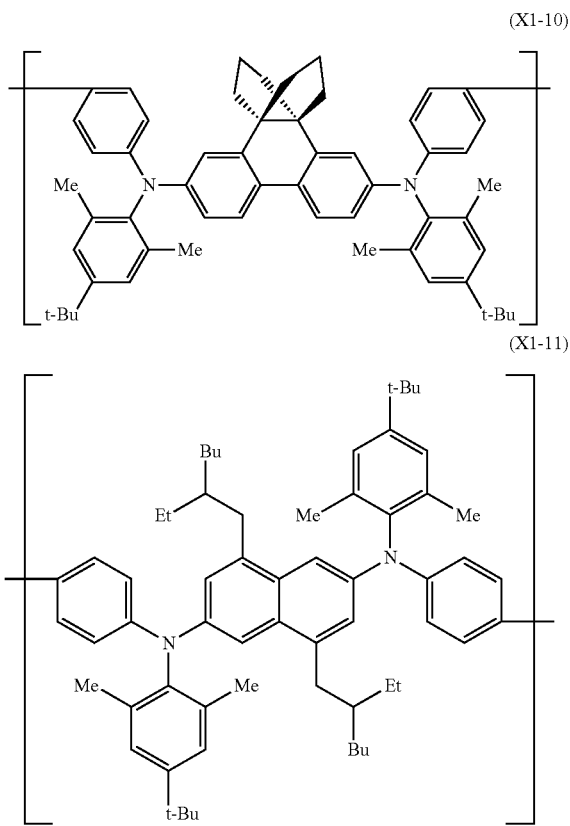

The constitutional unit represented by the formula (X) may be contained only singly or two or more units thereof may be contained in the polymer host.

Examples of the polymer host include polymer compounds P-1 to P-7 in "Table 1" below.

TABLE 1

| | constitutional unit and mole fraction thereof | | | | |
|---|---|---|---|---|---|
| | formula (Y) | | | formula (X) | |
| polymer compound | formulae (Y-1) to (Y-3) p | formulae (Y-4) to (Y-7) q | formulae (Y-8) to (Y-10) r | formulae (X-1) to (X-7) s | other t |
| P-1 | 0.1 to 99.9 | 0.1 to 99.9 | 0 | 0 | 0 to 30 |
| P-2 | 0.1 to 99.9 | 0 | 0.1 to 99.9 | 0 | 0 to 30 |
| P-3 | 0.1 to 99.9 | 0 | 0 | 0.1 to 99.9 | 0 to 30 |
| P-4 | 0.1 to 99.8 | 0.1 to 99.8 | 0 | 0.1 to 99.8 | 0 to 30 |
| P-5 | 0.1 to 99.8 | 0.1 to 99.8 | 0.1 to 99.8 | 0 | 0 to 30 |
| P-6 | 0.1 to 99.8 | 0 | 0.1 to 99.8 | 0.1 to 99.8 | 0 to 30 |
| P-7 | 0.1 to 99.7 | 0.1 to 99.7 | 0.1 to 99.7 | 0.1 to 99.7 | 0 to 30 |

[In the table, p, q, r, a and t represent the mole fraction of each constitutional unit. p+q+r+s+t=100, and 100≥p+q+r+s≥70. Other constitutional unit denotes a constitutional unit other than the constitutional unit represented by the formula (Y) and the constitutional unit represented by the formula (X).]

好ましい。

The polymer host may be any of a block copolymer, a random copolymer, an alternating copolymer or a graft copolymer, and may also be another embodiment, and from the above-described standpoint is preferably a copolymer obtained by copolymerizing a plurality of raw material monomers.

<Production Method of Polymer Host>

The polymer host can be produced by using a known polymerization method described in Chem. Rev., vol. 109, pp. 897-1091 (2009) and the like, and the production methods include methods for causing polymerization by a coupling reaction using a transition metal catalyst such as the Suzuki reaction, the Yamamoto reaction, the Buchwald reaction, the Stille reaction, the Negishi reaction and the Kumada reaction.

In the above-described polymerization methods, the monomer charging method includes a method in which the total amount of monomers is charged in a lump into the reaction system, a method in which a part of monomers is charged and reacted, then, the remaining monomers are charged in a lump, continuously or in divided doses, a method in which monomers are charged continuously or in divided doses, and the like.

The transition metal catalyst is not particularly restricted and includes a palladium catalyst and a nicked catalyst.

For the post treatment of the polymerization reaction, known methods, for example, a method of removing water-soluble impurities by liquid-separation, a method in which the reaction solution after the polymerization reaction is added to a lower alcohol such as methanol to cause deposition of a precipitate which is then filtrated before drying, and other methods, are used each singly or combined. When the purity of the polymer host is low, the polymer host can be purified by usual methods such as, for example, recrystallization, reprecipitation, continuous extraction with a Soxhlet extractor and column chromatography.

The composition comprising the metal complex of the present invention and a solvent (hereinafter, referred to as "ink" in some cases) is suitable for fabrication of a light emitting device using a printing method such as an inkjet printing method and a nozzle printing method.

The viscosity of the ink may be adjusted depending on the kind of the printing method, and when a solution goes through a discharge apparatus such as in an inkjet printing method, the viscosity is preferably in the range of 1 to 20 mPa·s at 25° C. for preventing curved aviation and clogging in discharging.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as tetrahydrofuran, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol; alcohol solvents such as isopropanol and cyclohexanol; sulfoxide solvents such as dimethyl sulfoxide; and amide solvents such as N-methyl-2-pyrrolidone and N,N-dimethylformamide. These solvents may be used singly or two or more of them may be used in combination.

In the ink, the compounding amount of the above-described solvent is usually 1000 to 100000 parts by weight, preferably 2000 to 20000 parts by weight with respect to 100 parts by weight of the metal complex of the present invention.

[Hole Transporting Material]

The hole transporting material is classified into low molecular weight compounds and polymer compounds, and polymer compounds are preferable, polymer compounds having a crosslinkable group are more preferable.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene, trinitrofluorenone and the like, preferably fullerene.

In the composition of the present invention, the compounding amount of the hole transporting material is usually 1 to 400 parts by weight, preferably 5 to 150 parts by weight with respect to 100 parts by weight of the metal complex of the present invention.

The hole transporting material may be used singly or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof.

The polymer compound includes, for example, polyphenylene, polyfluorene and derivatives thereof. These polymer compounds may be doped with a metal.

In the composition of the present invention, the compounding amount of the electron transporting material is usually 1 to 400 parts by weight, preferably 5 to 150 parts by weight with respect to 100 parts by weight of the metal complex of the present invention.

The electron transporting material may be used singly or two or more electron transporting materials may be used in combination.

[Hole Injection Material and Electron Injection Material]

The hole injection material and the electron injection material are each classified into low molecular weight compounds and polymer compounds. The hole injection material and the electron injection material optionally has a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising a group represented by the formula (X) in the main chain or side chain.

In the composition of the present invention, the compounding amounts of the hole injection material and the electron injection material are each usually 1 to 400 parts by weight, preferably 5 to 150 parts by weight with respect to 100 parts by weight of the metal complex of the present invention.

The hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1\times10^{-9}$ S/cm to $1\times10^{3}$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

[Light Emitting Material]

The light emitting material (the light emitting material is different form the metal complex of the present invention) is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof, and, triplet light emitting complexes having iridium, platinum or europium as the central metal.

The polymer compound includes, for example, polymer compounds comprising a phenylene group, a naphthalenediyl group, a fluorenediyl group, a phenanthrenediyl group, a dihydrophenanthrenediyl group, a group represented by the formula (X), a carbazolediyl group, a phenoxazinediyl group, a phenothiazinediyl group, an anthracenediyl group, a pyrenediyl group and the like.

The light emitting material may comprise a low molecular weight compound and a polymer compound, and preferably, comprises a triplet light emitting complex and a polymer compound.

The triplet light emitting complex includes, for example, metal complexes listed below.

[Chemical Formula 110]
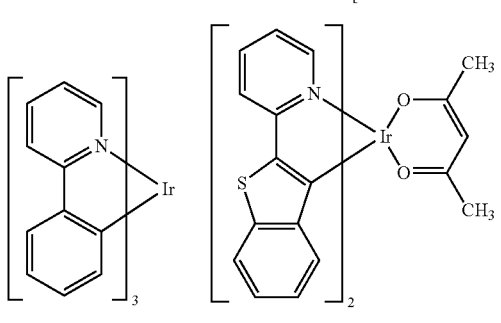
Ir(ppy)₃     Btp₂Ir(acac)
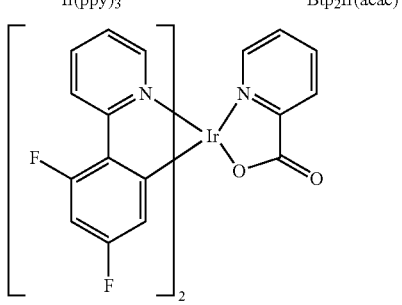
FIrpic
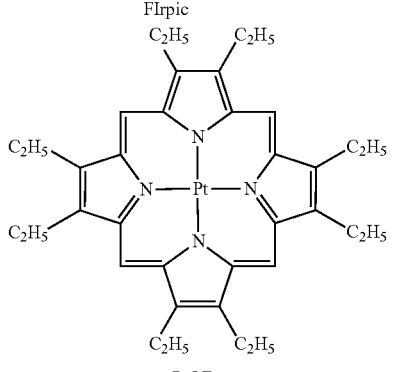
PtOEp
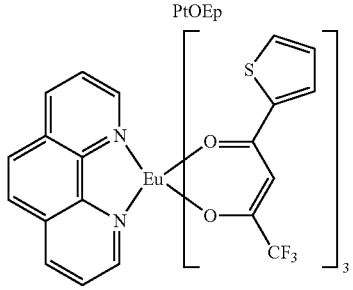
Eu(TTA)₃phen
[Chemical Formula 111]
COM-1
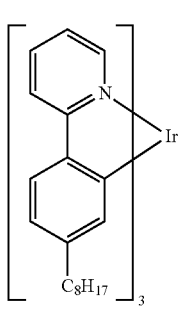
COM-2
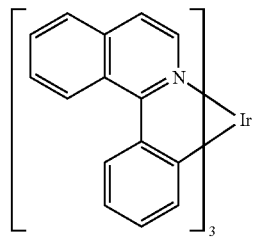
COM-3
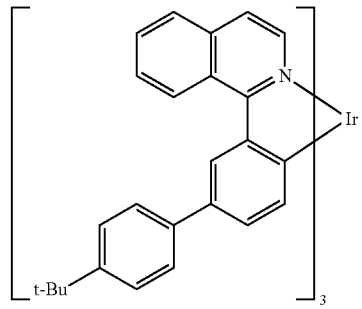
COM-4
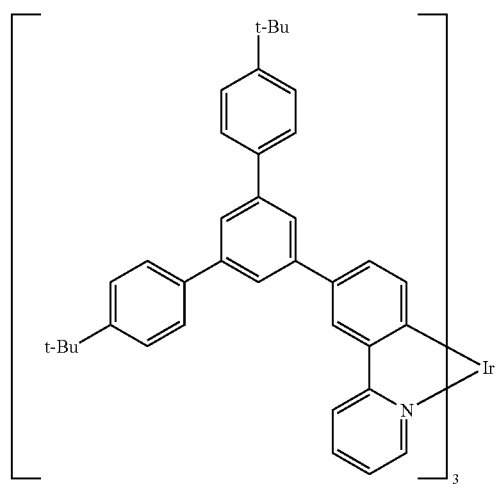
COM-5
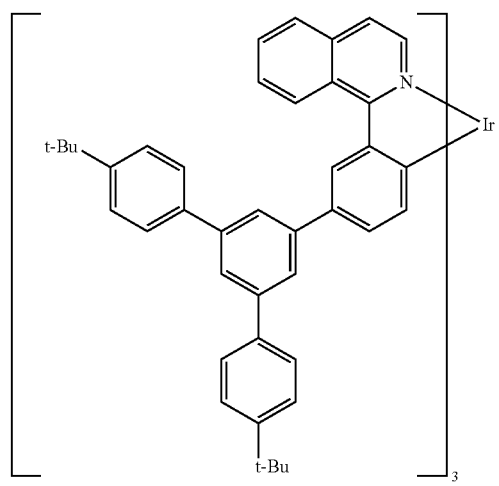
In the composition of the present invention, the compounding amount of the above-described light emitting material is usually 0.1 to 400 parts by weight with respect to 100 parts by weight of the metal complex of the present invention.

[Antioxidant]

The antioxidant may advantageously be one which is soluble in the same solvent as for the metal complex of the present invention and does not disturb light emission and charge transportation, and the examples thereof include phenol antioxidants and phosphorus-based antioxidants.

In the composition of the present invention, the compounding amount of the antioxidant is usually 0.001 to 10 parts by weight with respect to 100 parts by weight of the metal complex of the present invention.

The antioxidant may be used singly or two or more antioxidants may be used in combination.

<Film>

The film comprises the metal complex of the present invention.

The film also includes an insolubilized film produced by insolubilizing the metal complex of the present invention in a solvent by crosslinking. The insolubilized film is a film produced by crosslinking the metal complex of the present invention by an external stimulus such as heating and light irradiation. The insolubilized film can be suitably used for lamination of a light emitting device because the insolubilized film is substantially insoluble in a solvent.

The heating temperature for crosslinking the film is usually 25 to 300° C., and because the external quantum efficiency is improved, preferably 50 to 250° C., more preferably 150 to 200° C.

The kind of light used in light irradiation for crosslinking the film includes, for example, ultraviolet light, near-ultraviolet light and visible light.

The film is suitable as a hole transporting layer, a hole injection layer or a light emitting layer in a light emitting device and is suitable as a light emitting layer.

The film can be fabricated, for example, by a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method or a nozzle coating method, using the ink.

The thickness of the film is usually 1 nm to 10 μm.

<Light Emitting Device>

The light emitting device of the present invention is a light emitting device produced by using the metal complex of the present invention, and may be a light emitting device comprising the metal complexes of the present invention, may be a light emitting device comprising a cross-linked body obtained by intramolecular or intermolecular crosslinking of the metal complexes of the present invention, or may be a light emitting device comprising a cross-linked body obtained by intramolecular and intermolecular crosslinking of the metal complexes of the present invention.

The constitution of the light emitting device of the present invention comprises, for example, electrodes consisting of an anode and a cathode, and a layer produced by using the metal complex of the present invention disposed between the electrodes.

[Layer Constitution]

The layer produced by using the metal complex of the present invention is usually at least one selected from a light emitting layer, a hole transporting layer, a hole injection layer, an electron transporting layer and an electron injection layer, preferably a light emitting layer. These layers comprise a light emitting material, a hole transporting material, a hole injection material, an electron transporting material and an electron injection material, respectively. These layers can be formed by the same method as the above-described film fabrication using inks prepared by dissolving a light emitting material, a hole transporting material, a hole injection material, an electron transporting material and an electron injection material, respectively, in the solvent described above.

The light emitting device comprises a light emitting layer between an anode and a cathode. The light emitting device of the present invention preferably comprises at least one of a hole injection layer and a hole transporting layer between an anode and a light emitting layer from the standpoint of hole injectability and hole transportability, and preferably comprises at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the above-described hole transporting materials, electron transporting materials, light emitting materials, hole injection materials and electron injection materials, respectively, in addition to the metal complex of the present invention.

When the material of a hole transporting layer, the material of an electron transporting layer and the material of a light emitting layer are dissolved in a solvent which is used in forming a layer adjacent to the hole transporting layer, the electron transporting layer and the light emitting layer, respectively, in fabrication of a light emitting device, it is preferable that the materials have a crosslinkable group to avoid dissolution of the materials in the solvent. After forming the layers using the materials having a crosslinkable group, the layers can be insolubilized by crosslinking the crosslinkable group.

Methods of forming respective layers such as a light emitting layer, a hole transporting layer, an electron transporting layer, a hole injection layer and an electron injection layer in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order and the number of layers to be laminated and the thickness of each layer may be controlled in view of external quantum efficiency and device life.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium*tin*oxide (ITO) and indium*zinc*oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

Measurement of LC-MS was carried out according to the following method.

A measurement sample was dissolved in chloroform or tetrahydrofuran so as to give a concentration of about 2 mg/mL, and about 1 μL of the solution was injected into LC-MS (manufactured by Agilent Technologies, trade name: 1100LCMSD). As the mobile phase of LC-MS, acetonitrile and tetrahydrofuran were used while changing the ratio thereof and allowed to flow at a flow rate of 0.2 mL/min. As the column, L-column 2 ODS (3 μm) (manufactured by Chemicals Evaluation and Research Institute, internal diameter: 2.1 mm, length: 100 mm, particle size: 3 μm) was used.

Measurement of NMR was carried out according to the following method.

5 to 10 mg of a measurement sample was dissolved in deuterated chloroform ($CDCl_3$), deuterated tetrahydrofuran (THF-de) or deuterated methylene chloride ($CD_2Cl_2$), and measurement was performed using an NMR apparatus (manufactured by Varian, Inc., trade name: MERCURY 300 or manufactured by Bruker, trade name: AVANCE600).

As the index of the purity of a compound, a value of the high performance liquid chromatography (HPLC) area percentage was used. This value is a value in high performance liquid chromatography (HPLC, manufactured by Shimadzu Corp., trade name: LC-20A) at 254 nm, unless otherwise state. In this operation, the compound to be measured was dissolved in tetrahydrofuran or chloroform so as to give a concentration of 0.01 to 0.2 wt %, and depending on the concentration, 1 to 10 μL of the solution was injected into HPLC. As the mobile phase of HPLC, acetonitrile and tetrahydrofuran were used and allowed to flow at a flow rate of 1 mL/min as gradient analysis of acetonitrile/tetrahydrofuran=100/0 to 0/100 (volume ratio). As the column, Kaseisorb LC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

TLC-MS measurement was performed by the following method.

A measurement sample was dissolved in a solvent selected from toluene, tetrahydrofuran or chloroform at an optional concentration, the solution was applied on a TLC plate for DART (manufactured by Techno Applications, YSK5-100), and measurement was performed using TLC-MS (manufactured by JEOL Ltd., trade name: JMS-T100TD (The AccuTOF TLC)). The temperature of a helium gas in measurement was controlled in a range of 200 to 400° C.

PLQY and emission spectra were measured by the following method.

A metal complex was dissolved in xylene so as to give a concentration of 0.0008% by weight. The resultant xylene solution was charged into a 1 cm square quartz cell, then, oxygen was deaerated by bubbling with a nitrogen gas, to fabricate a measurement sample. The PLOY and emission spectrum of the resultant measurement sample were measured using an absolute PL quantum yield measuring apparatus (automatically controlled electrically driven monochrome light source type) (C9920-02G, manufactured by Hamamatsu Photonics K.K.), and the full width at half maximum of an emission spectrum (hereinafter, also referred to as "FNHM") was calculated from the resultant emission spectrum. Specifically, FWHM is calculated from a wavelength at which the normalized emission intensity is 0.5 when the emission intensity of the maximum peak in an emission spectrum of a metal complex is normalized to 1.0. When there are three or more wavelengths showing a normalized emission intensity of 0.5, it is calculated from a wavelength which is the shortest wavelength and a wavelength which is the longest wavelength. The excitation wavelength was 380 nm.

<Synthesis Example 1> Synthesis of Compound L1

[Chemical Formula 112]

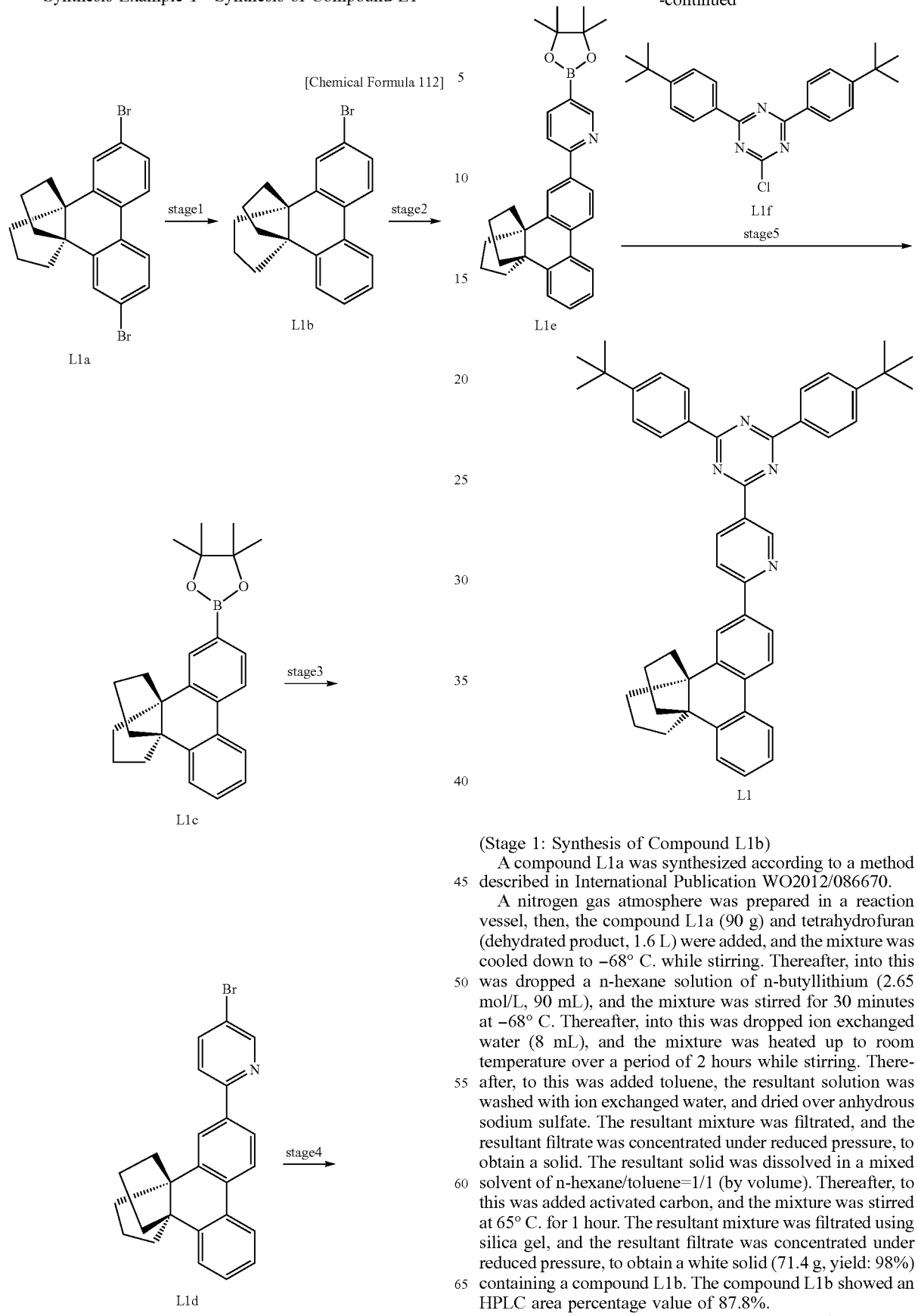

(Stage 1: Synthesis of Compound L1b)

A compound L1a was synthesized according to a method described in International Publication WO2012/086670.

A nitrogen gas atmosphere was prepared in a reaction vessel, then, the compound L1a (90 g) and tetrahydrofuran (dehydrated product, 1.6 L) were added, and the mixture was cooled down to −68° C. while stirring. Thereafter, into this was dropped a n-hexane solution of n-butyllithium (2.65 mol/L, 90 mL), and the mixture was stirred for 30 minutes at −68° C. Thereafter, into this was dropped ion exchanged water (8 mL), and the mixture was heated up to room temperature over a period of 2 hours while stirring. Thereafter, to this was added toluene, the resultant solution was washed with ion exchanged water, and dried over anhydrous sodium sulfate. The resultant mixture was filtrated, and the resultant filtrate was concentrated under reduced pressure, to obtain a solid. The resultant solid was dissolved in a mixed solvent of n-hexane/toluene=1/1 (by volume). Thereafter, to this was added activated carbon, and the mixture was stirred at 65° C. for 1 hour. The resultant mixture was filtrated using silica gel, and the resultant filtrate was concentrated under reduced pressure, to obtain a white solid (71.4 g, yield: 98%) containing a compound L1b. The compound L1b showed an HPLC area percentage value of 87.8%.

TLC-MS (DART positive): m/z=339 [M+H]$^+$

¹H-NMR (CD$_2$Cl$_2$, 300 MHz): δ (ppm)=7.86 (dd, 1H), 7.79 (d, 1H), 7.54 (d, 1H), 7.41-7.20 (m, 4H), 2.22-2.12 (m, 4H), 2.01-1.90 (m, 4H), 1.73-1.58 (m, 2H), 1.52-1.39 (m, 2H).

(Stage 2: Synthesis of Compound L1c)

A nitrogen gas atmosphere was prepared in a reaction vessel, then, the compound L1b (71.4 g), bis(pinacolato) diboron (80.2 g), [1,1'-bis(diphenylphosphino)ferrocene]palladium(II) dichloride dichloromethane adduct (10.3 g), potassium acetate (62.0 g) and 1,2-dimethoxyethane (631 mL) were added, and the mixture was stirred at 80° C. for 4 hours. The resultant reaction liquid was cooled down to room temperature, then, toluene (950 mL) was added, and the mixture was filtrated through a filter paved with Celite, and the resultant filtrate was concentrated under reduced pressure. Thereafter, to this were added a mixed solvent of hexane/toluene=1:1 (by volume) (630 mL) and activated carbon, and the mixture was stirred at 70° C. for 1 hour. The resultant mixture was filtrated through a filter paved with Celite, and the resultant filtrate was concentrated under reduced pressure, to obtain a solid. The resultant solid was crystallized using a mixed solvent of toluene and acetonitrile, to obtain a compound L1c (52.1 g, yield: 64%) as a white solid. The resultant compound L1c showed an HPLC area percentage value of 98.1%.

TLC-MS (DART positive): m/z=387 [M+H]$^+$

¹H-NMR (CD$_2$Cl$_2$, 300 MHz): δ (ppm)=7.94-7.88 (m, 2H), 7.77 (d, 1H), 7.59 (dd, 1H), 7.39 (dd, 1H), 7.28 (dt, 1H), 7.21 (dt, 1H), 2.24-2.12 (m, 4H), 2.02-1.90 (m, 4H), 1.72-1.57 (m, 2H), 1.48-1.33 (m, 14H).

(Stage 3: Synthesis of Compound L1d)

A nitrogen gas atmosphere was prepared in a reaction vessel, then, the compound L1c (47.1 g), 2,5-dibromopyridine (30.6 g), tetrakis(triphenylphosphine)palladium(0) (2.82 g), toluene (731 mL), tetrahydrofuran (366 mL), tert-butanol (488 mL), ion exchanged water (244 mL) and a 40 wt % tetrabutylammonium hydroxide aqueous solution (316 g) were added, and the mixture was stirred at 50° C. for 21 hours. The resultant reaction liquid was cooled down to room temperature, then, toluene was added, and the resultant organic layer was washed with ion exchanged water, and dried over anhydrous magnesium sulfate. The resultant mixture was filtrated, and the resultant filtrate was concentrated under reduced pressure, to obtain a solid. The resultant solid was dissolved in a mixed solvent of toluene/chloroform=1:2 (by volume), and the mixture was stirred at 60° C., then, filtrated through a filter paved with silica gel, and the resultant filtrate was concentrated under reduced pressure, to obtain a solid. The resultant solid was crystallized using a mixed solvent of chloroform and methanol, to obtain a compound L1d (44.1 g, yield: 87%) as a white solid. The resultant compound L1d showed an HPLC area percentage value of 97.8%.

TLC-MS (DART positive): m/z=416 [M+H]$^+$

¹H-NMR (CD$_2$Cl$_2$, 300 MHz): δ (ppm)=8.72 (dd, 1H), 8.03 (d, 1H), 7.99 (d, 1H), 7.93 (dd, 1H), 7.88 (dd, 1H), 7.81 (dd, 1H), 7.68 (dd, 1H), 7.40 (dd, 1H), 7.29 (dt, 1H), 7.23 (dt, 1H), 2.28-2.14 (m, 4H), 2.07-1.93 (m, 4H), 1.74-1.62 (m, 2H), 1.51-1.39 (m, 2H).

(Stage 4: Synthesis of Compound L1e)

A nitrogen gas atmosphere was prepared in a reaction vessel, then, the compound L1d (41.1 g), bis(pinacolato)diboron (37.6 g), [1,1'-bis(diphenylphosphino)ferrocene]palladium(II) dichloride dichloromethane adduct (4.8 g), potassium acetate (29.0 g) and 1,2-dimethoxyethane (296 mL) were added, and the mixture was stirred at 80° C. for 3.5 hours. The resultant reaction liquid was cooled down to room temperature, then, toluene (593 mL) was added, and the mixture was filtrated through a filter paved with Celite, and the resultant filtrate was concentrated under reduced pressure. Thereafter, to this were added a mixed solvent of hexane/toluene=1:2 (by volume) and activated carbon, and the mixture was stirred at 70° C. for 2 hours. The resultant mixture was filtrated through a filter paved with Celite, and the resultant filtrate was concentrated under reduced pressure, to obtain a solid. The resultant solid was crystallized using a mixed solvent of toluene and acetonitrile, to obtain a compound L1e (32.6 g, yield: 71%) as a white solid. The resultant compound L1e showed an HPLC area percentage value of 99.5%.

TLC-MS (DART positive): m/z=464 [M+H]$^+$

¹H-NMR (CD$_2$Cl$_2$, 300 MHz): δ (ppm)=8.94 (dd, 1H), 8.10-8.07 (m, 2H), 8.00 (d, 1H), 7.94 (dd, 1H), 7.89 (dd, 1H), 7.73 (dd, 1H), 7.40 (dd, 1H), 7.32-7.20 (m, 2H), 2.30-2.15 (m, 4H), 2.09-1.94 (m, 4H), 1.75-1.60 (m, 2H), 1.51-1.39 (m, 2H), 1.35 (s, 12H).

(Stage 5: Synthesis of Compound L1)

A compound L1f was synthesized according to a method described in JP-A No. 2008-179617.

A nitrogen gas atmosphere was prepared in a light-shielded reaction vessel, then, the compound L1e (19.6 g), the compound L1f (19.28 g), tetrakis(triphenylphosphine)palladium(0) (980 mg), toluene (233 mL) and a 20 wt % tetraethylammonium hydroxide aqueous solution (124.6 g) were added, and the mixture was stirred at 70° C. for 3.5 hours. The resultant reaction liquid was cooled down to room temperature, then, toluene was added, and the resultant solution was washed with ion exchanged water, then, dried over anhydrous sodium sulfate. The resultant mixture was filtrated, and the resultant filtrate was concentrated under reduced pressure, to obtain a solid. To the resultant solid were added a mixed solvent of n-heptane/toluene=1:1 (by volume) and activated carbon, and the mixture was stirred for 30 minutes at 55° C. The resultant mixture was filtrated through a filter paved with Celite, and the resultant filtrate was concentrated under reduced pressure, to obtain a solid. The resultant solid was crystallized using a mixed solvent of toluene and ethanol, then, dried under reduced pressure, to obtain a compound L1 (25.6 g, yield: 89%) as a white solid. The compound L1 showed an HPLC area percentage value of 99.5% or more.

TLC-MS (DART positive): m/z=681 [M+H]$^+$

¹H-NMR (CD$_2$Cl$_2$, 300 MHz): δ (ppm)=10.01 (d, 1H), 9.09 (d, 1H), 8.71 (d, 4H), 8.28 (s, 1H), 8.10-7.98 (m, 4H), 7.64 (d, 4H), 7.44 (dd, 1H), 7.36-7.24 (m, 2H), 2.37-2.30 (m, 2H), 2.27-2.19 (m, 2H), 2.16-1.97 (m, 4H), 1.79-1.63 (m, 2H), 1.56-1.42 (m, 20H).

<Example 1> Synthesis of Metal Complex M1
[Chemical Formula 113]
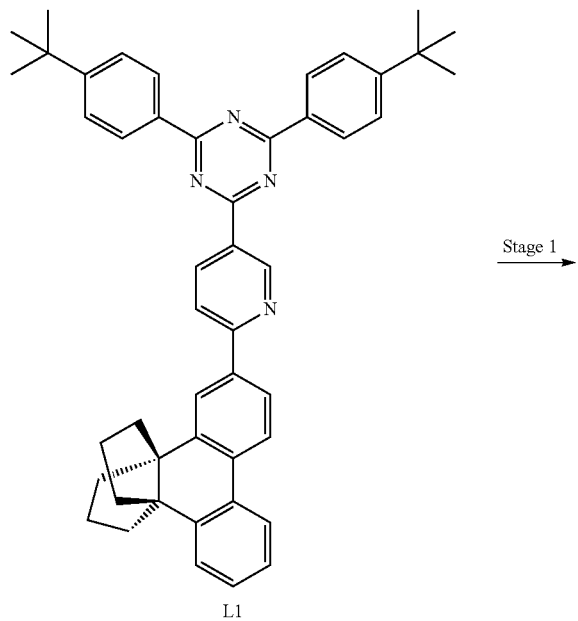
L1
Stage 1 →
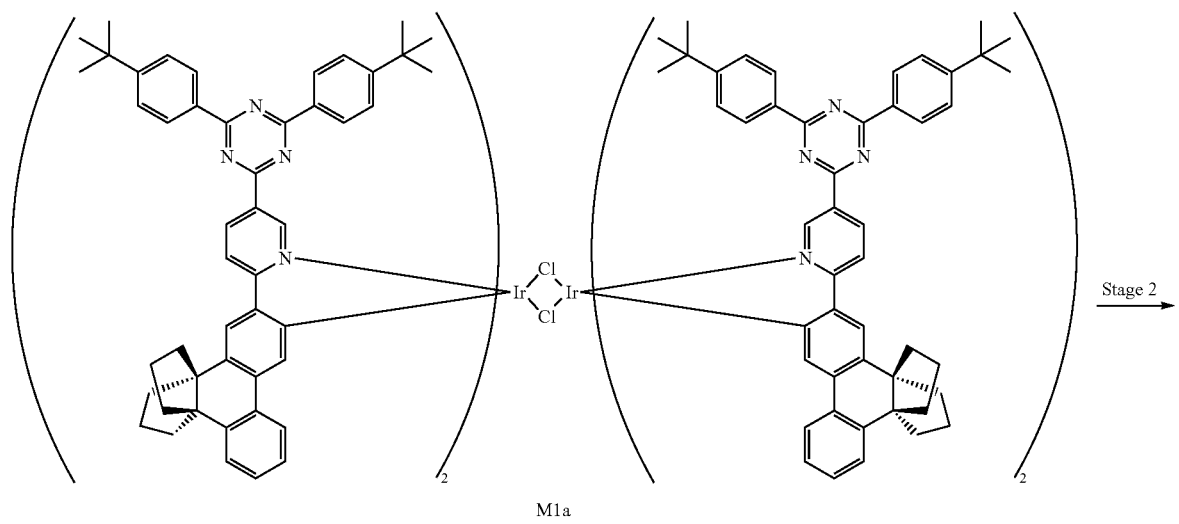
M1a
Stage 2 →

-continued

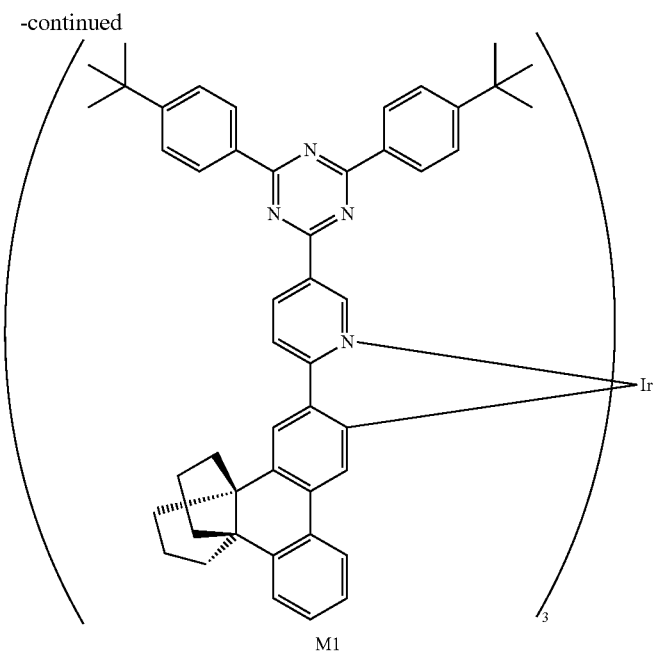

M1

(Stage 1: Synthesis of Metal Complex M1a)

A nitrogen gas atmosphere was prepared in a light-shielded reaction vessel, then, the compound L1 (11.33 g) and 2-ethoxyethanol (1085 mL) were added, and the mixture was heated up to 80° C. Thereafter, into this was dropped iridium(III) chloride n-hydrate (2.55 g) dissolved in ion exchanged water (362 mL), then, the mixture was stirred at 105° C. for 19 hours. The resultant reaction liquid was heated, and the solvent was distilled off until the amount of the reaction liquid was about 700 mL. Thereafter, to this was added 2-ethoxyethanol (380 mL), and the mixture was stirred at 133° C. for 64 hours. The resultant reaction liquid was cooled down to room temperature, then, added to ethanol (1628 mL), and the mixture was stirred for 1.5 hours. The resultant mixture was filtrated, and the resultant residue was dissolved in dichloromethane, then, the solution was washed with ion exchanged water, and dried over anhydrous sodium sulfate. The resultant mixture was filtrated, and the resultant filtrate was concentrated under reduced pressure, to obtain a solid. The resultant solid was dried under reduced pressure overnight at 50° C., to obtain a red solid (9.57 g) containing a metal complex M1a. This operation was repeated, to obtain a necessary amount of the red solid containing the metal complex M1a.

(Stage 2: Synthesis of Metal Complex M1)

A nitrogen gas atmosphere was prepared in a light-shielded reaction vessel, then, the red solid containing the metal complex M1a (11.48 g), silver trifluoromethanesulfonate (2.23 g), dichloromethane (36 mL) and acetonitrile (3.6 mL) were added, and the mixture was stirred for 3.5 hours. The resultant reaction liquid was purified by alumina column chromatography (acetonitrile), and the solvent was removed under reduced pressure, to obtain a red solid (hereinafter, referred to as "red solid M1b") (10.54 g). This operation was repeated, to obtain a necessary amount of the red solid M1b.

A nitrogen gas atmosphere was prepared in a light-shielded reaction vessel, then, the red solid M1b (12.9 g), the compound L1 (9.85 g), 2,6-lutidine (7.75 g) and diethylene glycol dimethyl ether (109 mL) were added, and the mixture was stirred at 155° C. for 43 hours. The resultant reaction liquid was cooled down to room temperature, then, added to ethanol (326 mL), and the mixture was stirred at 0° C. for 1.5 hours. The resultant mixture was filtrated, and the resultant solid was dissolved in dichloromethane, then, the solution was filtrated. The resultant filtrate was concentrated under reduced pressure, purified by silica gel column chromatography (a mixed solvent of hexane and dichloromethane), and the solvent was removed under reduced pressure, to obtain a solid. The resultant solid was dissolved in toluene, then, activated white earth was added, and the mixture was stirred for 30 minutes at 65° C. The resultant mixture was filtrated through a filter paved with Celite, and the resultant filtrate was concentrated under reduced pressure, to obtain a solid. The resultant solid was washed with ethyl acetate, then, filtrated, and the resultant solid was dried under reduced pressure overnight at 50° C., to obtain a metal complex M1 (5.3 g) as a red solid. The resultant metal complex M1 showed an HPLC area percentage value of 99.4%.

LC-MS (ESI positive): m/z=2270 [M+K]$^+$ $^1$H-NMR (CD$_2$Cl$_2$, 300 MHz): δ (ppm)=9.68 (d, 3H), 9.20 (dd, 3H), 8.43 (d, 12H), 8.29 (d, 3H), 7.95 (s, 3H), 7.41-7.39 (m, 15H), 7.28 (d, 3H), 7.22 (d, 3H), 7.06 (t, 3H), 6.77 (t, 3H), 2.32-2.11 (m, 15H), 2.05-1.91 (m, 9H), 1.84-1.57 (m, 9H), 1.48-1.38 (m, 3H), 1.20 (s, 54H).

<Synthesis Example 2> Synthesis of Compound L2

[Chemical Formula 114]

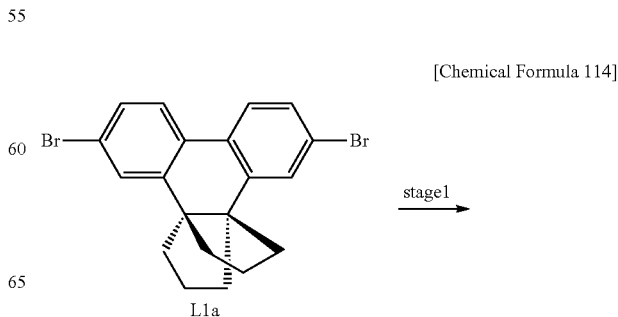

L1a stage1

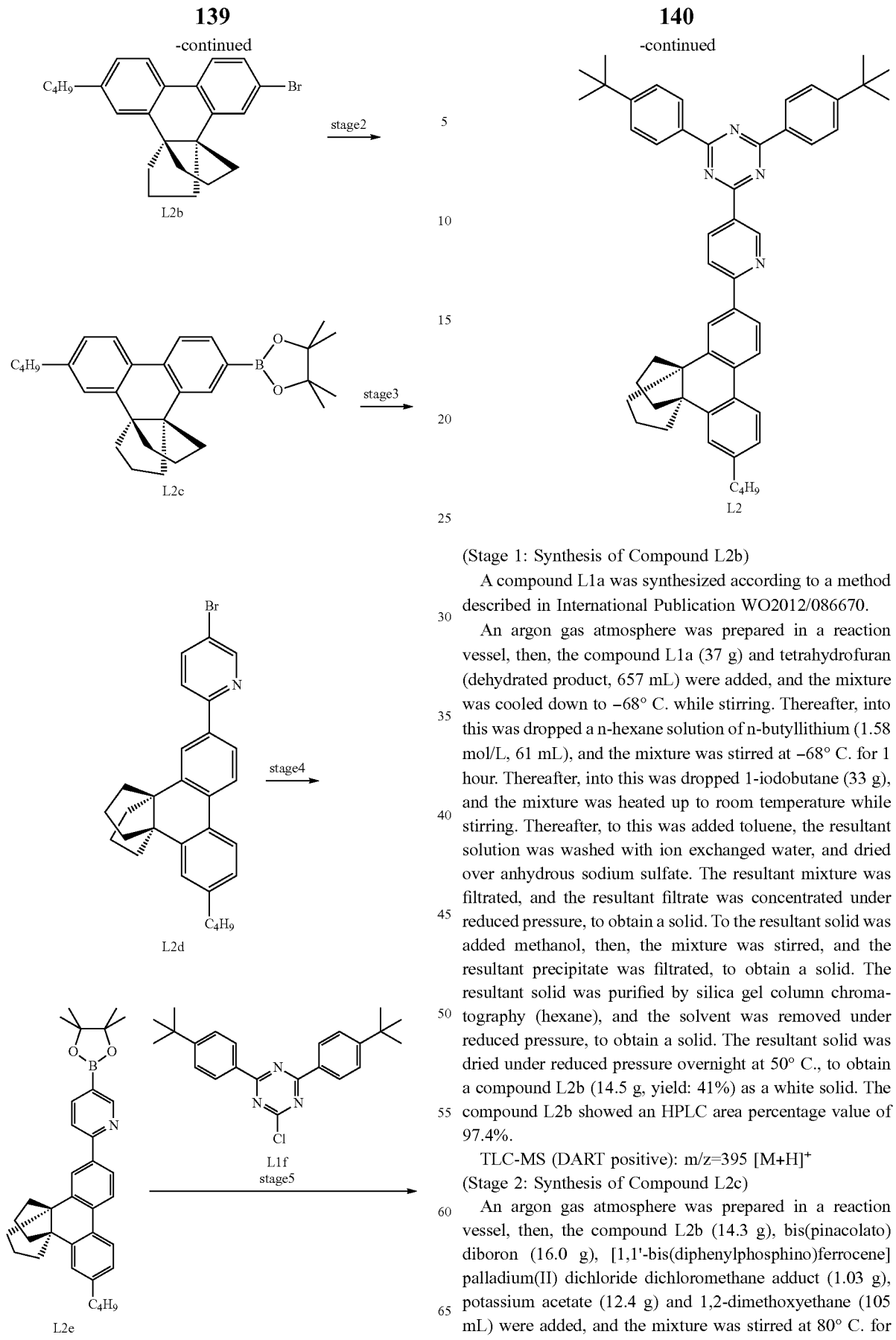

(Stage 1: Synthesis of Compound L2b)

A compound L1a was synthesized according to a method described in International Publication WO2012/086670.

An argon gas atmosphere was prepared in a reaction vessel, then, the compound L1a (37 g) and tetrahydrofuran (dehydrated product, 657 mL) were added, and the mixture was cooled down to −68° C. while stirring. Thereafter, into this was dropped a n-hexane solution of n-butyllithium (1.58 mol/L, 61 mL), and the mixture was stirred at −68° C. for 1 hour. Thereafter, into this was dropped 1-iodobutane (33 g), and the mixture was heated up to room temperature while stirring. Thereafter, to this was added toluene, the resultant solution was washed with ion exchanged water, and dried over anhydrous sodium sulfate. The resultant mixture was filtrated, and the resultant filtrate was concentrated under reduced pressure, to obtain a solid. To the resultant solid was added methanol, then, the mixture was stirred, and the resultant precipitate was filtrated, to obtain a solid. The resultant solid was purified by silica gel column chromatography (hexane), and the solvent was removed under reduced pressure, to obtain a solid. The resultant solid was dried under reduced pressure overnight at 50° C., to obtain a compound L2b (14.5 g, yield: 41%) as a white solid. The compound L2b showed an HPLC area percentage value of 97.4%.

TLC-MS (DART positive): m/z=395 [M+H]$^+$ (Stage 2: Synthesis of Compound L2c)

An argon gas atmosphere was prepared in a reaction vessel, then, the compound L2b (14.3 g), bis(pinacolato)diboron (16.0 g), [1,1′-bis(diphenylphosphino)ferrocene]palladium(II) dichloride dichloromethane adduct (1.03 g), potassium acetate (12.4 g) and 1,2-dimethoxyethane (105 mL) were added, and the mixture was stirred at 80° C. for 15 hours. The resultant reaction liquid was cooled down to room temperature, then, toluene (160 mL) was added, and the mixture was filtrated through a filter paved with Celite, and the resultant filtrate was concentrated under reduced pressure. Thereafter, to this were added hexane (105 mL) and activated carbon, and the mixture was stirred at 65° C. for 1 hour. The resultant mixture was filtrated through a filter paved with Celite, and the resultant filtrate was concentrated under reduced pressure, to obtain a solid. The resultant solid was crystallized using a mixed solvent of toluene and acetonitrile, to obtain a compound L2c (12.5 g, yield: 78%) as a white solid. The resultant compound L2c showed an HPLC area percentage value of 97.1%.

TLC-MS (DART positive): m/z=442 [M]$^+$ $^1$H-NMR (CD$_2$Cl$_2$, 600 MHz): δ (ppm)=7.85 (d, 1H), 7.81 (d, 1H), 7.74 (d, 1H), 7.56 (dd, 1H), 7.18 (d, 1H), 7.04 (dd, 1H), 2.60 (t, 2H), 2.20-2.13 (m, 4H), 1.98-1.92 (m, 4H), 1.67-1.58 (m, 4H), 1.44-1.34 (m, 4H), 1.33 (s, 12H), 0.94 (t, 3H).

(Stage 3: Synthesis of Compound L2d)

An argon gas atmosphere was prepared in a reaction vessel, then, the compound L2c (12.4 g), 2,5-dibromopyridine (8.0 g), tetrakis(triphenylphosphine)palladium(0) (650 mg), toluene (167 mL), tetrahydrofuran (84 mL), tert-butanol (112 mL), ion exchanged water (56 mL) and a 40 wt % tetrabutylammonium hydroxide aqueous solution (73 g) were added, and the mixture was stirred at 50° C. for 19 hours. The resultant reaction liquid was cooled down to room temperature, then, toluene was added, and the resultant organic layer was washed with ion exchanged water, and dried over anhydrous magnesium sulfate. The resultant mixture was filtrated, and the resultant filtrate was concentrated under reduced pressure, to obtain a solid. The resultant solid was dissolved in toluene, the solution was filtrated through a filter paved with silica gel, and the resultant filtrate was concentrated under reduced pressure, to obtain a solid. The resultant solid was washed with methanol, then, filtrated, to obtain a compound L2d (11.4 g, yield: 86%) as a white solid. The resultant compound L2d showed an HPLC area percentage value of 96.2%.

TLC-MS (DART positive): m/z=472 [M+H]$^+$ $^1$H-NMR (CD$_2$Cl$_2$, 600 MHz): δ (ppm)=8.71 (d, 1H), 8.02 (d, 1H), 7.95 (d, 1H), 7.87 (dd, 1H), 7.83 (d, 1H), 7.79 (dd, 1H), 7.68 (d, 1H), 7.21 (d, 1H), 7.06 (dd, 1H), 2.62 (t, 2H), 2.25-2.16 (m, 4H), 2.04-1.95 (m, 4H), 1.70-1.59 (m, 4H), 1.47-1.35 (m, 4H), 0.94 (t, 3H).

(Stage 4: Synthesis of Compound L2e)

An argon gas atmosphere was prepared in a reaction vessel, then, the compound L2d (11.3 g), bis(pinacolato)diboron (9.1 g), [1,1'-bis(diphenylphosphino)ferrocene]palladium(II) dichloride dichloromethane adduct (560 mg), potassium acetate (7.1 g) and 1,2-dimethoxyethane (60 mL) were added, and the mixture was stirred at 80° C. for 3.5 hours. The resultant reaction liquid was cooled down to room temperature, then, toluene (90 mL) was added, and the mixture was filtrated through a filter paved with Celite, and the resultant filtrate was concentrated under reduced pressure. Thereafter, to this were added hexane and activated carbon, and the mixture was stirred at 70° C. for 2 hours. The resultant mixture was filtrated through a filter paved with Celite, and the resultant filtrate was concentrated under reduced pressure, to obtain a compound L2e (11.1 g, yield: 89%) as a colorless oil. The resultant compound L2e showed an HPLC area percentage value of 99.5% or more.

TLC-MS (DART positive): m/z=520 [M+H]$^+$ $^1$H-NMR (CD$_2$Cl$_2$, 600 MHz): δ (ppm)=8.93 (d, 1H), 8.08-8.07 (m, 2H), 7.96 (d, 1H), 7.87 (dd, 1H), 7.84 (d, 1H), 7.77 (dd, 1H), 7.21 (d, 1H), 7.06 (dd, 1H), 2.62 (t, 2H), 2.27-2.23 (m, 2H), 2.20-2.16 (m, 2H), 2.06-1.96 (m, 4H), 1.70-1.59 (m, 4H), 1.48-1.35 (m, 16H), 0.94 (t, 3H).

(Stage 5: Synthesis of Compound L2)

A compound L1f was synthesized according to a method described in JP-A No. 2008-179617.

An argon gas atmosphere was prepared in a light-shielded reaction vessel, then, the compound L2e (8.3 g), the compound L1f (7.29 g), tetrakis(triphenylphosphine)palladium(0) (370 mg), toluene (88 mL) and a 20 wt % tetraethylammonium hydroxide aqueous solution (47 g) were added, and the mixture was stirred at 70° C. for 4 hours. The resultant reaction liquid was cooled down to room temperature, then, toluene was added, the resultant solution was washed with ion exchanged water, then, dried over anhydrous sodium sulfate. The resultant mixture was filtrated, and the resultant filtrate was concentrated under reduced pressure, to obtain a solid. The resultant solid was purified by silica gel column chromatography (a mixed solvent of hexane and toluene), and the solvent was removed under reduced pressure, to obtain a solid. The resultant solid was dried under reduced pressure overnight at 50° C., to obtain a compound L2 (8.2 g, yield: 70%) as a pale yellow-green solid. The compound L2 showed an HPLC area percentage value of 99.5%.

TLC-MS (DART positive): m/z=737 [M+H]$^+$ $^1$H-NMR (CD$_2$Cl$_2$, 300 MHz): δ (ppm)=10.00 (dd, 1H), 9.07 (dd, 1H), 8.71 (dt, 4H), 8.25 (s, 1H), 8.06-7.99 (m, 3H), 7.89 (m, 1H), 7.64 (dt, 4H), 7.24 (dd, 1H), 7.10 (dd, 1H), 2.65 (t, 2H), 2.36-2.28 (m, 2H), 2.26-2.18 (m, 2H), 2.15-1.97 (m, 4H), 1.79-1.60 (m, 4H), 1.56-1.37 (m, 22H), 0.97 (t, 3H).

<Example 2> Synthesis of Metal Complex M2
[Chemical Formula 115]
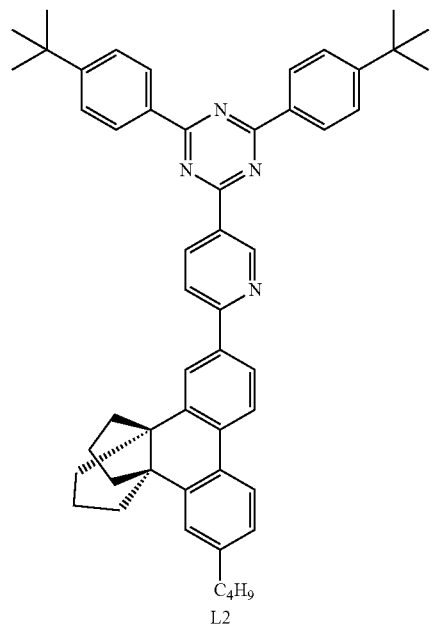
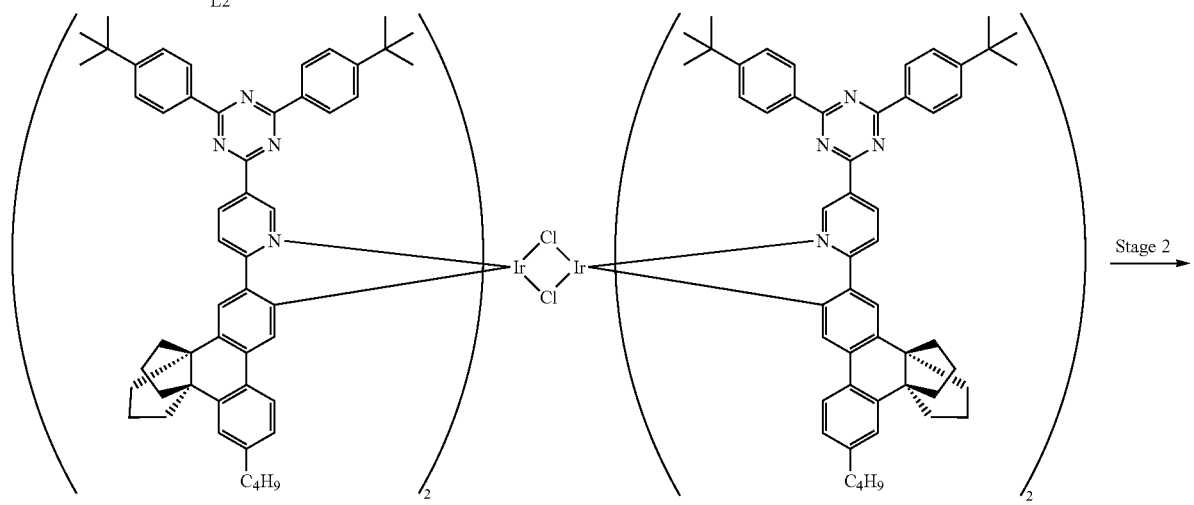
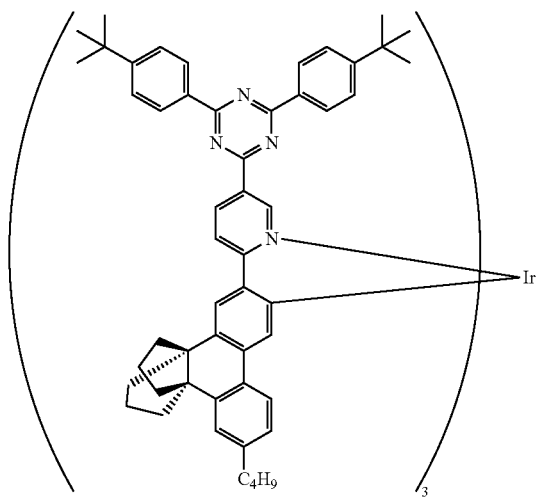

(Stage 1: Synthesis of Metal Complex M2a)

A nitrogen gas atmosphere was prepared in a light-shielded reaction vessel, then, the compound L2 (5.2 g) and 2-ethoxyethanol (473 mL) were added, and the mixture was heated up to 80° C. Thereafter, into this was dropped iridium(III) chloride n-hydrate (1.11 g) dissolved in ion exchanged water (158 mL), then, the mixture was stirred at 105° C. for 8 hours. The resultant reaction liquid was heated, and the solvent was distilled off until the amount of the reaction liquid was about 300 mL. Thereafter, to this was added 2-ethoxyethanol (150 mL), and the mixture was stirred at 133° C. for 64 hours. The resultant reaction liquid was cooled down to room temperature, then, added to ethanol (630 mL), and the mixture was stirred for 15 minutes. The resultant mixture was filtrated, the resultant residue was dissolved in dichloromethane, then, the solution was washed with ion exchanged water, and dried over anhydrous sodium sulfate. The resultant mixture was filtrated, and the resultant filtrate was concentrated under reduced pressure, to obtain a solid. The resultant solid was dried under reduced pressure overnight at 50° C., to obtain a red solid (4.4 g) containing a metal complex M2a.

(Stage 2: Synthesis of Metal Complex M2)

An argon gas atmosphere was prepared in a light-shielded reaction vessel, then, the red solid (4.1 g) containing the metal complex M2a, silver trifluoromethanesulfonate (740 mg), dichloromethane (12 mL) and acetonitrile (1.2 mL) were added, and the mixture was stirred for 4 hours. The resultant reaction liquid was purified by alumina column chromatography (acetonitrile), and the solvent was removed under reduced pressure, to obtain a red solid (hereinafter, referred to as "red solid M2b") (3.9 g).

An argon gas atmosphere was prepared in a light-shielded reaction vessel, then, the red solid M2b (1.3 g), the compound L2 (1.0 g), 2,6-lutidine (750 mg) and diethylene glycol dimethyl ether (21 mL) were added, and the mixture was stirred at 155° C. for 43 hours. The resultant reaction liquid was cooled down to room temperature, then, added to the ethanol (60 mL), and the mixture was stirred at 0° C. for 1.5 hours. The resultant mixture was filtrated, the resultant solid was dissolved in toluene, then, the solution was filtrated. The resultant filtrate was concentrated under reduced pressure, purified by silica gel column chromatography (a mixed solvent of toluene and hexane), and dried under reduced pressure overnight at 50° C., to obtain a metal complex M2 (630 mg) as a red solid. The resultant metal complex M2 showed an HPLC area percentage value of 98.2%.

LC-MS (APCI positive): m/z=2400 [M+H]$^+$ $^1$H-NMR (CD$_2$Cl$_2$, 300 MHz): δ (ppm)=9.67 (d, 3H), 9.18 (dd, 3H), 8.42 (d, 12H), 8.26 (d, 3H), 7.92 (s, 3H), 7.40 (d, 12H), 7.36 (s, 3H), 7.13 (d, 3H), 7.08 (d, 3H), 6.60 (dd, 3H), 2.48 (t, 6H), 2.34-1.14 (m, 102H), 0.87 (t, 9H).

<Comparative Example 1> Synthesis of Metal Complex CM1

A metal complex CM1 was synthesized according to a method described in JP-A No. 2011-105701.

[Chemical Formula 116]

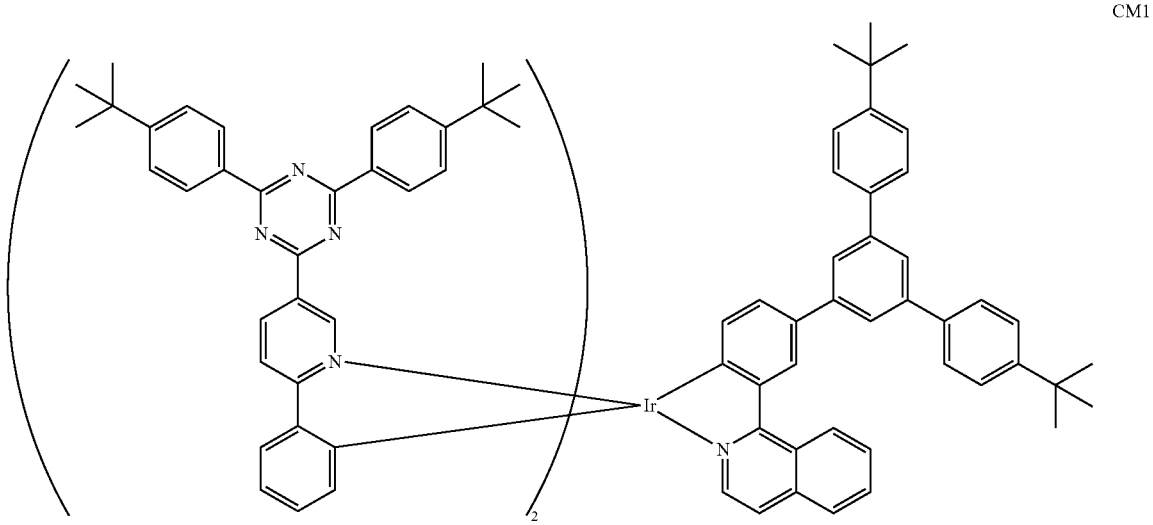

CM1

<Measurement Example 1> Measurement of PLQY and Light Emission Spectrum of Metal Complex M1

PLQY and emission spectrum were measured, using a xylene solution of the metal complex M1 (0.0008% by weight). Light emission showing the maximum peak of an emission spectrum at 628 nm was observed, and FWHM of this emission spectrum was 45 nm, and PLQY was 67%. The light emission spectrum of the metal complex M1 is shown in FIG. 1.

<Measurement Example 2> Measurement of PLQY and Light Emission Spectrum of Metal Complex M2

PLQY and emission spectrum were measured, using a xylene solution of the metal complex M2 (0.0008% by weight). Light emission showing the maximum peak of an emission spectrum at 633 nm was observed, and FNHM of this emission spectrum was 44 nm, and PLQY was 68%. The light emission spectrum of the metal complex M2 is shown in FIG. 1.

<Measurement Example C1> Measurement of PLOY and Light Emission Spectrum of Metal Complex CM1

PLQY and emission spectrum were measured, using a xylene solution of the metal complex CM1 (0.0008% by weight). Light emission showing the maximum peak of an emission spectrum at 615 nm was observed, and FWHM of this emission spectrum was 88 nm, and PLOY was 53%. The light emission spectrum of the metal complex CM1 is shown in FIG. 1.

These results show that the metal complex M1 and the metal complex M2 of the present invention are excellent in the quantum yield and FWHM of the light emission spectrum, as compared with the metal complex CM1.

<Synthesis Example 3> Synthesis of Compound L3

[Chemical Formula 117]

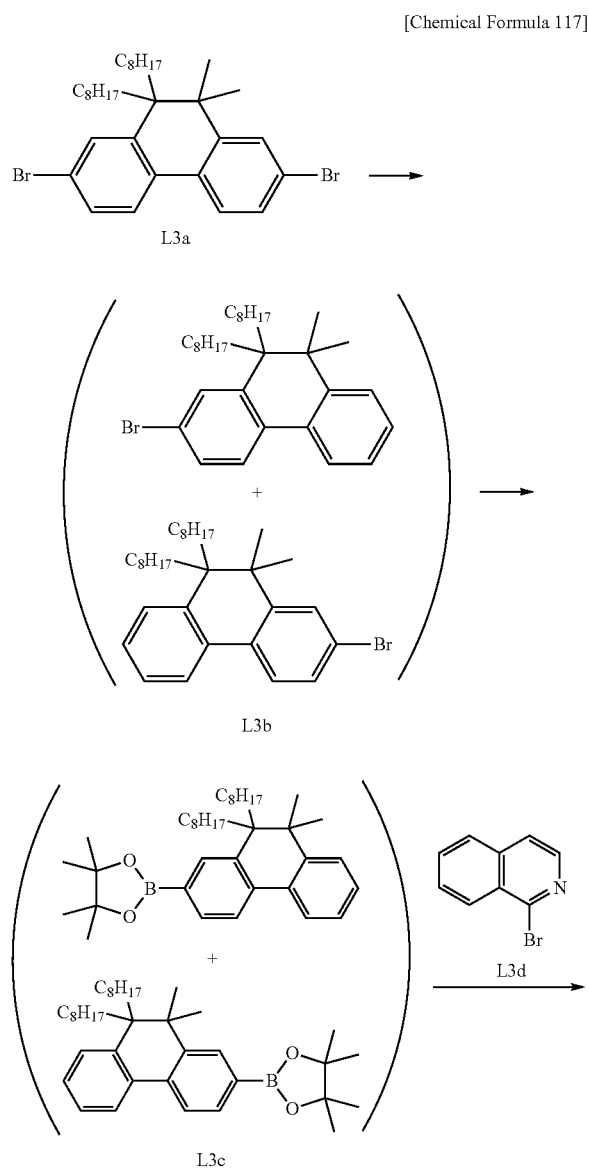

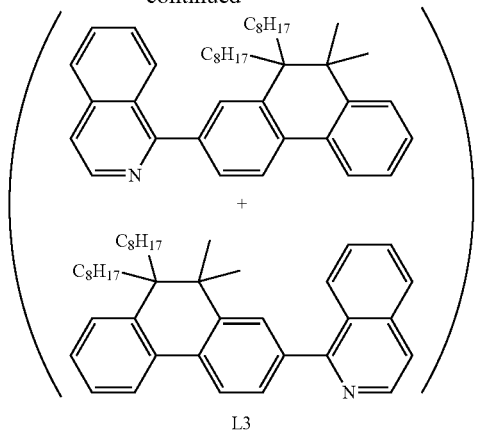

(Synthesis of compound L3b)

A compound L3a was synthesized according to a method described in International Publication WO2012/086671.

A nitrogen gas atmosphere was prepared in a reaction vessel, then, the compound L3a (2.00 g) and tetrahydrofuran (22.5 mL) were added, and the mixture was cooled down to −68° C. while stirring. Thereafter, into this was dropped a n-hexane solution of n-butyllithium (2.65 mol/L, 1.3 mL), and the mixture was stirred at −68° C. for 3 hours. Thereafter, into this was dropped ion exchanged water (0.3 g), and the mixture was heated up to room temperature overnight while stirring. Thereafter, to this was added heptane, the resultant mixture was washed with ion exchanged water, and dried over anhydrous sodium sulfate. The resultant mixture was filtrated through a filter paved with silica gel, and the resultant filtrate was concentrated under reduced pressure, and dried under reduced pressure at 50° C., to obtain a compound L3b in the form of an isomer mixture as a colorless liquid (1.66 g). The resultant compound L3b showed an HPLC area percentage value of 88.6%.

TLC-MS (DART positive): m/z=510 [M]$^+$ $^1$H-NMR (CDCl$_3$, 300 MHz): δ (ppm)=7.65 (t, 1H), 7.56 (d, 1H), 7.45-7.37 (m, 2H), 7.33-7.27 (m, 3H), 2.07-1.81 (m, 2H), 1.73-0.76 (m, 38H).

(Synthesis of Compound L3c)

A nitrogen gas atmosphere was prepared in a reaction vessel, then, the compound L3b (0.84 g), bis(pinacolato) diboron (0.48 g), [1,1'-bis(diphenylphosphino)ferrocene] palladium(II) dichloride dichloromethane adduct (0.01 g), potassium acetate (0.50 g) and 1,4-dioxane (8.3 g) were added, and the mixture was stirred under reflux for 7.5 hours. The resultant reaction liquid was cooled down to room temperature, then, toluene was added, and the mixture was washed with ion exchanged water, and dried over anhydrous sodium sulfate. The resultant mixture was filtrated, and the resultant filtrate was concentrated under reduced pressure, to obtain a crude product L3c-1.

A nitrogen gas atmosphere was prepared in a reaction vessel, then, the compound L3b (0.80 g), bis(pinacolato)diboron (0.45 g), [1,1'-bis(diphenylphosphino)ferrocene]palladium(II) dichloride dichloromethane adduct (0.01 g), potassium acetate (0.54 g) and 1,4-dioxane (8.1 g) were added, and the mixture was stirred under reflux for 7 hours. The resultant reaction liquid was cooled down to room temperature, then, toluene was added, and the mixture was washed with ion exchanged water, and dried over anhydrous sodium sulfate. The resultant mixture was filtrated, and the resultant filtrate was concentrated under reduced pressure, to obtain a crude product L3c-2.

The crude products L3c-1 and L3c-2 obtained above, and heptane and activated carbon were mixed, and the mixture was stirred for 30 minutes at room temperature. The resultant mixture was filtrated, and the resultant filtrate was concentrated under reduced pressure, to obtain a compound L3c (1.87 g) in the form of an isomer mixture as a colorless oil. The compound L3c showed an HPLC area percentage value of 82.9%.

TLC-MS (DART positive): m/z=559 [M+H]$^+$ $^1$H-NMR (CDCl$_3$, 300 MHz): δ (ppm)=7.82-7.65 (m, 4H), 7.34-7.22 (m, 3H), 2.05-1.84 (m, 2H), 1.76-0.76 (m, 50H).

(Synthesis of Compound L3)

A compound L3d was purchased from Tokyo Chemical Industry Co., Ltd.

A nitrogen gas atmosphere was prepared in a light-shielded reaction vessel, then, the compound L3c (1.10 g), the compound L3d (0.61 g), tetrakis(triphenylphosphine)palladium(0) (0.02 g), toluene (19.4 g) and a 20 wt % tetraethylammonium hydroxide aqueous solution (5.8 g) were added, and the mixture was stirred at 80° C. for 7.5 hours. The resultant reaction liquid was cooled down to room temperature, to obtain a reaction liquid L3-1.

A nitrogen gas atmosphere was prepared in a light-shielded reaction vessel, then, the compound L3c (0.60 g), the compound L3d (0.35 g), tetrakis(triphenylphosphine)palladium(0) (0.01 g), toluene (10.7 g) and a 20 wt % tetraethylammonium hydroxide aqueous solution (3.2 g) were added, and the mixture was stirred at 80° C. for 9.5 hours. The resultant reaction liquid was cooled down to room temperature, to obtain a reaction liquid L3-2.

The reaction liquid L3-1 and the reaction liquid L3-2 obtained above were mixed, the mixture was washed with ion exchanged water, then, dried over anhydrous sodium sulfate. The resultant mixture was filtrated, and the resultant filtrate was concentrated under reduced pressure, to obtain a liquid. The resultant liquid was purified by silica gel column chromatography (a mixed solvent of hexane and chloroform), and the solvent was removed under reduced pressure, to obtain a liquid. The resultant liquid was purified by a recycling preparative system LC908 manufactured by Japan Analytical Industry Co., Ltd. (GPC column JAIGEL-2.5H), the solvent was removed under reduced pressure, and the resultant liquid was dried at 50° C. under reduced pressure, to obtain a compound L3 (0.84 g) in the form of an isomer mixture as a colorless oil. The compound L3 showed an HPLC area percentage value of 99.5% or more.

TLC-MS (DART positive): m/z=560 [M+H]$^+$ $^1$H-NMR (CD$_2$Cl$_2$, 300 MHz): δ (ppm)=8.62 (d, 1H), 8.21 (dd, 1H), 7.93 (t, 2H), 7.87-7.80 (m, 1H), 7.78-7.53 (m, 5H), 7.44-7.29 (m, 3H), 2.13-1.90 (m, 2H), 1.84-0.47 (m, 38H).

<Example 3> Synthesis of Metal Complex M3

[Chemical Formula 118]

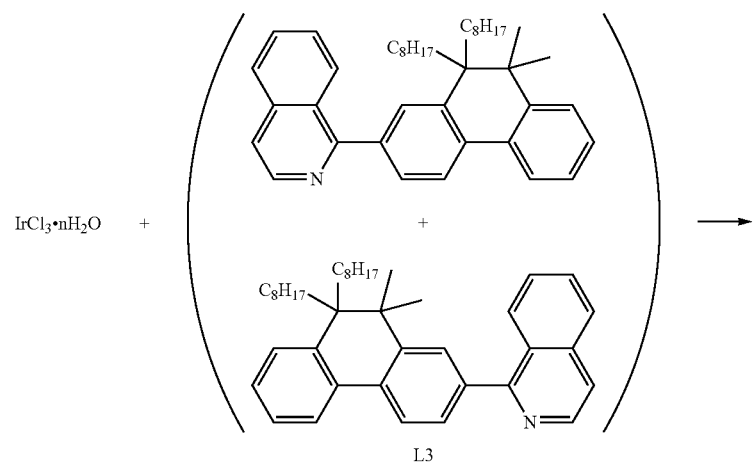

A nitrogen gas atmosphere was prepared in a light-shielded reaction vessel, then, the compound L3 (0.43 g) and 2-ethoxyethanol (24.0 g) were added, and the mixture was heated up to 85° C. Thereafter, into this was dropped iridium(III) chloride n-hydrate (0.12 g) dissolved in ion exchanged water (5.0 g), then, the mixture was stirred at 105° C. for 16 hours. The resultant reaction liquid was heated, the solvent was partially distilled off, then, the liquid was stirred at 130° C. for 26.5 hours. The resultant reaction liquid was cooled down to room temperature, then, toluene was added, and the mixture was washed with ion exchanged water, then, dried over anhydrous sodium sulfate. The resultant mixture was filtrated, and the resultant filtrate was concentrated under reduced pressure, to obtain a solid. To the resultant solid was added methanol and the mixture was stirred, the resultant mixture was filtrated, and the resultant solid was dried at 50° C. under reduced pressure, to obtain a red solid (0.42 g).

A nitrogen gas atmosphere was prepared in a light-shielded reaction vessel, then, the red solid (0.30 g) obtained above, silver trifluoromethanesulfonate (0.08 g), the compound L3 (0.14 g), 2,6-lutidine (0.04 g) and diethylene glycol dimethyl ether (3.0 g) were added, and the mixture was stirred at 150° C. for 4 hours. The resultant reaction liquid was cooled down to room temperature, then, methanol was added, and the mixture was stirred at room temperature, and the resultant mixture was filtrated. The resultant solid was dissolved in toluene, then, the resultant mixture was filtrated, and the resultant filtrate was concentrated under reduced pressure. The resultant solid was purified by silica gel column chromatography (a mixed solvent of toluene and hexane), and the solvent was removed under reduced pressure, to obtain a solid. To the resultant solid was added methanol and the mixture was stirred, the resultant mixture was filtrated, and the resultant solid was dried at 50° C. under reduced pressure, to obtain a metal complex M3 (0.18 g) in the form of an isomer mixture as a red solid. The sum of the HPLC area percentage values of four kinds of peaks the target material-equivalent m/z of which had been confirmed by LC-MS was 96.7%.

LC-MS (APCI positive): m/z=1869 [M+H]$^+$

1H-NMR (CD$_2$Cl$_2$, 600 MHz): δ (ppm)=9.11-8.88 (m, 3H), 8.39-7.98 (m, 4H), 7.86-6.65 (m, 27H), 6.63-6.19 (m, 2H), 2.24-0.05 (m, 120H).

<Measurement Example 3> Measurement of PLQY and Light Emission Spectrum of Metal Complex M3

PLQY and emission spectrum were measured, using a xylene solution of the metal complex M3 (0.0008% by weight). Light emission showing the maximum peak of an emission spectrum at 650 nm was observed, and FWHM of this emission spectrum was 52 nm, and PLOY was 43%. The light emission spectrum of the metal complex M3 is shown in FIG. 2.

<Synthesis Example 4> Synthesis of Compound L4

-continued

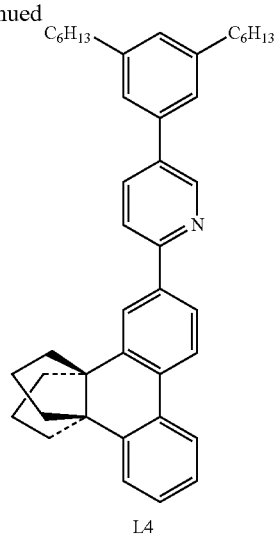

L4

A compound L4a was synthesized according to a method described in JP-A No. 2011-174062.

A nitrogen gas atmosphere was prepared in a light-shielded reaction vessel, then, the compound L1e (3.70 g), the compound L4a (2.60 g), tetrakis(triphenylphosphine)palladium(0) (0.09 g), toluene (46.9 g) and a 20 wt % tetraethylammonium hydroxide aqueous solution (23.6 g) were added, and the mixture was stirred at 70° C. for 6 hours. The resultant reaction liquid was cooled down to room temperature, to obtain a reaction liquid L4-1.

A nitrogen gas atmosphere was prepared in a light-shielded reaction vessel, then, the compound L1e (0.92 g), the compound L4a (0.66 g), tetrakis(triphenylphosphine)palladium(0) (0.02 g), toluene (11.8 g) and a 20 wt % tetraethylammonium hydroxide aqueous solution (5.9 g) were added, and the mixture was stirred at 70° C. for 5 hours. The resultant reaction liquid was cooled down to room temperature, to obtain a reaction liquid L4-2.

The reaction liquid L4-1 and the reaction liquid L4-2 obtained above were mixed, and the mixture was washed with ion exchanged water, then, dried over anhydrous sodium sulfate. The resultant mixture was filtrated, and the resultant filtrate was concentrated under reduced pressure, to obtain a liquid. The resultant liquid was purified by silica gel column chromatography (a mixed solvent of hexane and toluene), and the solvent was removed under reduced pressure, to obtain a liquid. The resultant liquid was dried at 50° C. under reduced pressure, to obtain a compound L4 (4.56 g) as a colorless oil. The compound L4 showed an HPLC area percentage value of 99.5%.

TLC-HS (DART positive): m/z=582 [M+H]$^+$ $^1$H-NMR (CD$_2$Cl$_2$, 300 MHz): δ (ppm)=8.94 (d, 1H), 8.15 (d, 1H), 8.08-7.85 (m, 5H), 7.44 (dd, 1H), 7.36-7.22 (m, 4H), 7.08 (s, 1H), 2.75-2.64 (m, 4H), 2.35-2.17 (m, 4H), 2.16-1.96 (m, 4H), 1.80-1.61 (m, 6H), 1.59-1.26 (m, 14H), 0.97-0.85 (m, 6H).

<Example 4> Synthesis of Metal Complex M4

[Chemical Formula 120]

IrCl$_3$ nH$_2$O + 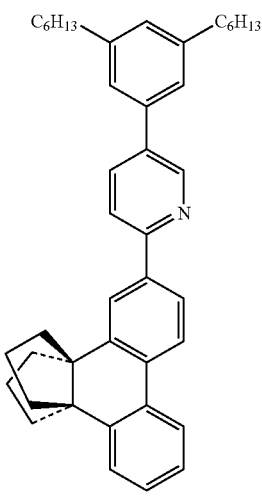 

L4

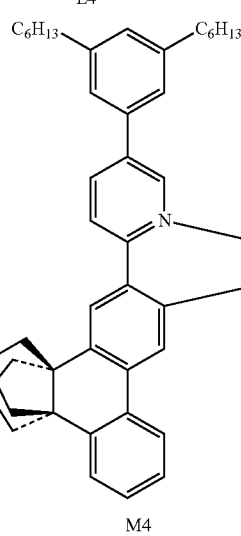

M4

A nitrogen gas atmosphere was prepared in a light-shielded reaction vessel, then, the compound L4 (0.97 g) and 2-ethoxyethanol (49.1 g) were added, and the mixture was heated up to 85° C. Thereafter, into this was dropped iridium(III) chloride n-hydrate (0.25 g) dissolved in ion exchanged water (17.3 g), then, the mixture was stirred at 105° C. for 16.5 hours. The resultant reaction liquid was heated, the solvent was partially distilled off, then, the mixture was stirred at 130° C. for 24.5 hours. The resultant reaction liquid was cooled down to room temperature, then, methanol was added and the mixture was stirred. The resultant mixture was filtrated, the resultant solid was washed with methanol, and the resultant solid was dried at 50° C. under reduced pressure, to obtain an orange solid (0.84 g).

A nitrogen gas atmosphere was prepared in a light-shielded reaction vessel, then, the orange solid (0.25 g) obtained above, silver trifluoromethanesulfonate (0.06 g), the compound L4 (0.12 g), 2,6-lutidine (0.02 g) and diethylene glycol dimethyl ether (2.5 g) were added, and the mixture was stirred at 150° C. for 6 hours. The resultant reaction liquid was cooled down to room temperature, then, methanol was added, the mixture was cooled to 0° C. and stirred, and the resultant mixture was filtrated. The resultant solid was dissolved in toluene, then, the resultant mixture was filtrated through a filter paved with silica gel. The resultant filtrate was concentrated under reduced pressure, the resultant solid was crystallized using a mixed solvent of toluene and heptane, and the crystal was dried under reduced pressure at 50° C., to obtain a metal complex M4 (0.19 g) as an orange solid. The resultant metal complex M4 showed an HPLC area percentage value of 98.5%.

LC-MS (APCI positive): m/z=1935 [M+H]$^+$ $^1$H-NMR (CD$_2$Cl$_2$, 300 MHz): δ (ppm)=8.21 (d, 3H), 8.04 (d, 3H), 7.95 (dd, 3H), 7.79 (s, 3H), 7.45 (s, 3H), 7.31-7.18 (m, 6H), 7.09-7.00 (m, 9H), 6.92 (s, 3H), 6.74 (t, 3H), 2.51-2.39 (m, 12H), 2.32-2.10 (m, 15H), 2.08-1.91 (m, 9H), 1.84-1.55 (m, 9H), 1.50-1.35 (m, 15H), 1.32-1.12 (m, 36H), 0.92-0.83 (m, 18H).

<Example 5> Synthesis of Metal Complex M5

[Chemical Formula 121]

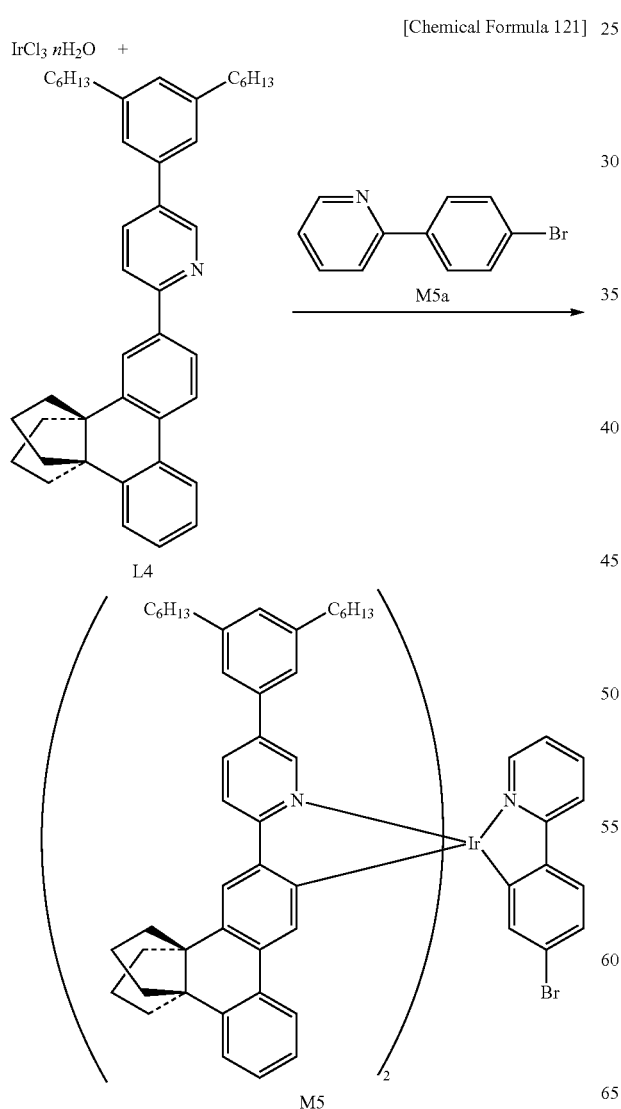

A compound M5a was purchased from Synco Chemie.

A nitrogen gas atmosphere was prepared in a light-shielded reaction vessel, then, the compound L4 (0.97 g) and 2-ethoxyethanol (49.1 g) were added, and the mixture was heated up to 85° C. Thereafter, into this was dropped iridium(III) chloride n-hydrate (0.25 g) dissolved in ion exchanged water (17.3 g), then, the mixture was stirred at 105° C. for 16 hours and 30 minutes. The resultant reaction liquid was heated, the solvent was partially distilled off, then, the mixture was stirred at 130° C. for 24.5 hours. The resultant reaction liquid was cooled down to room temperature, then, methanol was added and the mixture was stirred. The resultant mixture was filtrated, the resultant solid was washed with methanol, and the resultant solid was dried at 50° C. under reduced pressure, to obtain an orange solid (0.84 g).

A nitrogen gas atmosphere was prepared in a light-shielded reaction vessel, then, the orange solid (0.20 g) obtained above, silver trifluoromethanesulfonate (0.04 g), the compound M5a (0.03 g) and diethylene glycol dimethyl ether (2.0 g) were added, and the mixture was stirred at 65° C. for 17.5 hours. The resultant reaction liquid was cooled down to room temperature, then, methanol was added, the mixture was cooled to 0° C. and stirred, and the resultant mixture was filtrated. The resultant solid was dissolved in toluene, then, the resultant mixture was filtrated through a filter paved with silica gel. The resultant filtrate was concentrated under reduced pressure, the resultant solid was purified by silica gel column chromatography (a mixed solvent of toluene and hexane), the solvent was removed under reduced pressure, and the solid was dried under reduced pressure at 50° C., to obtain a metal complex M5 (0.05 g) as an orange solid. The resultant metal complex M5 showed an HPLC area percentage value of 99.5%.

LC-MS (APCI positive): m/z=1587 [M+H]$^+$ $^1$H-NMR (CD$_2$Cl$_2$, 300 MHz): δ (ppm)=8.14-7.92 (m, 8H), 7.86 (s, 1H), 7.80-7.64 (m, 3H), 7.56 (s, 1H), 7.49-7.40 (m, 2H), 7.39-6.94 (m, 15H), 6.84 (t, 1H), 2.64-2.42 (m, 8H), 2.38-1.10 (m, 56H), 1.04-0.81 (m, 12H).

<Measurement Example 4> Measurement of PLQY and Light Emission Spectrum of Metal Complex M4

PLQY and emission spectrum were measured, using a xylene solution of the metal complex M4 (0.0008% by weight). Light emission showing the maximum peak of an emission spectrum at 575 nm was observed, and FWHM of this emission spectrum was 34 nm, and PLQY was 75%. The light emission spectrum of the metal complex M4 is shown in FIG. 3.

<Measurement Example 5> Measurement of PLQY and Light Emission Spectrum of Metal Complex M5

PLOY and emission spectrum were measured, using a xylene solution of the metal complex M5 (0.0008% by weight). Light emission showing the maximum peak of an emission spectrum at 571 nm was observed, and FWHM of this emission spectrum was 68 nm, and PLOY was 61%. The light emission spectrum of the metal complex M5 is shown in FIG. 3.

<Synthesis Example 5> Synthesis of Compound L6

[Chemical Formula 122]

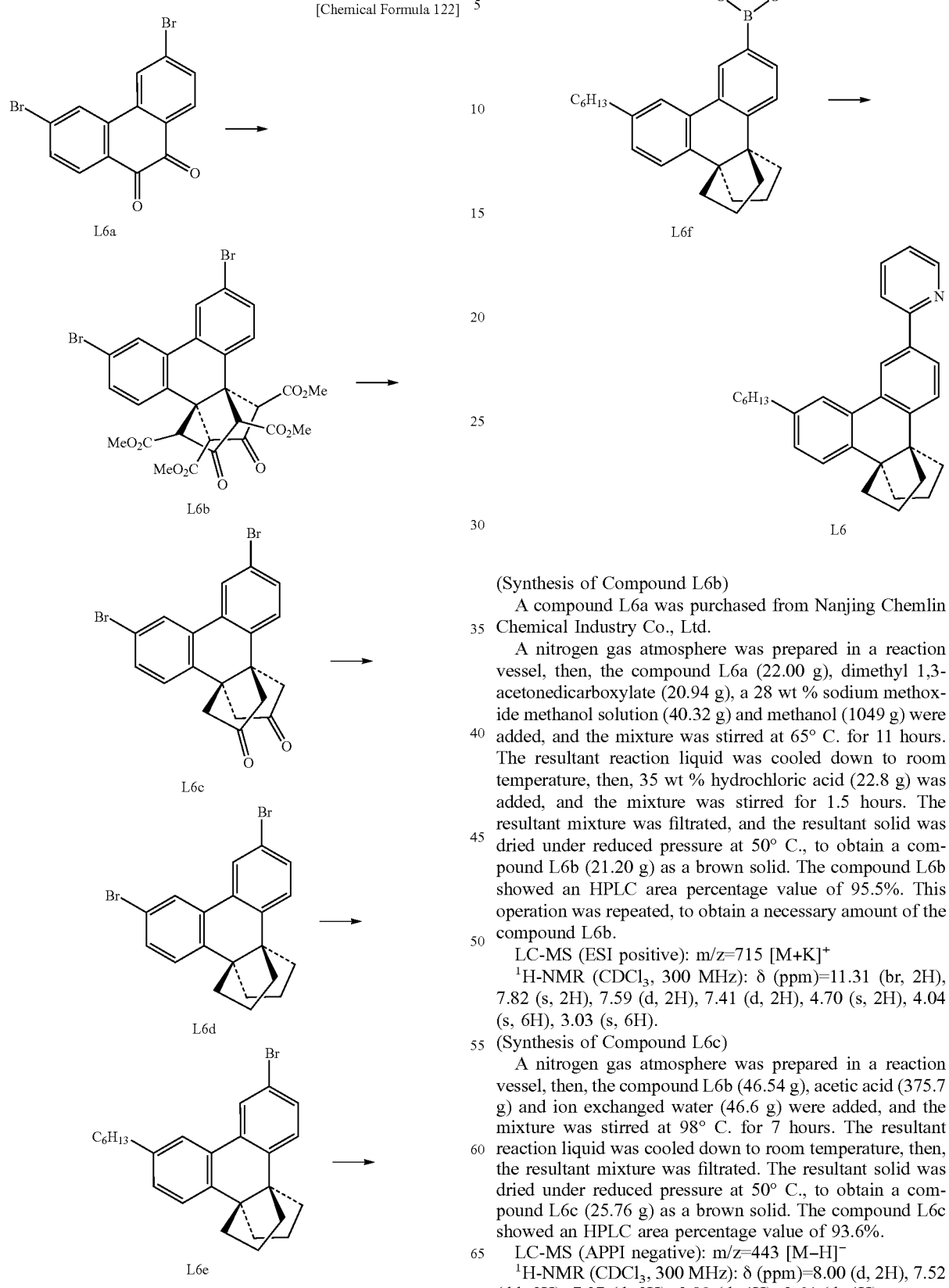

(Synthesis of Compound L6b)

A compound L6a was purchased from Nanjing Chemlin Chemical Industry Co., Ltd.

A nitrogen gas atmosphere was prepared in a reaction vessel, then, the compound L6a (22.00 g), dimethyl 1,3-acetonedicarboxylate (20.94 g), a 28 wt % sodium methoxide methanol solution (40.32 g) and methanol (1049 g) were added, and the mixture was stirred at 65° C. for 11 hours. The resultant reaction liquid was cooled down to room temperature, then, 35 wt % hydrochloric acid (22.8 g) was added, and the mixture was stirred for 1.5 hours. The resultant mixture was filtrated, and the resultant solid was dried under reduced pressure at 50° C., to obtain a compound L6b (21.20 g) as a brown solid. The compound L6b showed an HPLC area percentage value of 95.5%. This operation was repeated, to obtain a necessary amount of the compound L6b.

LC-MS (ESI positive): m/z=715 [M+K]$^+$ $^1$H-NMR (CDCl$_3$, 300 MHz): δ (ppm)=11.31 (br, 2H), 7.82 (s, 2H), 7.59 (d, 2H), 7.41 (d, 2H), 4.70 (s, 2H), 4.04 (s, 6H), 3.03 (s, 6H).

(Synthesis of Compound L6c)

A nitrogen gas atmosphere was prepared in a reaction vessel, then, the compound L6b (46.54 g), acetic acid (375.7 g) and ion exchanged water (46.6 g) were added, and the mixture was stirred at 98° C. for 7 hours. The resultant reaction liquid was cooled down to room temperature, then, the resultant mixture was filtrated. The resultant solid was dried under reduced pressure at 50° C., to obtain a compound L6c (25.76 g) as a brown solid. The compound L6c showed an HPLC area percentage value of 93.6%.

LC-MS (APPI negative): m/z=443 [M−H]$^−$ $^1$H-NMR (CDCl$_3$, 300 MHz): δ (ppm)=8.00 (d, 2H), 7.52 (dd, 2H), 7.27 (d, 2H), 2.89 (d, 4H), 2.64 (d, 4H).

(Synthesis of Compound L6d)

A nitrogen gas atmosphere was prepared in a reaction vessel, then, the compound L6c (25.00 g), hydrazine monohydrate (11.29 g), sodium hydroxide (13.39 g) and ethylene glycol (779 g) were added, and the mixture was stirred at 130° C. for 9.5 hours. The resultant reaction liquid was cooled down to room temperature, toluene was added, then, the mixture was washed with ion exchanged water, and dried over anhydrous sodium sulfate. The resultant mixture was filtrated, and the resultant filtrate was concentrated under reduced pressure, to obtain a solid. The resultant solid was crystallized using a mixed solvent of toluene and acetonitrile, and the crystal was dried under reduced pressure at 50° C., to obtain a compound L6d (17.20 g) as a white solid. The compound L6d showed an HPLC area percentage value of 99.2%.

LC-MS (APPI positive): m/z=416 [M]$^+$ $^1$H-NMR (CDCl$_3$, 300 MHz): δ (ppm)=7.93 (d, 2H), 7.42 (dd, 2H), 7.24 (d, 2H), 2.20-2.08 (m, 4H), 2.00-1.86 (m, 4H), 1.72-1.55 (m, 2H), 1.51-1.36 (m, 2H).

(Synthesis of Compound L6e)

A nitrogen gas atmosphere was prepared in a reaction vessel, then, the compound L6d (7.04 g) and tetrahydrofuran (dehydrated product, 78 mL) were added, and the mixture was cooled down to −68° C. while stirring. Thereafter, into this was dropped a solution composed of sec-butyllithium, n-hexane and cyclohexane (1.04 mol/L, 16.5 mL), and the mixture was stirred at −68° C. for 1.5 hours. Thereafter, into this was dropped 1-iodohexane (14.29 g), and the mixture was heated up to room temperature overnight while stirring. Thereafter, to this was added ion exchanged water, then, heptane was added. then, the resultant mixture was washed with ion exchanged water, and dried over anhydrous sodium sulfate. The resultant mixture was filtrated through a filter paved with silica gel, and the resultant filtrate was concentrated under reduced pressure, to obtain a compound L6e as a colorless liquid (6.96 g). The compound L6e showed an HPLC area percentage value of 82.9%. This operation was repeated, to obtain a necessary amount of the compound L6e.

LC-MS (ESI positive): m/z=422 [M]$^+$

1H-NMR (CD$_2$Cl$_2$, 300 MHz): δ (ppm)=8.05 (d, 1H), 7.65 (d, 1H), 7.38 (dd, 1H), 7.34-7.23 (m, 2H), 7.15 (dd, 1H), 2.71-2.58 (m, 2H), 2.23-2.09 (m, 4H), 2.01-1.86 (m, 4H), 1.74-1.56 (m, 4H), 1.50-1.27 (m, 8H), 0.97-0.85 (m, 3H).

(Synthesis of Compound L6f)

A nitrogen gas atmosphere was prepared in a reaction vessel, then, the compound L6e (8.49 g) and cyclopentyl methyl ether (dehydrated product, 100 mL) were added, and the mixture was cooled down to −68° C. while stirring. Thereafter, into this was dropped a solution composed of sec-butyllithium, n-hexane and cyclohexane (1.04 mol/L, 27.0 mL), and the mixture was stirred at −68° C. for 2.5 hours. Thereafter, into this was dropped 2-isopropoxy-4,4,5,5-tetramethyl-1,3,2-dioxaborolane (5.62 g), and the mixture was heated up to room temperature overnight while stirring. The resultant mixture was washed with ion exchanged water, then, dried over anhydrous sodium sulfate. The resultant mixture was filtrated through a filter paved with silica gel, and the resultant filtrate was concentrated under reduced pressure, to obtain a compound L6f as a colorless liquid (9.79 g). The compound L6f showed an HPLC area percentage value of 83.9%.

LC-MS (APPI positive): m/z=470 [M]$^+$

1H-NMR (CD$_2$Cl$_2$, 300 MHz): δ (ppm)=8.31 (br, 1H), 7.82 (d, 1H), 7.66 (dd, 1H), 7.40 (d, 1H), 7.30 (d, 1H), 7.13 (dd, 1H), 2.71-2.62 (m, 2H), 2.24-2.09 (m, 4H), 2.03-1.88 (m, 4H), 1.74-1.56 (m, 4H), 1.50-1.29 (m, 20H), 0.97-0.85 (m, 3H).

(Synthesis of Compound L6)

2-Bromopyridine was purchased from Wako Pure Chemical Industries, Ltd.

A nitrogen gas atmosphere was prepared in a light-shielded reaction vessel, then, the compound L6f (9.79 g), 2-bromopyridine (4.93 g), tetrakis(triphenylphosphine)palladium(0) (0.24 g), toluene (171 g) and a 20 wt % tetraethylammonium hydroxide aqueous solution (61.4 g) were added, and the mixture was stirred at 80° C. for 7 hours. The resultant reaction liquid was cooled down to room temperature, washed with ion exchanged water, then, dried over anhydrous sodium sulfate. The resultant mixture was filtrated, and the resultant filtrate was concentrated under reduced pressure, to obtain a liquid. The resultant liquid was purified by silica gel column chromatography (a mixed solvent of hexane and chloroform), and the solvent was removed under reduced pressure, to obtain a liquid. The resultant liquid was purified by a recycling preparative system LC908 manufactured by Japan Analytical Industry Co., Ltd. (GPC column JAIGEL-2.5H), and the solvent was removed under reduced pressure. The resultant liquid was dried at 50° C. under reduced pressure, to obtain a compound L6 (4.55 g) as a colorless oil. The compound L6 showed an HPLC area percentage value of 99.9%.

LC-MS (APCI positive): m/z=422 [M+H]

$^1$H-NMR (CD$_2$Cl$_2$, 300 MHz): δ (ppm)=8.75-8.68 (m, 1H), 8.61 (d, 1H), 7.93-7.75 (m, 4H), 7.50 (d, 1H), 7.33 (d, 1H), 7.29-7.23 (m, 1H), 7.16 (dd, 1H), 2.73-2.63 (m, 2H), 2.27-2.12 (m, 4H) 2.09-1.92 (m, 4H), 1.77-1.59 (m, 4H), 1.53-1.26 (m, 8H), 0.97-0.85 (m, 3H).

<Example 6> Synthesis of Metal Complex M6

[Chemical Formula 123]

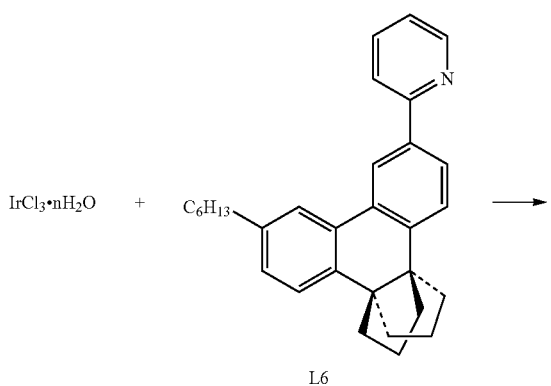

L6

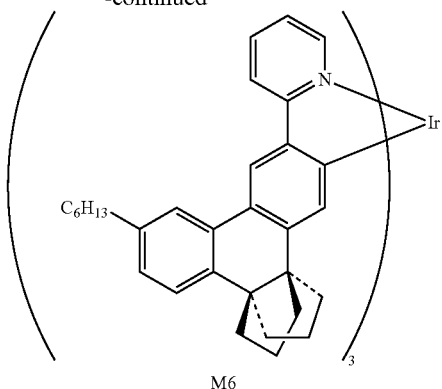

M6

(Synthesis of Metal Complex M6)

A nitrogen gas atmosphere was prepared in a light-shielded reaction vessel, then, the compound L6 (2.69 g) and 2-ethoxyethanol (200 g) were added, and the mixture was heated up to 85° C. Thereafter, into this was dropped iridium(III) chloride n-hydrate (1.00 g) dissolved in ion exchanged water (50 g), then, the mixture was stirred at 105° C. for 12.5 hours. The resultant reaction liquid was heated, the solvent was partially distilled off, then, the mixture was stirred at 130° C. for 19 hours. The resultant reaction liquid was cooled down to room temperature, then, methanol was added and the mixture was stirred. The resultant mixture was filtrated, the resultant solid was dried at 50° C. under reduced pressure, to obtain a yellow solid (2.45 g).

A nitrogen gas atmosphere was prepared in a light-shielded reaction vessel, then, the yellow solid (1.80 g) obtained above, silver trifluoromethanesulfonate (0.59 g), the compound L6 (0.89 g), 2,6-lutidine (0.28 g) and diethylene glycol dimethyl ether (18.0 g) were added, and the mixture was stirred at 150° C. for 5 hours. The resultant reaction liquid was cooled down to room temperature, methanol was added and the mixture was stirred at room temperature, and the resultant mixture was filtrated. The resultant solid was dissolved in dichloromethane, then, the resultant mixture was filtrated through a filter paved with silica gel. The resultant filtrate was concentrated under reduced pressure, the resultant solid was crystallized using a mixed solvent of dichloromethane and acetonitrile, and dried under reduced pressure at 50° C., to obtain a metal complex M6 (1.84 g) as a yellow solid. The metal complex M6 showed an HPLC area percentage value of 99.6%.

LC-MS (APCI positive): m/z=1455 [M+H]$^+$ $^1$H-NMR (CD$_2$Cl$_2$, 300 MHz): δ (ppm)=8.29 (s, 3H), 8.16 (d, 3H), 7.87 (s, 3H) 7.84-7.70 (m, 6H), 7.28 (d, 3H), 7.16-6.98 (m, 9H), 2.79-2.62 (m, 6H), 2.22-1.14 (m, 60H), 0.97 (t, 9H).

<Measurement Example 6> Measurement of PLQY and Light Emission Spectrum of Metal Complex M6

PLQY and emission spectrum were measured, using a xylene solution of the metal complex M5 (0.0008% by weight). Light emission showing the maximum peak of an emission spectrum at 518 nm was observed, and FWHM of this emission spectrum was 57 nm, and PLOY was 75%. The light emission spectrum of the metal complex M6 is shown in FIG. 4.

<Synthesis Example 6> Synthesis of Polymer Compound IP1

A polymer compound IP1 was synthesized by a method described in JP-A No. 2012-144722, using a monomer PM1 synthesized according to a method described in JP-A No. 2011-174062, a monomer PM2 synthesized according to a method described in International Publication WO2005/049546, a monomer PM3 synthesized according to a method described in International Publication WO02002/045184 and a monomer PM4 synthesized according to a method described in JP-A No. 2008-106241.

[Chemical Formula 124]

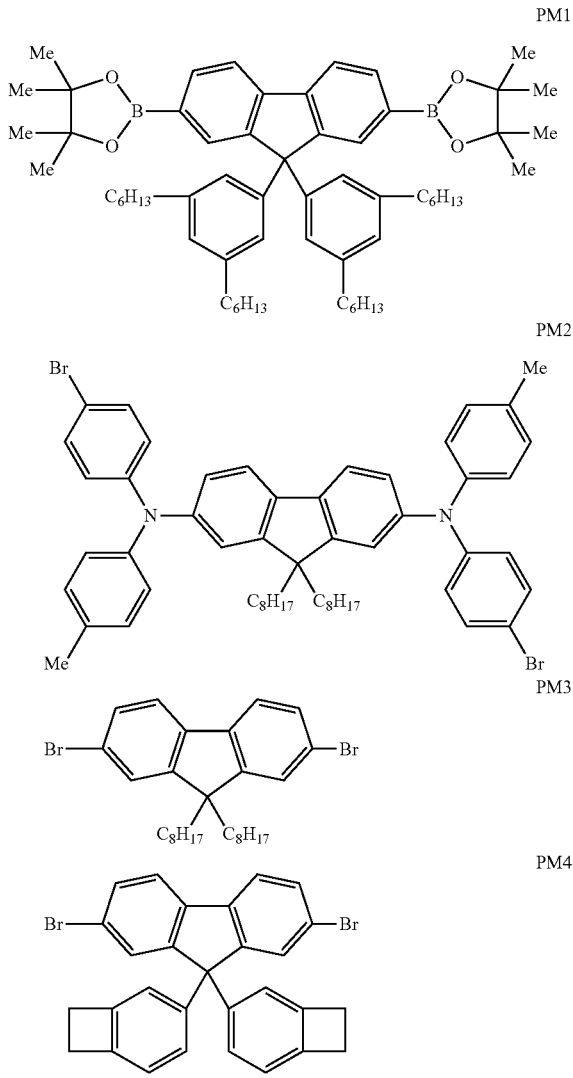

The polymer compound IP1 is a copolymer constituted of a constitutional unit derived from the monomer PM1, a constitutional unit derived from the monomer PM2, a constitutional unit derived from the monomer PM3 and a constitutional unit derived from the monomer PM4 at a molar ratio of 50:30:12.5:7.5, according to the theoretical values calculated from the amounts of the charged raw materials.

<Synthesis Example 7> Synthesis of Compound PM5

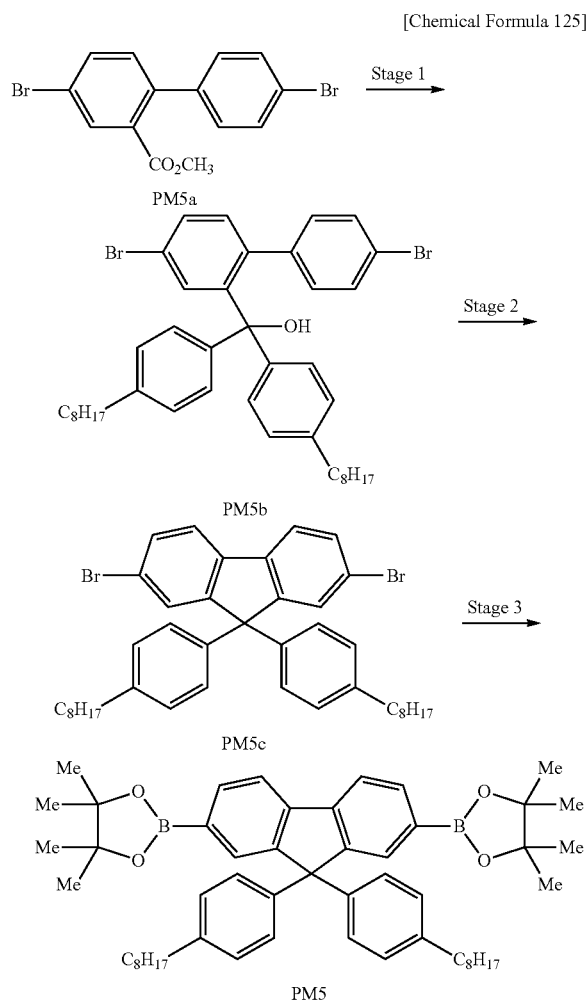

[Chemical Formula 125]

A compound PM5a was synthesized according to a method described in International Publication WO2012/086671.

(Stage 1: Synthesis of Compound PM5b)

A nitrogen gas atmosphere was prepared in a reaction vessel, then, 4-bromo-n-octylbenzene (250 g) and tetrahydrofuran (dehydrated product, 2.5 L) were added, and the mixture was cooled down to −70° C. or lower. Thereafter, a 2.5 mol/L concentration n-butyllithium hexane solution (355 mL) was dropped into this, and the mixture was stirred for 3 hours at −70° C. or lower. Thereafter, a solution prepared by dissolving the compound PM55a (148 g) in tetrahydrofuran (dehydrated product, 400 mL) was dropped into this, then, the mixture was warmed up to room temperature, and stirred at room temperature overnight. The resultant reaction mixture was cooled down to 0° C., then, water (150 mL) was added and the mixture was stirred. The resultant reaction mixture was concentrated under reduced pressure, to remove the organic solvent. To the resultant reaction mixture were added hexane (1 L) and water (200 mL), and the aqueous layer was removed by a liquid-separation operation. The resultant organic layer was washed with saturated saline, then, magnesium sulfate was added and the layer was dried. The resultant mixture was filtrated, and the resultant filtrate was concentrated under reduced pressure, to obtain a compound PM5b (330 g) as a yellow oily matter.

(Stage 2: Synthesis of Compound PM55c)

A nitrogen gas atmosphere was prepared in a reaction vessel, then, the compound PM5b (330 g) and dichloromethane (900 mL) were added, and the mixture was cooled down to 5° C. or lower. Thereafter, a 2.0 mol/L concentration boron trifluoride diethyl ether complex (245 mL) was dropped into this. Thereafter, the mixture was warmed up to room temperature, and stirred at room temperature overnight. The resultant reaction mixture was added into a vessel containing ice water (2 L), stirred for 30 minutes, then, the aqueous layer was removed. The resultant organic layer was washed with a 10% by weight potassium phosphate aqueous solution (1 L) once, with water (1 L) twice, then, dried over magnesium sulfate. The resultant mixture was filtrated, and the resultant filtrate was concentrated under reduced pressure, to obtain an oily matter. The resultant oily matter was dissolved in toluene (200 mL), then, the solution was passed through a filter paved with silica gel, to obtain a toluene solution 1. After the toluene solution 1 was obtained, toluene (about 3 L) was further passed through a filter paved with silica gel, to obtain a toluene solution 2. The toluene solution 1 and the toluene solution 2 were mixed, then, concentrated under reduced pressure, to obtain an oily matter. To the resultant oily matter was added methanol (500 mL), and the mixture was stirred. The resultant reaction mixture was filtrated, to obtain a solid. To the resultant solid was added a mixed solvent of butyl acetate and methanol, and recrystallization thereof was repeated, to obtain a compound PM5c (151 g) as a white solid. The resultant compound PM5c showed an HPLC area percentage value of 99.0% or more.

$^1$H-NMR (400 MHz/CDCl$_3$): δ (ppm)=7.56 (d, 2H), 7.49 (d, 2H), 7.46 (dd, 2H), 7.06~7.01 (m, 8H), 2.55 (t, 4H), 1.61~1.54 (m, 4H), 1.30~1.26 (m, 20H), 0.87 (t, 6H).

$^1$H-NMR (400 MHz/CDCl$_3$): δ (ppm)=7.56 (d, 2H), 7.49 (d, 2H), 7.46 (dd, 2H), 7.06 to 7.01 (m, 8H), 2.55 (t, 4H), 1.61 to 1.54 (m, 4H), 1.30 to 1.26 (m, 20H), 0.87 (t, 6H).

(Stage 3: Synthesis of Compound PM5)

A nitrogen gas atmosphere was prepared in a reaction vessel, then, the compound PM5c (100 g) and tetrahydrofuran (dehydrated product, 1000 mL) were added, and the mixture was cooled down to −70° C. or lower. Thereafter, a 2.5 mol/L concentration n-butyllithium hexane solution (126 mL) was dropped into this, and the mixture was stirred for 5 hours at −70° C. or lower. Thereafter, 2-isopropoxy-4,4,5,5-tetramethyl-1,3,2-dioxaborolane (81 mL) was dropped into this. Thereafter, the mixture was warmed up to room temperature, and stirred at room temperature overnight. The resultant reaction mixture was cooled down to −30° C., and a 2.0 mol/L hydrochloric acid diethyl ether solution (143 mL) was dropped. Thereafter, the mixture was warmed up to room temperature and concentrated under reduced pressure, to obtain a solid. To the resultant solid was added toluene (1.2 L), and the mixture was stirred at room temperature for 1 hour, then, passed through a filter paved with silica gel, to obtain a filtrate. The resultant filtrate was concentrated under reduced pressure, to obtain a solid. To the resultant solid was added methanol and the mixture was stirred, then, filtrated, to obtain a solid. The resultant solid was purified by repeating recrystallization thereof using isopropyl alcohol, then, dried under reduced pressure at 50° C. overnight, to obtain a compound PM5 (72 g) as a white solid. The resultant compound PM5 showed an HPLC area percentage value of 99.0% or more.

$^1$H-NMR (400 MHz/CDCl$_3$): δ (ppm)=7.82 (d, 2H), 7.81 (s, 2H), 7.76 (d, 2H), 7.11 (d, 4H), 7.00 (d, 4H), 2.52 (t, 4H), 1.59 to 1.54 (m, 4H), 1.36 to 1.26 (m, 20H), 1.31 (s, 24H), 0.87 (t, 6H).

<Synthesis Example 8> Synthesis of Polymer Compound P1

(Stage 1)

An inert gas atmosphere was prepared in a reaction vessel, then, the monomer PM5 (4.77 g) (identical to the compound PM5), a monomer PM6 (0.773 g) synthesized according to a method described in International Publication WO2012/086671, the monomer PM3 (1.97 g), a monomer PM7 (0.331 g) synthesized according to a method described in International Publication WO2009/131255, a monomer PM8 (0.443 g) synthesized according to a method described in JP-A No. 2004-143419 and toluene (67 mL) were added, and the mixture was stirred while heating at 105° C.

[Chemical Formula 126]

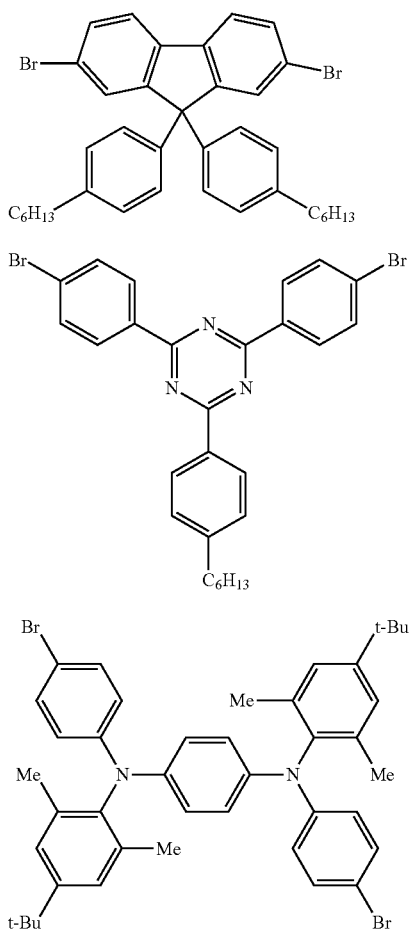

Thereafter, to this was added bistriphenylphosphinepalladium dichloride (4.2 mg), then, a 20% by weight tetraethylammonium hydroxide aqueous solution (20 mL) was dropped, then, the mixture was stirred for 3 hours under reflux.

(Stage 3)

Thereafter, to this were added phenylboronic acid (0.077 g), bistriphenylphosphinepalladium dichloride (4.2 mg), toluene (60 mL) and a 20% by weight tetraethylammonium hydroxide aqueous solution (20 mL), and the mixture was stirred for 24 hours under reflux.

(Stage 4)

The organic layer was separated from the aqueous layer, then, to the resultant organic layer were added sodium N,N-diethyldithiocarbamate trihydrate (3.33 g) and ion exchanged water (67 mL), and the mixture was stirred at 85° C. for 2 hours. The organic layer was separated from the aqueous layer, then, the resultant organic layer was washed with ion exchanged water (78 mL) twice, with a 3% by weight acetic acid aqueous solution (78 mL) twice and with ion exchanged water (78 mL) twice in this order. The organic layer was separated from the aqueous layer, then, the resultant organic layer was dropped into methanol to cause preparation of a solid which was then filtrated and dried, to obtain a solid. The resultant solid was dissolved in toluene, and the solution was passed through a silica gel column and an alumina column through which toluene had been passed previously. The resultant solution was dropped into methanol to cause preparation of a solid which was then filtrated and dried, to obtain a polymer compound P1 (4.95 g). The polymer compound P1 had a polystyrene-equivalent number-average molecular weight (Mn) of $1.4 \times 10^5$ and a polystyrene-equivalent weight-average molecular weight (Mw) of $4.1 \times 10^5$.

The polymer compound P1 is a copolymer constituted of a constitutional unit derived from the monomer PM5, a constitutional unit derived from the monomer PM6, a constitutional unit derived from the monomer PM3, a constitutional unit derived from the monomer PM7 and a constitutional unit derived from the monomer PM8 at a molar ratio of 50:10:30:5:5, according to the theoretical values calculated from the amounts of the charged raw materials.

<Synthesis Example 9> Synthesis of Polymer Compound P2

A polymer compound P2 was synthesized by a method of "Polymer compound B" described in JP-A No. 2012-036388, using a monomer PM9 synthesized according to a method described in JP-A No. 2010-189630, a monomer PM6, and a monomer PM10 synthesized according to a method described in JP-A No. 2012-036388. The polymer compound P2 had a Mn of $9.6 \times 10^4$ and a Mw of $2.2 \times 10^5$.

[Chemical Formula 127]

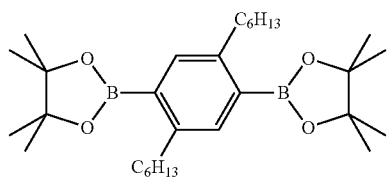

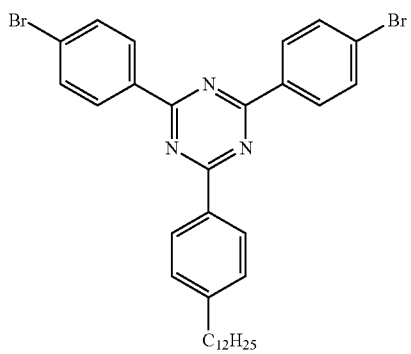

PM10

The polymer compound P2 is a copolymer constituted of a constitutional unit derived from the monomer PM9, a constitutional unit derived from the monomer PM6 and a constitutional unit derived from the monomer PM10 at a molar ratio of 50:40:10, according to the theoretical values calculated from the amounts of the charged raw materials.

<Example D1> Fabrication and Evaluation of Light Emitting Device D1

(Fabrication of Light Emitting Device D1)
(Formation of Anode and Hole Injection Layer)

A glass substrate was attached with an ITO film with a thickness of 45 nm by a sputtering method, to form an anode. On the anode, a polythiophene sulfonic acid type hole injection agent AQ-1200 (manufactured by Plextronics) was spin-coated to form a film with a thickness of 65 nm, and the film was heated on a hot plate at 170° C. for 15 minutes under an air atmosphere, to form a hole injection layer.
(Formation of Hole Transporting Layer)

A polymer compound IP1 was dissolved at a concentration of 0.70 wt % in xylene. The resultant xylene solution was spin-coated on the hole injection layer to form a film with a thickness of 20 nm, and the film was heated on a hot plate at 180° C. for 60 minutes under a nitrogen gas atmosphere, to form a hole transporting layer.
(Formation of Light Emitting Layer)

The polymer compound P1 and the metal complex M1 (polymer compound P1/metal complex M1=92.5 wt %/7.5 wt %) were dissolved at a concentration of 1.7 wt % in xylene. The resultant xylene solution was spin-coated on the hole transporting layer to form a film with a thickness of 90 nm, and the film was heated at 150° C. for 10 minutes under a nitrogen gas atmosphere, to form a light emitting layer.

(Formation of Cathode)

The substrate carrying the light emitting layer formed thereon was placed in a vapor deposition machine and the internal pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing with a glass substrate was performed, to fabricate a light emitting device D1.
(Evaluation of Light Emitting Device D1)

When voltage was applied to the light emitting device D1, light emission having the maximum peak of the light emission spectrum at 635 nm was observed, and CIE chromaticity coordinate (x,y) was (0.683,0.314). This light emission spectrum had a FWHM of 48 nm. When the light emitting device D1 was used in combination with a color filter A shown in FIG. 5, the external quantum efficiency at 1000 cd/m$^2$ was 12.2%. These results are shown in Table 2 below.

<Example D2> Fabrication and Evaluation of Light Emitting Device D2

A light emitting device D2 was fabricated in the same manner as in Example D1, excepting that the polymer compound P1 and the metal complex M2 were used instead of the polymer compound P1 and the metal complex M1 in Example D1.

When voltage was applied to the light emitting device D2, light emission having the maximum peak of the light emission spectrum at 635 nm was observed, and CIE chromaticity coordinate (x,y) was (0.685,0.312). This light emission spectrum had a FWHM of 48 nm. When the light emitting device D2 was used in combination with a color filter A shown in FIG. 5, the external quantum efficiency at 1000 cd/m$^2$ was 13.4%. These results are shown in Table 2 below.

<Comparative Example CD1> Fabrication and Evaluation of Light Emitting Device CD1

A light emitting device CD1 was fabricated in the same manner as in Example D1, excepting that the polymer compound P1 and the metal complex CM1 were used instead of the polymer compound P1 and the metal complex M1 in Example D1.

When voltage was applied to the light emitting device CD1, light emission having the maximum peak of the light emission spectrum at 615 nm was observed, and CIE chromaticity coordinate (x,y) was (0.645,0.352). This light emission spectrum had a FWHM of 81 nm. When the light emitting device CD1 was used in combination with a color filter A shown in FIG. 5, the external quantum efficiency at 1000 cd/m$^2$ was 10.8%. These results are shown in Table 2 below.

TABLE 2

| light emitting device | metal complex | light emission spectrum maximum peak wavelength [nm] (1k cd/m$^2$) | CIE chromaticity coordinate (1k cd/m$^2$) | light emission spectrum FWHM [nm] (1k cd/m$^2$) | EQE [%] when using color filter in combination |
|---|---|---|---|---|---|
| D1 | M1 | 635 | (0.683, 0.314) | 48 | 12.2 |
| D2 | M2 | 635 | (0.685, 0.312) | 48 | 13.4 |
| CD1 | CM1 | 615 | (0.645, 0.352) | 81 | 10.8 |

These results show that when a light emitting device obtained by using the metal complexes M1 and M2 of the present invention is used in combination with a color filter, the external quantum efficiency is more excellent, as compared with a case in which a light emitting device produced by using the metal complex CM1 is used in combination with a color filter.

<Example D3> Fabrication and Evaluation of Light Emitting Device D3

A light emitting device D3 was fabricated in the same manner as in Example D1, excepting that the polymer compound P1 and the metal complex M3 were used instead of the polymer compound P1 and the metal complex M1 in Example D1.

When voltage was applied to the light emitting device D3, light emission having the maximum peak of the light emission spectrum at 650 nm was observed, and CIE chromaticity coordinate (x,y) was (0.689,0.298). This light emission spectrum had a FWHM of 54 nm. When the light emitting device D3 was used in combination with a color filter A shown in FIG. 5, the external quantum efficiency at 1000 cd/m$^2$ was 7.30%. These results are shown in Table 3 below.

TABLE 3

| light emitting device | metal complex | light emission spectrum maximum peak wavelength [nm] (1k cd/m$^2$) | CIE chromaticity coordinate (1k cd/m$^2$) | light emission spectrum FWHM [nm] (1k cd/m$^2$) | EQE [%] when using color filter in combination |
|---|---|---|---|---|---|
| D3 | M3 | 650 | (0.689, 0.298) | 54 | 7.30 |

These results show that when a light emitting device obtained by using the metal complex M3 of the present invention is used in combination with a color filter, the external quantum efficiency is more excellent, as compared with a case in which a light emitting device produced by using the metal complex CM2 and the metal complex CM3 is used in combination with a color filter.

<Example D4> Fabrication and Evaluation of Light Emitting Device D4

(Fabrication of Light Emitting Device D4)
(Formation of Anode and Hole Injection Layer)

A glass substrate was attached with an ITO film with a thickness of 45 nm by a sputtering method, to form an anode. On the anode, a polythiophene sulfonic acid type hole injection agent AQ-1200 (manufactured by Plextronics) was spin-coated to form a film with a thickness of 65 nm, and the film was heated on a hot plate at 170° C. for 15 minutes under an air atmosphere, to form a hole injection layer.

(Formation of Hole Transporting Layer)

A polymer compound IP1 was dissolved at a concentration of 0.70 wt % in xylene. The resultant xylene solution was spin-coated on the hole injection layer to form a film with a thickness of 20 nm, and the film was heated on a hot plate at 180° C. for 60 minutes under a nitrogen gas atmosphere, to form a hole transporting layer.

(Formation of Light Emitting Layer)

The polymer compound P2 and the metal complex M4 (polymer compound P2/metal complex M4=70 wt %/30 wt %) were dissolved at a concentration 1.6 wt % in chlorobenzene. The resultant chlorobenzene solution was spin-coated on the hole transporting layer to form a film with a thickness of 80 nm, and the film was heated at 150° C. for 10 minutes under a nitrogen gas atmosphere, for form a light emitting layer.

(Formation of Cathode)

The substrate carrying the light emitting layer formed thereon was placed in a vapor deposition machine and the internal pressure was reduced to 1.0×10$^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing with a glass substrate was performed, to fabricate a light emitting device D4.

(Evaluation of Light Emitting Device D4)

When voltage was applied to the light emitting device D4, light emission having the maximum peak of the light emission spectrum at 580 nm was observed, and CIE chromaticity coordinate (x,y) was (0.543,0.455). This light emission spectrum had a FWHM of 37 nm. When the light emitting device D4 was used in combination with a color filter B shown in FIG. 5, the external quantum efficiency at 1000 cd/m$^2$ was 18.1%. These results are shown in Table 4 below.

<Example D5> Fabrication and Evaluation of Light Emitting Device D5

A light emitting device D5 was fabricated in the same manner as in Example D4, excepting that the polymer compound P2 and the metal complex M5 were used instead of the polymer compound P2 and the metal complex M4 in Example D4.

When voltage was applied to the light emitting device D5, light emission having the maximum peak of the light emission spectrum at 575 nm was observed, and CIE chromaticity coordinate (x,y) was (0.530,0.467). This light emission spectrum had a FWHM of 43 nm. When the light emitting device D5 was used in combination with a color filter B shown in FIG. 5, the external quantum efficiency at 1000 cd/m$^2$ was 12.2%. These results are shown in Table 4 below.

TABLE 4

| light emitting device | metal complex | light emission spectrum maximum peak wavelength [nm] (1k cd/m$^2$) | CIE chromaticity coordinate (1k cd/m$^2$) | light emission spectrum FWHM [nm] (1k cd/m$^2$) | EQE [%] when using color filter in combination |
|---|---|---|---|---|---|
| D4 | M4 | 580 | (0.543, 0.455) | 37 | 18.1 |
| D5 | M5 | 575 | (0.530, 0.467) | 43 | 12.2 |

<Example D6> Fabrication and Evaluation of Light Emitting Device D6

A light emitting device D6 was fabricated in the same manner as in Example D4, excepting that the polymer compound P2 and the metal complex M6 were used instead of the polymer compound P2 and the metal complex M4 in Example D4.

When voltage was applied to the light emitting device D6, light emission having the maximum peak of the light emission spectrum at 520 nm was observed, and CIE chromaticity coordinate (x,y) was (0.314,0.640). This light emission spectrum had a FWHM of 60 nm. When the light emitting device D6 was used in combination with a color filter C shown in FIG. 5, the external quantum efficiency at 1000 cd/m² was 9.33%. These results are shown in Table 5 below.

TABLE 5

| light emitting device | metal complex | light emission spectrum maximum peak wavelength [nm] (1k cd/m²) | CIE chromaticity coordinate (1k cd/m²) | light emission spectrum FWHM [nm] (1k cd/m²) | EQE [%] when using color filter in combination |
|---|---|---|---|---|---|
| D6 | M6 | 520 | (0.314, 0.640) | 60 | 9.33 |

INDUSTRIAL APPLICABILITY

According to the present invention, a metal complex excellent in the quantum yield and excellent in the full width at half maximum of the light emission spectrum can be provided. Additionally, according to the present invention, a composition comprising the metal complex and a light emitting device obtained by using the metal complex can be provided. Because the metal complex of the present invention is excellent in the quantum yield, a light emitting device obtained by using the metal complex is excellent in the external quantum efficiency. Further, because the metal complex of the present invention is excellent in the full width at half maximum of the light emission spectrum, if a light emitting device obtained by using the metal complex is used in combination with a color filter, its external quantum efficiency is further excellent when the cavity of the light emitting device obtained by using the metal complex is controlled.

The invention claimed is:

1. A metal complex represented by one of the following formulae (1), (2) or (3):

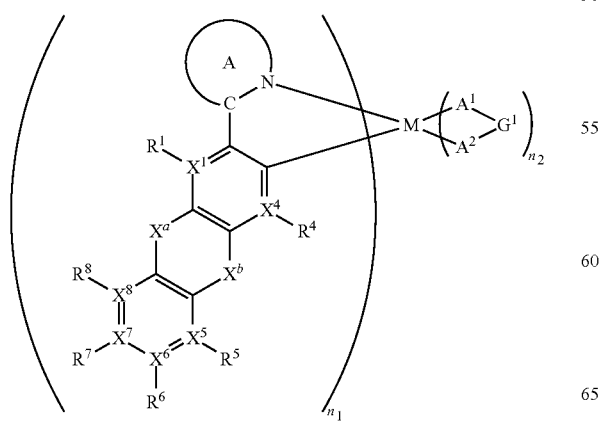

(1)

-continued

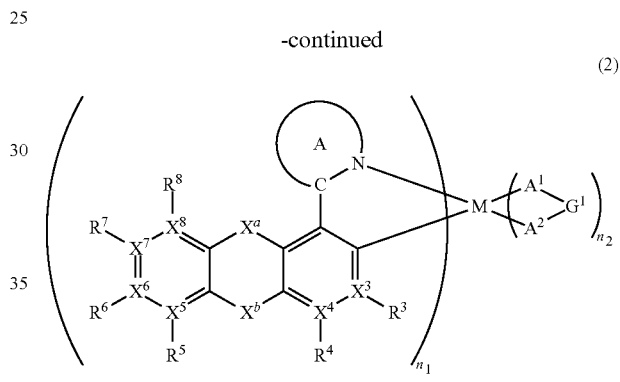

(2)

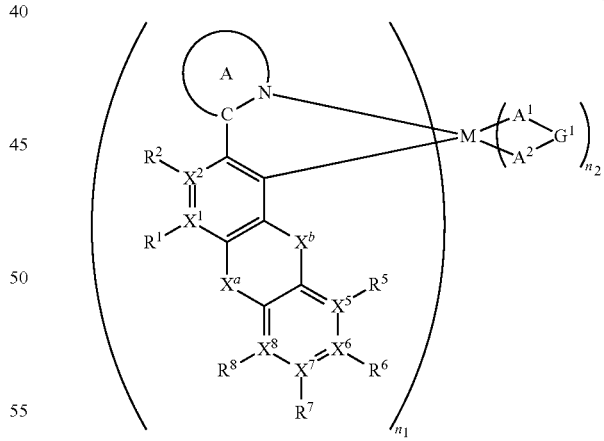

(3)

wherein
M represents an iridium atom or a platinum atom,
$n_1$ represents 1, 2 or 3 and $n_2$ represents 0, 1 or 2, provided that $n_1+n_2$ is 3 when M is an iridium atom and $n_1+n_2$ is 2 when M is a platinum atom,
$X^1$, $X^2$, $X^3$, $X^4$, $X^5$, $X^6$, $X^7$ and $X^8$ each independently represent a nitrogen atom or a carbon atom, provided that at least two selected from the group consisting of $X^5$, $X^6$, $X^7$ and $X^8$ are carbon atoms, and when there are a plurality of $X^1$, $X^2$, $X^3$, $X^4$, $X^5$, $X^6$, $X^7$ or $X^8$, they may be the same or different at each occurrence, provided that $R^1$ is not present when $X^1$ is a nitrogen atom, $R^2$ is not present when $X^2$ is a nitrogen atom, $R^3$ is not present when $X^3$ is a nitrogen atom, $R^4$ is not present when $X^4$ is a nitrogen atom, $R^5$ is not present when $X^5$ is a nitrogen atom, $R^6$ is not present when $X^6$ is a nitrogen atom, $R^7$ is not present when $X^7$ is a nitrogen atom, and $R^8$ is not present when $X^8$ is a nitrogen atom, $R^1$, $R^2$, $R^3$, $R^4$, $R^5$, $R^6$, $R^7$ and $R^8$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent, provided that $R^1$ and $R^2$, $R^3$ and $R^4$, $R^5$ and $R^6$, $R^6$ and $R^7$, and $R^7$ and $R^8$ each may be combined together to form a ring together with the atoms to which they are attached, and when there are a plurality of $R^1$, $R^2$, $R^3$, $R^4$, $R^5$, $R^6$, $R^7$ or $R^8$, they may be the same or different at each occurrence, $X^a$ and $X^b$ each represent a single bond or a group represented by —$CR^{11}R^{12}$—$CR^{13}R^{14}$—, provided that one of $X^a$ and $X^b$ is a single bond, and the other is a group represented by —$CR^{11}R^{12}$—$CR^{13}R^{14}$—, wherein $R^{11}$, $R^{12}$, $R^{13}$ and $R^{14}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent, provided that $R^{11}$ and $R^{12}$, $R^{13}$ and $R^{14}$, $R^{11}$ and $R^{13}$, and $R^{12}$ and $R^{14}$ each may be combined together to form a ring together with the atoms to which they are attached, and when there are a plurality of $R^{11}$, $R^{12}$, $R^{13}$ or $R^{14}$, they may be the same or different at each occurrence, provided that at least one selected from the group consisting of $R^{11}$, $R^{12}$, $R^{13}$ and $R^{14}$ is an alkyl group, a cycloalkyl group, an alkoxy group, a cycloalkoxy group, an aryl group, an aryloxy group, a monovalent heterocyclic group or a halogen atom, ring A represents a heteroaromatic ring, the heteroaromatic ring optionally having a substituent, and when there are a plurality of ring A, they may be the same or different, and $A^1$-$G^1$-$A^2$ represents an anionic bidentate ligand, wherein $A^1$ and $A^2$ each independently represent a carbon atom, an oxygen atom or a nitrogen atom, the foregoing atoms each optionally being an atom constituting a ring, $G^1$ represents a single bond or an atomic group constituting the bidentate ligand together with $A^1$ and $A^2$, and when there are a plurality of $A^1$-$G^1$-$A^2$, they may be the same or different, wherein ring A has a group represented by the following formula (D-A) or (D-B) as a substituent:

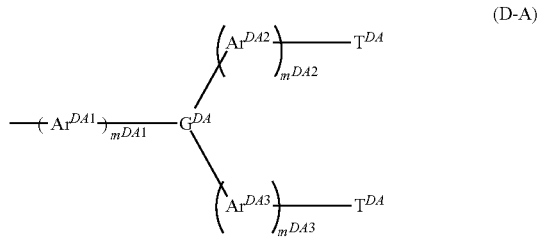

wherein $m^{DA1}$, $m^{DA2}$ and $m^{DA3}$ each independently represent an integer of 0 or more, $G^{DA}$ represents a nitrogen atom, an aromatic hydrocarbon group or a heterocyclic group, the foregoing groups each optionally having a substituent, $Ar^{DA1}$, $Ar^{DA2}$ and $Ar^{DA3}$ each independently represent an arylene group or a divalent heterocyclic group, the foregoing groups each optionally having a substituent, and when there are a plurality of $Ar^{DA1}$, $Ar^{DA2}$ or $Ar^{DA3}$, they may be the same or different at each occurrence, and $T^{DA}$ represents an aryl group or a monovalent heterocyclic group, the foregoing groups each optionally having a substituent, and the plurality of $T^{DA}$ may be the same or different:

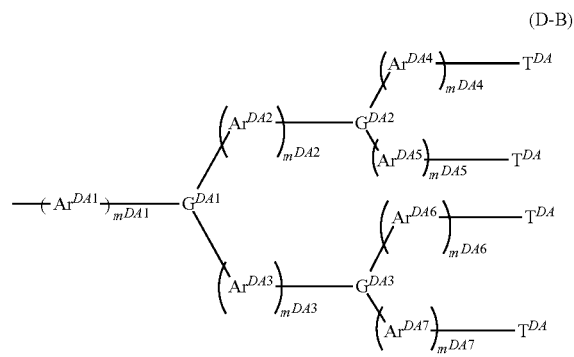

wherein $m^{DA1}$, $m^{DA2}$, $m^{DA3}$, $m^{DA4}$, $m^{DA5}$, $m^{DA6}$ and $m^{DA7}$ each independently represents an integer of 0 or more, $G^{DA1}$, $G^{DA2}$, and $G^{DA3}$ each independently represents a nitrogen atom, an aromatic hydrocarbon group or a heterocyclic group, the foregoing groups each optionally having a substituent, $m^{DA2}$ is an integer of 1 or more when $G^{DA1}$ and $G^{DA2}$ are each a nitrogen atom, $m^{DA3}$ is an integer of 1 or more when $G^{DA1}$ and $G^{DA3}$ are each a nitrogen atom, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, the foregoing groups each optionally having a substituent, and when there are a plurality of $Ar^{DA1}$, $Ar^{DA2}$, $Ar^{DA3}$, $Ar^{DA4}$, $Ar^{DA5}$, $Ar^{DA6}$ or $Ar^{DA7}$, they may be the same or different at each occurrence, and $T^{DA}$ represents an aryl group or a monovalent heterocyclic group, the foregoing groups each optionally having a substituent, and the plurality of $T^{DA}$ may be the same or different.

2. The metal complex according to claim 1 represented by one of the following formulae (1-1), (1-2) or (2-1):

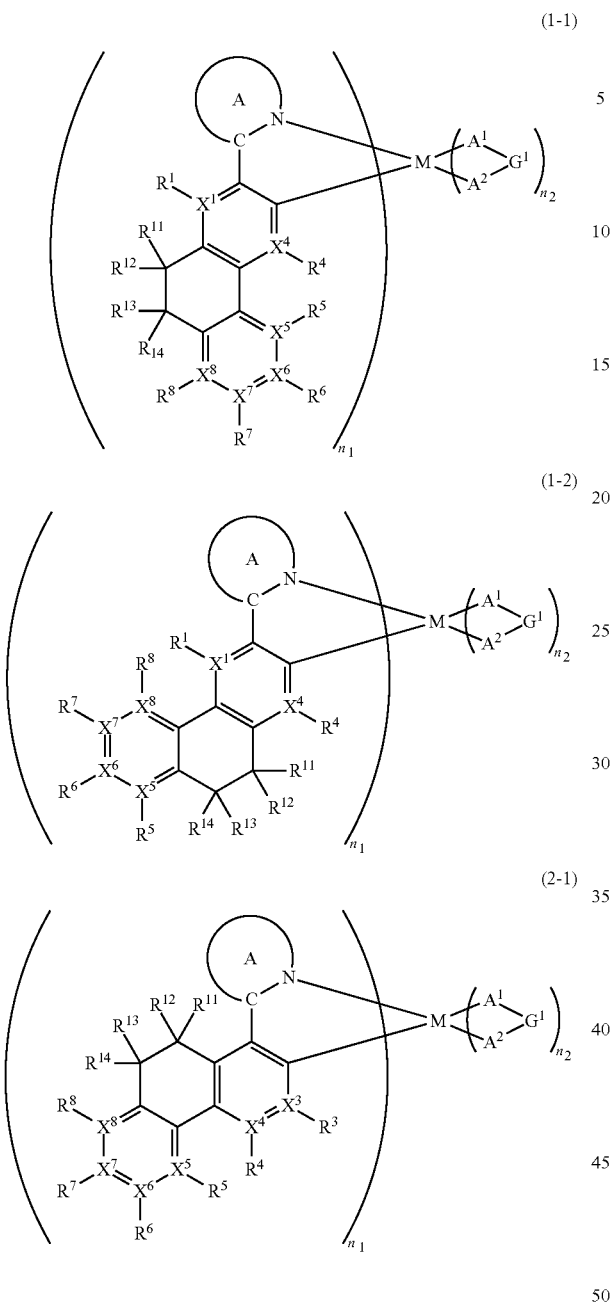

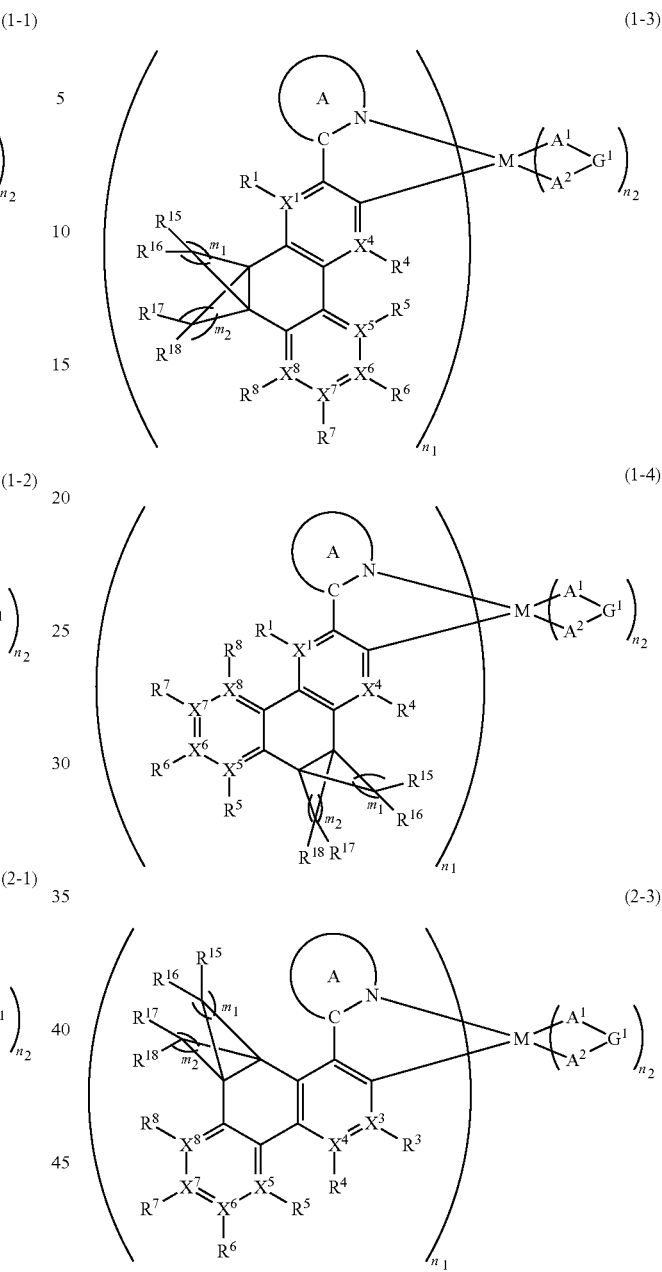

wherein M, $n_1$, $n_2$, $X^1$, $X^3$, $X^4$, $X^5$, $X^6$, $X^7$, $X^8$, $R^1$, $R^3$, $R^4$, $R^5$, $R^6$, $R^7$, $R^8$, $R^{11}$, $R^{12}$, $R^{13}$, $R^{14}$, ring A and $A^1$-$G^1$-$A^2$ are as defined above.

3. The metal complex according to claim 1, wherein $R^{11}$, $R^{12}$, $R^{13}$ and $R^{14}$ are each an alkyl group optionally having a substituent.

4. The metal complex according to claim 3, wherein $R^{11}$ and $R^{13}$ are combined to form a ring together with the atoms to which they are attached, and $R^{12}$ and $R^{14}$ are combined to form a ring together with the atoms to which they are attached.

5. The metal complex according to claim 4 represented by one of the following formulae (1-3), (1-4) or (2-3):

wherein

M, $n_1$, $n_2$, $X^1$, $X^3$, $X^4$, $X^5$, $X^6$, $X^7$, $X^8$, $R^1$, $R^3$, $R^4$, $R^5$, $R^6$, $R^7$, $R^8$, ring A and $A^1$-$G^1$-$A^2$ are as defined above, $m_1$ and $m_2$ each independently represent an integer of 1 to 5, and when there are a plurality of $m_1$ or $m_2$, they may be the same or different at each occurrence, and $R^{15}$, $R^{16}$, $R^{17}$ and $R^{18}$ each independently represent a hydrogen atom, an alkyl group, a cycloalkyl group, an alkoxy group, a cycloalkoxy group, an aryl group, an aryloxy group, a monovalent heterocyclic group or a halogen atom, the foregoing groups each optionally having a substituent, and when there are a plurality of $R^{15}$, $R^{16}$, $R^{17}$ or $R^{18}$, they may be the same or different at each occurrence.

6. The metal complex according to claim 5, wherein $m_1$ and $m_2$ are each 3 or 4.

7. The metal complex according to claim 1, wherein $X^1$, $X^2$, $X^3$, $X^4$, $X^5$, $X^6$, $X^7$ and $X^8$ are each a carbon atom.

8. The metal complex according to claim 1, wherein ring A is a pyridine ring optionally having a substituent, a pyrimidine ring optionally having a substituent, a quinoline ring optionally having a substituent, an isoquinoline ring optionally having a substituent, an imidazole ring optionally having a substituent or a triazole ring optionally having a substituent.

9. The metal complex according to claim 1 satisfying at least one of the following requirements (A), (B) and (C):
(A) ring A has an alkyl group, a cycloalkyl group, an aryl group or a monovalent heterocyclic group as a substituent,
(B) in the formula (1) $R^1$, $R^4$, $R^5$ and $R^8$ are each a hydrogen atom, an alkyl group, a cycloalkyl group, an aryl group or a monovalent heterocyclic group, in the formula (2) $R^3$, $R^4$, $R^5$, and $R^8$ are each a hydrogen atom, an alkyl group, a cycloalkyl group, an aryl group, or a monovalent heterocyclic group, and in the formula (3), $R^1$, $R^2$, $R^5$, and $R^8$ are each a hydrogen atom, an alkyl group, a cycloalkyl group, an aryl group, or a monovalent heterocyclic group,
(C) $R^6$ and $R^7$ are each a hydrogen atom, an alkyl group, a cycloalkyl group, an aryl group, a monovalent heterocyclic group or a halogen atom.

10. The metal complex according to claim 1, wherein the group represented by the formula (D-A) is a group represented by one of the following formulae (D-A1), (D-A2) or (D-A3):

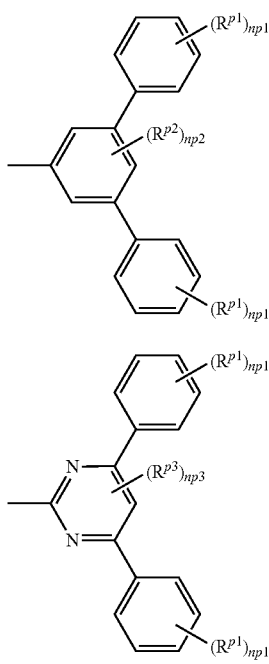

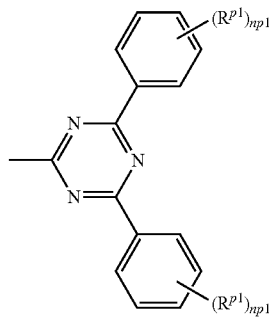

wherein $R^{p1}$, $R^{p2}$ and $R^{p3}$ each independently represent an alkyl group, a cycloalkyl group, an alkoxy group, a cycloalkoxy group or a halogen atom, and when there are a plurality of $R^{p1}$ or $R^{p2}$, they may be the same or different at each occurrence, and np1 represents an integer of 0 to 5, np2 represents an integer of 0 to 3, and np3 represents 0 or 1, and the plurality of np1 may be the same or different.

11. The metal complex according to claim 1, wherein M is an iridium atom, $n_1$ is 3, and $n_2$ is 0.

12. A composition comprising:

the metal complex according to claim 1, and a polymer compound comprising a constitutional unit represented by the following formula (Y):

$$\text{---}\mathrm{Ar}^{Y1}\text{---} \quad (Y)$$

wherein $\mathrm{Ar}^{Y1}$ represents an arylene group, a divalent heterocyclic group, or a divalent group in which at least one arylene group and at least one divalent heterocyclic group are bonded directly to each other, the foregoing groups each optionally having a substituent.

13. A composition comprising:

the metal complex according to claim 1, and at least one material selected from the group consisting of a hole transporting material, a hole injection material, an electron transporting material, an electron injection material, a light emitting material, an antioxidant and a solvent.

14. A light emitting device comprising the metal complex according to claim 1.

* * * * *